United States Patent
Guntaka et al.

(10) Patent No.: US 7,348,011 B2
(45) Date of Patent: Mar. 25, 2008

(54) HEPATITIS C VIRUS VACCINE

(75) Inventors: Ramareddy Venkata Guntaka, Memphis, TN (US); Chittoor Mohammad Habibullah, Andhra Pradesh (IN); Mohammad Nanne Khaja, Andhra Pradesh (IN); Chandra Madhavi, Andhra Pradesh (IN)

(73) Assignee: Sudershan Biotech Ltd., Andhra Pradesh (IN)

( * ) Notice: Subject to any disclaimer, the term of this patent is extended or adjusted under 35 U.S.C. 154(b) by 0 days.

(21) Appl. No.: 11/447,049

(22) Filed: Jun. 6, 2006

(65) Prior Publication Data
US 2007/0065911 A1  Mar. 22, 2007

Related U.S. Application Data

(60) Provisional application No. 60/689,090, filed on Jun. 10, 2005.

(51) Int. Cl.
*A61K 39/00* (2006.01)
*C07K 14/00* (2006.01)

(52) U.S. Cl. .................... 424/189.1; 530/350
(58) Field of Classification Search .............. None
See application file for complete search history.

(56) References Cited

OTHER PUBLICATIONS

NCBI Report Q6DQ94 (submitted Jun. 2004 and created Aug. 16, 2004).*
Huang et al., Recent development of therapeutics for chronic HCV infection, Antiviral Research, 2006, 71:351-362.*

* cited by examiner

*Primary Examiner*—Bruce R. Campell
*Assistant Examiner*—Nicole E Kinsey
(74) *Attorney, Agent, or Firm*—Oliff & Berridge PLC

(57) ABSTRACT

The present invention relates to isolation of a novel Hepatitis C virus, more particularly, the present invention relates to a viral class Hepatitis C, polypeptides, polynucleotide, vaccine and antibodies derived there from.

9 Claims, 48 Drawing Sheets

HCV – CORE Protein

Figure 1:
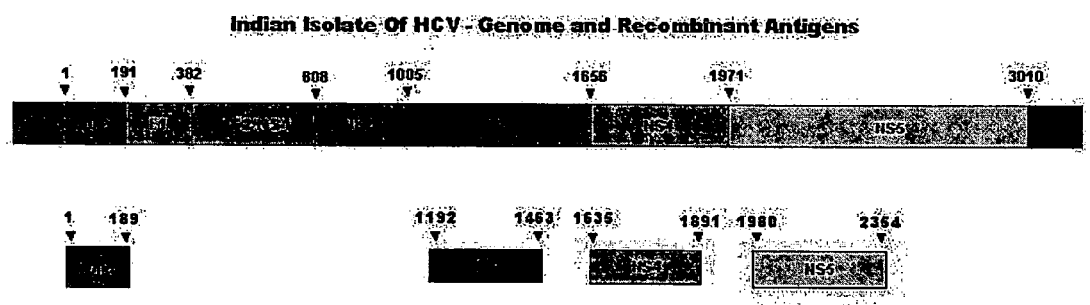

1 – Whole cell pellet without induced protein

2 – Whole cell pellet with induced protein

3 – Protein Marker (from top to bottom 116, 66.2, 45, 35, 25, 18.4 and 14.4 kDa)

4 – Purified CORE Protein

HCV – NS3 Protein

1 - Whole cell pellet without induced protein

2 - Whole cell pellet with induced protein

3 - Protein Marker (from top to bottom 116, 66.2, 45, 35, 25, 18.4 and 14.4 kDa)

4 - Purified NS3 Protein

HCV – NS4 PROTEIN

1 - Whole cell pellet without induced protein

2 - Whole cell pellet with induced protein

3 - Protein Marker (from top to bottom (116, 66.2, 45, 35 and 25 kDA)

4 - Purified NS4 protein

Fig. 9

5'UTR: 341 bases – SEQ ID No. 3

CORE: 573 bases – SEQ ID No. 5 and corresponding polypeptide (SEQ ID No.6)

E1: 576 bases – SEQ ID No. 7 and corresponding polypeptide (SEQ ID No.8)

E2/NS1: 1278 bases – SEQ ID No. 9 and corresponding polypeptide (SEQ ID No.10)

NS2: 591 bases – SEQ ID No. 11 and corresponding polypeptide (SEQ ID No.12)

NS3: 1953 bases – SEQ ID No. 13 and corresponding polypeptide (SEQ ID No.14)

NS4: 945 bases – SEQ ID No. 15 and corresponding polypeptide (SEQ ID No.16)

NS5: 3117 bases – SEQ ID No. 17 and corresponding polypeptide (SEQ ID No.18)

3'UTR: 67 bases– SEQ ID No. 4

AY651061: 5' UTR:

gccagcccctgatgggggcgacactccgccatgaatcactcccctgtgaggaactactgtcttcacgcagaaagcgtct
agccatggcgttagtatgagtgtcgtgcagcctccaggacccccctcccgggagagccatagtggtctgcggaaccggt
gagtacaccggaattgccaggacgaccgggtcctttcttggataaacccgctcaacgcctggagatttgggcgtgccccc
gcaagactgctagccgagtagtgttgggtcgcgaaaggccttgtggtactgcctgatagggtgcttgcgagtgccccggg
aggtctcgtagaccgtgcacc

AY651061: CORE:

atgagcacgaatcctaaacctcaaagaaaaaccaaacgtaacaccaaccgtcgcccacaggacgtcaagttcccggggtg
gcggacagatcgttggtggagtttacttgttgccgcgcaggggccctagattgggtgtgcgcgcgacgaggaagacttcc
gagcggtcgcaacctcgaggtagacgtcagcctatccccaaggcacgtcggcccgagggcaggacctgggctcagccgg
gtaccttggcccctctatggcaatgagggctgcgggtgggcgggatggctcctgtctcccgcggctctcggcctagtt
ggggccccacagaccccggcgtagatcgcgcaatttgggtaaggtcatcgataccctttacgtatggcttcgccgacctc
atggggtacataccgctcgtcggcgccccccttgggggcgctgccagggccctggcgcacggcgtccgggtcctggaaga
cggcgtgaactatgcaacagggaaccttcctggttgctctttctctatcttccttctggccctgctctcttgcttgactgtgcccgcttc
ggcc

AY651061: E1:

gtcggagtgcgcaactcttcgggggtgtaccatgtcaccaatgattgccccaatgcgtctgttgtgtacgagacagatagcttgat
catacatctgccggggtgtgtgccctgcgtacgcgagggcaacggttcgaggtgctgggtctcccttagtcctactgttg
ccgctaaggatccgggcgtcccggtcaacgagattcggcgtcacgtcgacctgattgccggggccgctgcattctgttcg
gctatgtatgtagggcacttatgcggttccatcttcctcgttggccagcttttcaccctctcccctaggcgccactggacaacacaa Fig. 9 continued AY651061: E1 gactgtaattgctccatctacccaggacatgtgacaggccatcgaatggcttgggacatgatgatgaactggtcccctacgac
ggcgctggtagtagcccagctgctccggatcccacaagccatcttggacatgatcgctggtgctcactggggagtcctgg
cgggcatagcgtatttctccatggtggggaactggacgaaggtcctggtagtgctgctgctatttgccggcgtcgacgcg

AY651061: E2/NS1:

acgaccatcgtctccggggaagtgccggccgcagcacggctggacttgttgggctcttctcaccaggcgcccggcagaa
catccagctgatcaacaccaacggcagttggcacatcaaccgcacggccctgaactgcaatgataccccttcaaaccggct
gggtagcagggcttttctataccaacaaattcaactcttcgggttgccccgagaggttggccagctgccgaccccttgcc
gactttgaccagggctggggccctatcagttataccaacggaagcggccccgaccaacgcccctactgctggcactaccc
cccaaaaccttgtggtattgtgcccgcagagagcgtgtgtggcccagtatactgcttcactcccagccccgtggtggtgg
gaacgaccgacaggtcgggcgcgcccacctacaactggggtgaaaatgaaacggacgttttcgtcctcaacaacaccagg
ccacggctgggcaattggttcggtggtacctggatgaactcaactggattcaccaaggtgtgcggagcgccccttgtgc
catcggagggtgggcaacaacaccttgtactgccccactgattgtttccgcaaacatccggaagccacgtactctcggt
gcggctccggtccttggattacacccaggtgcttgatccactacccgtataggctttggcattatccttgtaccatcaat
tacaccatattcaagatcaggatgtttgtgggcggggttgagcacaggctcgacgccgcgtgcaactggacgcggggaga
gcgctgcgacttggacgacagggatcgggccgagttgagccctctgttgctgtccactacgcaatggcaggtcctcccct
gctcattcacaacactgcccgccctgtcaactggcctgatacatctccaccagaacatcgtggacgtgcagtacctctat
gggttgagctcggcagtcacatcctgggtcataaagtgggagtacgttgtgctcctcttcttgctgctagcagatgctcg
catttgtgcctgcttgtggatgatgcttctcatatctcaggtagaggcggcgctggagaacttgatagttctcaacgctgcttccta
gtcgggacacatggcatcgtccccttcttcatctttttttgtgcagcttggtacctaaaaggcaagtgggcccctggactcgcctatt
ccgtctatgggatgtggccactgctcctgcttctcctggcgttgccccaacgggcatacgcc

AY651061: NS2:

ttggatcaggagttggccgcgtcgtgtggggccacggtcttcatctgcctagcggtgctcactctatcgccatattacaaac
agtacatggcccgcggcatctggtggctgcagtacatgctgaccagagcagaggcgctcctacaggtttgggtcccccg
ctcaacgcccgaggagggcgcgacggagtcgtactgctcacgtgtgtgctccacccgcacttgctctttgaaatcaccaa
gatcatgctggccattctcgggcctttgtggatcttgcaggccagtctgctcaaggtaccgtacttcgtgcgcgttcagg
gccttctccggatctgcgcgctagcgcggaagatggtcggaggccattacgtgcaaatggtcaccatcaagttaggggcg
ctcactggcacctatatttataaccatctcactcctcttcgggactgggcgcacaacggcttgcaagacctagccgtagc
tgtggagccagtcgtcttctcccaaatggagaccaagctcatcacgtgggggggcagacacagccgcgtgtggtgacatca
tcaacggcttgcccgtctccgcccgcagg

AY651061: NS3:

ggccaggagatactgctcggaccagccgatggaatggcctctaggggatggaggttgctggcgcccatcacggcgtacgct
cagcagacaagggggcctcctagggtgtataatcaccagcctgactggccgggacaagaaccaagtggagggtgaagtcca
gattgtgtcaactgctgcccaaacgttcttggcgacgtgcatcaacggggtatgctggactgtctaccacggggccggaaccag
gaccattgcatcatccaaggtcctgttattctaatgtataccaatgtagaccaagacctcgggggctggaccgctcctcaagtgc
tcggctcactgacaccctggagctgcggctcctcggacctttaccggtcacgaggcatgccgatgtcattcccgtgccgcggc
gaggtgaaaccaggggcagcctgctttcgccccggcccatttcctatctaaagggatcctcgggaggccccctgctctgtccca
tgggacatgccgtgggcatttcagggccgcggtgtgcacccgtggggtcgcaaaggcggtcgactttgtgcccgttgagtc
cttagagaccaccatgaggtccccagtgtttactgacaattccagccctctaacagtgccccagagttaccaggtggcgcatcta
catgcacccactgggagtggcaagagcacgaaggtgccggccgcttacgcagctcaggggtacaaggtacttgtgctgaacc
cgtctgttgctgccaccttaggggttcggtgcttatatgtcaaaggcccatgggatcgacccaaacatcaggaccggcgtgagg Fig. 9 continued AY651061: NS3 accatcaccacaggctcccccatcacctactccacctacggcaaattttttggctgatggcggatgcccaggaggtgcgtacgac
atcataatatgtgacgaatgtcactcagtggacgccacctcgattctgggcatagggaccgtcttggaccaagcggagacggcg
ggggtcaggctcactgtcctcgccaccgctacaccacctggttccgtcaccgtgccacattccaacatcgaggaagttgcactgt
ccgctgacggggaaataccattttatggtaaggccatccccctaaactacatcaaggggggggaggcacctcattttctgccactc
caagaagaagtgcgacgagctcgctgcaaagctggtcggtccgggcgtcaacgcggtggccttttaccgtggcctcgacgta
tctgtcattccaactacaggagacgtcgttgttgtagcgaccgacgccttgatgactggcttcaccggagatttcgactctgtgata
gactgcaacacctgtgtcgtccagacagtcgacttcagcctagaccctatattctctattgagacttccaccgtgccccagga
cgccgtgtcccgctcccaacggagggggtaggaccggtcgagggaagcatggtatttacagatatgtgtcacccggggagc
ggccgtctggcatgttcgactccgtggtcctctgtgagtgctatgacgcgggttgtgcttggtacgagcttacacccgcc
gagaccacagtcaggctacgggcatacctcaacaccccaggattgcccgtgtgccaggaccacttggagttctgggagag
tgtcttcaccggcctcacccacatagatgcccacttcctgtcccagacgaaacagagtggggagaacttcccctacctag
tcgcataccaagccaccgtgtgcgctagagctagagctcctcccccgtcatgggaccaaatgtggaagtgcctgatacgg
ctcaagcccaccctcactgggggctaccccattactatacagactgggtagtgtacagaatgagatcaccttaacacaccc
aatcacccaatacatcatggcttgcatgtcggcggacctggaggtcgtcact

AY651061: NS4:

agcacgtgggtgttggtgggcggcgtcctagccgctttggccgcttactgcctgtccacaggcagcgtggtcatagtgggcagg
ataatcctaggtggggaagccggcagtcatacctgacaggggaggttctctaccgagagtttgatgagatggaggagtgcgccgc
ccacgtcccctacctcgagcaggggatgcatttggcggagcagttcaagcagaaagctcttgggttgctccagacggcatccaa
acaaacagagacgatcactcccattgtccagtctaattggcagaagctcgagtctttctgggctaaacacatgtggaacttcgtta
gcgggatacaatatctggcgggcctatcaacgctgcccgggaaccccgctatagcatcgctgatgtcgtttacggccgcag
tgacgagtccactaaccactcagcagaccctcctctttaacatcttgggggggtggctggctgcccagcttgccgcccca
gccgccgccacagccttcgttggcgcaggcattactggcgccgttgttggcagtgtgggcctagggaaggtcctggtgga
cattcttgccggctacggggctggtgtggccggggccctcgtggctttcaaaatgatgagcggggagaccccaccacgg
aggatctagtcaaccttctgcctgccatcctatcgccaggagctctcgttgtcgccgtggtgtgcgcagcaatactacgccggca
cgtgggccttggcgagggcgccgtgcagtggatgaaccggctgatagcgtttgcttctcgggtaaccacgtctcccctacaca
ctacgtgccggagagcgacgcgtcggctcgtgtcacaccaattctcaccaggctcactgttactcagcttctgaaagggctccac
gtgtggataagctcgaattgcatcgccccgtgt

AY651061: NS5:

gct agttcttggc ttaaagatgt ctggaactgg atatgcgagg
 tgctgagcga cttcaagaat tggctgaagg ccaaacttgt accacaactg cccgggatcc
 cattcgtatc ctgccaacgc gggtaccgtg gggtctggcg gggcgagggc atcgtgcaca
 ctcgttgccc gtgtggggcc aatataactg gacatgtcaa gaacggttcg atgagaatcg
 tcgggcctaa gacttgcagc aacacctggc gtgggtcgtt ccccattaac gcttacacta
 caggcccgtg cacgccctcc ccggcgccga actatacgtt cgcgctatgg aggggtgtctg
 cagaggagta tgtggaggta aggcggctgg gggacttcca ttacgtcacg ggggtgacca
 ctgataaact caagtgtcca tgccaggtcc cctcaccccga gttctccaca gaggtggacg
 gggtgcgcct gcataggtac gcccctcctt gcaaaccct gctacgggat gaggtgacgt
 ttagcgtcgg gttcaatgaa tacctggtgg ggtcccagtt gcctgcgag cccgagccag
 acgtagcagc attaacatca atgcttacag acccttccca catcactgca aagacggcgg
 cgcgtaggct gaagcggggg tctcccccct ccctggccag ttcttctgcc agccagctgt Fig. 9 continued AY651061: NS5 ccgcgccgtc actgaaagca acatgcacca ctcaccatga ctctccagac gccgacctca
tagaagccaa cctcctgtgg agacgggaga tgggggggaa catcaccaga gtggagtcgg
agaacaagat tgttgttctg gattctttcg acccgctcgt ggcagaggag gatgaccggg
agatttctat tccagctgag attctgcgga aatttaagca gtttcccccc gccatgccca
tatgggcacg gccggattat aatcctcccc ttgtggaacc gtggaagcgc ccggactgtg
atccacccct agtccacggg tgccccctac cacctcccaa gccgactccg gtgccgccac
cccggaaaaa gaggacggtg gtgctggacg agtctacagt atcatctgct ctggctgagc
ttgccactaa gaccttcggc agctctacaa cctcaggcgt gacaagtggt gaagcggccg
aatcgtcccc ggcgctttcc tgcgacggtg agctggactc cgaagctgaa tcttactcct
ccatgccccc tctcgagggg gaaccggggg accccgatct cagcgacggg tcttggtcta
ccgtgagcag tgatggcggt acggaggatg tcgtgtgctg ctcgatgtcc tactcgtgga
cgggcgcctt aattacgccc tgtgccgcag aggaaaccaa actccccatc aacgcactga
gtaactcgct gctgcgccac cacaatttgg tgtattccac cacctctcgc agcgctggca
agaggcagaa aaaagtcaca tttgacaggc tgcaggtcct ggacgatcat taccgggacg
tgctcaagga ggctaaggcc aaggcatcca cagtgaaggc taaattgcta tccgtagagg
aggcatgtag cctgacgccc ccgcactccg ccagatcaaa atttggctat gggccgaagg
atgtccgaag ccattccagt aaggctatac gccacatcaa ctccgtgtgg caggaccttc
tggaggacaa tacaacacct atagacacta ccatcatggc caagaatgaa gtcttctgcg
tgaaggccga aaaaggggggt cgcaagcccg ctcgccttat cgtgtacccc gacctggggg
tgcgcgtgtg cgagaagaga gctttgtatg acgtagtcaa acagctcccc attgccgtga
tgggaccctc ctacggggtc cagtactcgc cagcgcagcg ggtcgacttc ctgcttaacg
cgtggaaatc aaagaaaaac cctatggggt tttcctatga cacccgttgc tttgactcaa
cagtcactga ggctgatatc cgtacggagg aagacctcta tcaatcttgt gacctggtcc
ctgaggcccg cgcggccata aggtctctca cagagaggct ttacatcggg ggcccactta
ccaattctaa gggacaaaac tgcggctatc ggcgatgccg cgcaagcggc gtgctgacca
ctagctgcgg taacaccata acttgctacc ttaaggctag tgcggcctgt cgagctgcaa
agctccagga ctgcaccatg ctcgtgtgcg gcgacgacct cgtcgttatc tgtgaaagcg
ccggtgtcaa ggaggacgct gcgagcctga gagccttcac cgaggctatg accaggtact
ccggcccccc gggagacccg gctcaaccag aatacgactt ggagcttata acatcctgct
cctccaatgt gtcggtcgcg cgcgacggcg ctggccaaag ggtctattat ctgacccgtg
aacctgagac tccctcgcg cgtgccgctt gggagacagc aagacacact ccagtgaact
cctggctagg caacatcatc atgtttgccc ccactctgtg ggtacggatg gtcctcatga
cccacttatt ctccatactc atagttcagg agcaccttga aaaggctcta gattgtgaaa
tctatggagc cacacactcc gtcccaccgt tggacctacc tgaaatcatt caaagactcc
atggcctcag cgcgttttcg ctccacagtt actctccagg tgaaatcaat agggtggctt
catgcctcag gaaacttggg gttccaccct tgcgagcttg gagacaccgg gccggagcg
tccgcgccac actcctatcc cagggggga aagccgccat atgcggtaag tacctcttca Fig. 9 continued AY651061: NS5 actgggcggt gaaaaccaaa ctcaaactca ttccattacc gctcgcgtct catttggact
tgtccaattg gttcacgggc ggctacagcg ggggagacat ttatcacagc gtgtctcatg
cccggccccg ttggtttctc tggtgcctac tcctactctc agtaggggta ggcatctacc
tccttcccaa ccga

AY651061: 3` UTR:

tagacg gttgggcaac cactccaggc ctttaggccc tatttaaaca
ctccaggcct ttaggccccg t

AY651061 CORE:

```
atgagcacgaatcctaaacctcaaagaaaaaccaaacgtaacaccaaccgtcgcccacag
 M  S  T  N  P  K  P  Q  R  K  T  K  R  N  T  N  R  R  P  Q
gacgtcaagttcccggggtggcggacagatcgttggtggagtttacttgttgccgcgcagg
 D  V  K  F  P  G  G  G  Q  I  V  G  G  V  Y  L  L  P  R  R
ggccctagattgggtgtgcgcgcgacgaggaagacttccgagcggtcgcaacctcgaggt
 G  P  R  L  G  V  R  A  T  R  K  T  S  E  R  S  Q  P  R  G
agacgtcagcctatccccaaggcacgtcggcccgagggcaggacctgggctcagcccggg
 R  R  Q  P  I  P  K  A  R  R  P  E  G  R  T  W  A  Q  P  G
tacccttggcccctctatggcaatgagggctgcggggtgggcgggatggctcctgtctccc
 Y  P  W  P  L  Y  G  N  E  G  C  G  W  A  G  W  L  L  S  P
cgcggctctcggcctagttggggcccccacagaccccggcgtagatcgcgcaatttgggt
 R  G  S  R  P  S  W  G  P  T  D  P  R  R  R  S  R  N  L  G
aaggtcatcgataccctttacgtatggcttcgccgacctcatgggtacataccgctcgtc
 K  V  I  D  T  L  T  Y  G  F  A  D  L  M  G  Y  I  P  L  V
ggcgccccccttggggggcgctgccagggccctggcgcacggcgtccgggtcctggaagac
 G  A  P  L  G  G  A  A  R  A  L  A  H  G  V  R  V  L  E  D
ggcgtgaactatgcaacagggaaccttcctggttgctctttctctatcttccttctggcc
 G  V  N  Y  A  T  G  N  L  P  G  C  S  F  S  I  F  L  L  A
ctgctctcttgcttgactgtgcccgcttcggcc
 L  L  S  C  L  T  V  P  A  S  A
```

AY651061 E1:

```
gtcggagtgcgcaactcttcgggggtgtaccatgtcaccaatgattgccccaatgcgtct
 V  G  V  R  N  S  S  G  V  Y  H  V  T  N  D  C  P  N  A  S
gttgtgtacgagacagatagcttgatcatacatctgccggggtgtgtgccctgcgtacgc
 V  V  Y  E  T  D  S  L  I  I  H  L  P  G  C  V  P  C  V  R
gagggcaacggttcgaggtgctgggtctcccttagtcctactgttgccgctaaggatccg
 E  G  N  G  S  R  C  W  V  S  L  P  T  V  A  A  K  D  P
ggcgtcccggtcaacgagattcggcgtcacgtcgacctgattgccggggccgctgcattc
 G  V  P  V  N  E  I  R  R  H  V  D  L  I  A  G  A  A  F
tgttcggctatgtatgtagggcacttatgcggttccatcttcctcgttggccagcttttc
 C  S  A  M  Y  V  G  H  L  C  G  S  I  F  L  V  G  Q  L  F
accctctcccctaggcgccactggacaacacaagactgtaattgctccatctacccagga
 T  L  S  P  R  R  H  W  T  T  Q  D  C  N  C  S  I  Y  P  G
catgtgacaggccatcgaatggcttgggacatgatgatgaactggtcccctacgacggcg
 H  V  T  G  H  R  M  A  W  D  M  M  M  N  W  S  P  T  T  A
```

Fig. 9 continued AY651061 E1

```
ctggtagtagcccagctgctccggatcccacaagccatcttggacatgatcgctggtgct
 L  V  V  A  Q  L  L  R  I  P  Q  A  I  L  D  M  I  A  G  A
cactggggagtcctggcgggcatagcgtatttctccatggtggggaactggacgaaggtc
 H  W  G  V  L  A  G  I  A  Y  F  S  M  V  G  N  W  T  K  V
ctggtagtgctgctgctatttgccggcgtcgacgcg
 L  V  V  L  L  L  F  A  G  V  D  A
```

VGVRNSSGVYHVTNDCPNASVVYETDSLIIHLPGCVPCVREGNGSRCWVSLSPTVAAKDP
GVPVNEIRRHVDLIAGAAAFCSAMYVGHLCGSIFLVGQLFTLSPRRHWTTQDCNCSIYPG
HVTGHRMAWDMMMNWSPTTALVVAQLLRIPQAILDMIAGAHWGVLAGIAYFSMVGNWTKV
LVVLLLFAGVDA

AY651061 E2/NS1:

```
acgaccatcgtctccggggggaagtgccggccgcagcacggctggacttgttgggctcttc
 T  T  I  V  S  G  G  S  A  G  R  S  T  A  G  L  V  G  L  F
tcaccaggcgcccggcagaacatccagctgatcaacaccaacggcagttggcacatcaac
 S  P  G  A  R  Q  N  I  Q  L  I  N  T  N  G  S  W  H  I  N
cgcacggccctgaactgcaatgatacccttcaaaccggctgggtagcagggcttttctat
 R  T  A  L  N  C  N  D  T  L  Q  T  G  W  V  A  G  L  F  Y
accaacaaattcaactcttcggggttgccccgagaggttggccagctgccgaccccttgcc
 T  N  K  F  N  S  S  G  C  P  E  R  L  A  S  C  R  P  L  A
gactttgaccagggctggggccctatcagttataccaacggaagcggccccgaccaacgc
 D  F  D  Q  G  W  G  P  I  S  Y  T  N  G  S  G  P  D  Q  R
ccctactgctggcactaccccccaaaaccttgtggtattgtgcccgcagagagcgtgtgt
 P  Y  C  W  H  Y  P  P  K  P  C  G  I  V  P  A  E  S  V  C
ggcccagtatactgcttcactcccagccccgtggtggtgggaacgaccgacaggtcgggc
 G  P  V  Y  C  F  T  P  S  P  V  V  V  G  T  T  D  R  S  G
gcgcccacctacaactggggtgaaaatgaaacggacgttttcgtcctcaacaacaccagg
 A  P  T  Y  N  W  G  E  N  E  T  D  V  F  V  L  N  N  T  R
ccacggctgggcaattggttcggtggtacctggatgaactcaactggattcaccaaggtg
 P  R  L  G  N  W  F  G  G  T  W  M  N  S  T  G  F  T  K  V
tgcggagcgccccctctgtgccatcggagggggtgggcaacaacaccttgtactgccccact
 C  G  A  P  P  C  A  I  G  G  V  G  N  N  T  L  Y  C  P  T
gattgtttccgcaaacatccggaagccacgtactctcggtgcggctccggtccttggatt
 D  C  F  R  K  H  P  E  A  T  Y  S  R  C  G  S  G  P  W  I
acacccaggtgcttgatccactacccgtataggctttggcattatccttgtaccatcaat
 T  P  R  C  L  I  H  Y  P  Y  R  L  W  H  Y  P  C  T  I  N
tacaccatattcaagatcaggatgtttgtgggcggggttgagcacaggctcgacgccgcg
 Y  T  I  F  K  I  R  M  F  V  G  G  V  E  H  R  L  D  A  A
tgcaactggacgcggggagagcgctgcgacttggacgacagggatcgggccgagttgagc
 C  N  W  T  R  G  E  R  C  D  L  D  D  R  D  R  A  E  L  S
cctctgttgctgtccactacgcaatggcaggtcctcccctgctcattcacaacactgccc
 P  L  L  L  S  T  T  Q  W  Q  V  L  P  C  S  F  T  T  L  P
gccctgtcaactggcctgatacatctccaccagaacatcgtggacgtgcagtacctctat
 A  L  S  T  G  L  I  H  L  H  Q  N  I  V  D  V  Q  Y  L  Y
gggttgagctcggcagtcacatcctgggtcataaagtgggagtacgttgtgctcctcttc
 G  L  S  S  A  V  T  S  W  V  I  K  W  E  Y  V  V  L  L  F
ttgctgctagcagatgctcgcatttgtgcctgcttgtggatgatgcttctcatatctcag
 L  L  L  A  D  A  R  I  C  A  C  L  W  M  M  L  L  I  S  Q
gtagaggcggcgctggagaacttgatagttctcaacgctgcttccctagtcgggacacat
 V  E  A  A  L  E  N  L  I  V  L  N  A  A  S  L  V  G  T  H
```

Fig. 9 continued AY651061 E2/NS1

```
ggcatcgtccccttcttcatctttttttgtgcagcttggtacctaaaaggcaagtgggcc
 G  I  V  P  F  F  I  F  F  C  A  A  W  Y  L  K  G  K  W  A
cctggactcgcctattccgtctatgggatgtggccactgctcctgcttctcctggcgttg
 P  G  L  A  Y  S  V  Y  G  M  W  P  L  L  L  L  L  A  L
ccccaacgggcatacgcc
 P  Q  R  A  Y  A
```

TTIVSGGSAGRSTAGLVGLFSPGARQNIQLINTNGSWHINRTALNCNDTLQTGWVAGLFY
TNKFNSSGCPERLASCRPLADFDQGWGPISYTNGSGPDQRPYCWHYPPKPCGIVPAESVC
GPVYCFTPSPVVVGTTDRSGAPTYNWGENETDVFVLNNTRPRLGNWFGGTWMNSTGFTKV
CGAPPCAIGGVGNNTLYCPTDCFRKHPEATYSRCGSGPWITPRCLIHYPYRLWHYPCTIN
YTIFKIRMFVGGVEHRLDAACNWTRGERCDLDDRDRAELSPLLLSTTQWQVLPCSFTTLP
ALSTGLIHLHQNIVDVQYLYGLSSAVTSWVIKWEYVVLLFLLLADARICACLWMMLLISQ
VEAALENLIVLNAASLVGTHGIVPFFIFFCAAWYLKGKWAPGLAYSVYGMWPLLLLLLAL
PQRAYA

AY651061 NS2:

```
ttggatcaggagttggccgcgtcgtgtggggccacggtcttcatctgcctagcggtgctc
 L  D  Q  E  L  A  A  S  C  G  A  T  V  F  I  C  L  A  V  L
actctatcgccatattacaaacagtacatggcccgcggcatctggtggctgcagtacatg
 T  L  S  P  Y  Y  K  Q  Y  M  A  R  G  I  W  W  L  Q  Y  M
ctgaccagagcagaggcgctcctacaggtttgggtccccccgctcaacgcccgaggaggg
 L  T  R  A  E  A  L  L  Q  V  W  V  P  P  L  N  A  R  G  G
cgcgacggagtcgtactgctcacgtgtgtgctccacccgcacttgctctttgaaatcacc
 R  D  G  V  V  L  L  T  C  V  L  H  P  H  L  L  F  E  I  T
aagatcatgctggccattctcgggcctttgtggatcttgcaggccagtctgctcaaggta
 K  I  M  L  A  I  L  G  P  L  W  I  L  Q  A  S  L  L  K  V
ccgtacttcgtgcgcgttcagggccttctccggatctgcgcgctagcgcggaagatggtc
 P  Y  F  V  R  V  Q  G  L  L  R  I  C  A  L  A  R  K  M  V
ggaggccattacgtgcaaatggtcaccatcaagttaggggcgctcactggcacctatatt
 G  G  H  Y  V  Q  M  V  T  I  K  L  G  A  L  T  G  T  Y  I
tataaccatctcactcctcttcgggactgggcgcacaacggcttgcaagacctagccgta
 Y  N  H  L  T  P  L  R  D  W  A  H  N  G  L  Q  D  L  A  V
gctgtggagccagtcgtcttctcccaaatggagaccaagctcatcacgtggggggcagac
 A  V  E  P  V  V  F  S  Q  M  E  T  K  L  I  T  W  G  A  D
acagccgcgtgtggtgacatcatcaacggcttgcccgtctccgcccgcagg
 T  A  A  C  G  D  I  I  N  G  L  P  V  S  A  R  R
```

LDQELAASCGATVFICLAVLTLSPYYKQYMARGIWWLQYMLTRAEALLQVWVPPLNARGG
RDGVVLLTCVLHPHLLFEITKIMLAILGPLWILQASLLKVPYFVRVQGLLRICALARKMV
GGHYVQMVTIKLGALTGTYIYNHLTPLRDWAHNGLQDLAVAVEPVVFSQMETKLITWGAD
TAACGDIINGLPVSARR

AY651061 NS3:

Fig. 9 continued AY651061 NS3

```
ggccaggagatactgctcggaccagccgatggaatggcctctaggggatggaggttgctg
 G  Q  E  I  L  L  G  P  A  D  G  M  A  S  R  G  W  R  L  L
gcgcccatcacggcgtacgctcagcagacaaggggcctcctagggtgtataatcaccagc
 A  P  I  T  A  Y  A  Q  Q  T  R  G  L  L  G  I  I  T  S
ctgactggccgggacaagaaccaagtggagggtgaagtccagattgtgtcaactgctgcc
 L  T  G  R  D  K  N  Q  V  E  G  E  V  Q  I  V  S  T  A  A
caaacgttcttggcgacgtgcatcaacggggtatgctggactgtctaccacggggccgga
 Q  T  F  L  A  T  C  I  N  G  V  C  W  T  V  Y  H  G  A  G
accaggaccattgcatcatccaagggtcctgttattctaatgtataccaatgtagaccaa
 T  R  T  I  A  S  S  K  G  P  V  I  L  M  Y  T  N  V  D  Q
gacctcgggggctggaccgctcctcaagtgctcggctcactgacaccctggagctgcggc
 D  L  G  G  W  T  A  P  Q  V  L  G  S  L  T  P  W  S  C  G
tcctcggacctttacctggtcacgaggcatgccgatgtcattcccgtgccgcggcgaggt
 S  S  D  L  Y  L  V  T  R  H  A  D  V  I  P  V  P  R  R  G
gaaaccaggggcagcctgctttcgccccggcccatttcctatctaaagggatcctcggga
 E  T  R  G  S  L  L  S  P  R  P  I  S  Y  L  K  G  S  S  G
ggccccctgctctgtcccatgggacatgccgtgggcattttcagggccgcggtgtgcacc
 G  P  L  L  C  P  M  G  H  A  V  G  I  F  R  A  A  V  C  T
cgtggggtcgcaaaggcggtcgactttgtgcccgttgagtccttagagaccaccatgagg
 R  G  V  A  K  A  V  D  F  V  P  V  E  S  L  E  T  T  M  R
tccccagtgtttactgacaattccagccctctaacagtgccccagagttaccaggtggcg
 S  P  V  F  T  D  N  S  S  P  L  T  V  P  Q  S  Y  Q  V  A
catctacatgcacccactgggagtggcaagagcacgaaggtgccggccgcttacgcagct
 H  L  H  A  P  T  G  S  G  K  S  T  K  V  P  A  A  Y  A  A
caggggtacaaggtacttgtgctgaacccgtctgttgctgccaccttagggttcggtgct
 Q  G  Y  K  V  L  V  L  N  P  S  V  A  A  T  L  G  F  G  A
tatatgtcaaaggcccatgggatcgacccaaacatcaggaccggcgtgaggaccatcacc
 Y  M  S  K  A  H  G  I  D  P  N  I  R  T  G  V  R  T  I  T
acaggctcccccatcaccctactccacctacggcaaatttttggctgatggcggatgccca
 T  G  S  P  I  T  Y  S  T  Y  G  K  F  L  A  D  G  G  C  P
ggaggtgcgtacgacatcataatatgtgacgaatgtcactcagtggacgccacctcgatt
 G  G  A  Y  D  I  I  I  C  D  E  C  H  S  V  D  A  T  S  I
ctgggcatagggaccgtcttggaccaagcggagacggcgggggtcaggctcactgtcctc
 L  G  I  G  T  V  L  D  Q  A  E  T  A  G  V  R  L  T  V  L
gccaccgctacaccacctggttccgtcaccgtgccacattccaacatcgaggaagttgca
 A  T  A  T  P  P  G  S  V  T  V  P  H  S  N  I  E  E  V  A
ctgtccgctgacggggaaataccatttatggtaaggccatccccctaaactacatcaag
 L  S  A  D  G  E  I  P  F  Y  G  K  A  I  P  L  N  Y  I  K
ggggggaggcacctcatttctgccactccaagaagaagtgcgacgagctcgctgcaaag
 G  G  R  H  L  I  F  C  H  S  K  K  C  D  E  L  A  A  K
ctggtcggtccgggcgtcaacgcggtggccttttaccgtggcctcgacgtatctgtcatt
 L  V  G  P  G  V  N  A  V  A  F  Y  R  G  L  D  V  S  V  I
ccaactacaggagacgtcgttgttgtagcgaccgacgccttgatgactggcttcaccgga
 P  T  T  G  D  V  V  V  V  A  T  D  A  L  M  T  G  F  T  G
gatttcgactctgtgatagactgcaacaccctgtgtcgtccagacagtcgacttcagccta
 D  F  D  S  V  I  D  C  N  T  C  V  V  Q  T  V  D  F  S  L
gacccttatattctctattgagacttccaccgtgccccaggacgccgtgtcccgctcccaa
 D  P  I  F  S  I  E  T  S  T  V  P  Q  D  A  V  S  R  S  Q
cggagggggtaggaccggtcgagggaagcatggtatttacagatatgtgtcacccggggag
 R  R  G  R  T  G  R  G  K  H  G  I  Y  R  Y  V  S  P  G  E
cggccgtctggcatgttcgactccgtggtcctctgtgagtgctatgacgcgggttgtgct
 R  P  S  G  M  F  D  S  V  V  L  C  E  C  Y  D  A  G  C  A
tggtacgagcttacacccgccgagaccacagtcaggctacgggcatacctcaacacccca
 W  Y  E  L  T  P  A  E  T  T  V  R  L  R  A  Y  L  N  T  P
ggattgcccgtgtgccaggaccacttggagttctgggagagtgtcttcaccggcctcacc
 G  L  P  V  C  Q  D  H  L  E  F  W  E  S  V  F  T  G  L  T
```

Fig. 9 continued AY651061 NS3

```
cacatagatgcccacttcctgtcccagacgaaacagagtggggagaacttcccctaccta
 H  I  D  A  H  F  L  S  Q  T  K  Q  S  G  E  N  F  P  Y  L
gtcgcataccaagccaccgtgtgcgctagagctagagctcctccccgtcatgggaccaa
 V  A  Y  Q  A  T  V  C  A  R  A  R  A  P  P  P  S  W  D  Q
atgtggaagtgcctgatacggctcaagcccaccctcactggggctacccattactatac
 M  W  K  C  L  I  R  L  K  P  T  L  T  G  A  T  P  L  L  Y
agactgggtagtgtacagaatgagatcaccttaacacacccaatcacccaatacatcatg
 R  L  G  S  V  Q  N  E  I  T  L  T  H  P  I  T  Q  Y  I  M
gcttgcatgtcggcggacctggaggtcgtcact
 A  C  M  S  A  D  L  E  V  V  T
```

GQEILLGPADGMASRGWRLLAPITAYAQQTRGLLGCIITSLTGRDKNQVEGEVQIVSTAA
QTFLATCINGVCWTVYHGAGTRTIASSKGPVILMYTNVDQDLGGWTAPQVLGSLTPWSCG
SSDLYLVTRHADVIPVPRRGETRGSLLSPRPISYLKGSSGGPLLCPMGHAVGIFRAAVCT
RGVAKAVDFVPVESLETTMRSPVFTDNSSPLTVPQSYQVAHLHAPTGSGKSTKVPAAYAA
QGYKVLVLNPSVAATLGFGAYMSKAHGIDPNIRTGVRTITTGSPITYSTYGKFLADGGCP
GGAYDIIICDECHSVDATSILGIGTVLDQAETAGVRLTVLATATPPGSVTVPHSNIEEVA
LSADGEIPFYGKAIPLNYIKGGRHLIFCHSKKKCDELAAKLVGPGVNAVAFYRGLDVSVI
PTTGDVVVVATDALMTGFTGDFDSVIDCNTCVVQTVDFSLDPIFSIETSTVPQDAVSRSQ
RRGRTGRGKHGIYRYVSPGERPSGMFDSVVLCECYDAGCAWYELTPAETTVRLRAYLNTP
GLPVCQDHLEFWESVFTGLTHIDAHFLSQTKQSGENFPYLVAYQATVCARARAPPPSWDQ
MWKCLIRLKPTLTGATPLLYRLGSVQNEITLTHPITQYIMACMSADLEVVT

AY651061 NS4:

```
agcacgtgggtgttggtgggcggcgtcctagccgctttggccgcttactgcctgtccaca
 S  T  W  V  L  V  G  G  V  L  A  A  L  A  A  Y  C  L  S  T
ggcagcgtggtcatagtgggcaggataatcctaggtgggaagccggcagtcatacctgac
 G  S  V  V  I  V  G  R  I  I  L  G  G  K  P  A  V  I  P  D
agggaggttctctaccgagagtttgatgagatggaggagtgcgccgcccacgtcccctac
 R  E  V  L  Y  R  E  F  D  E  M  E  E  C  A  A  H  V  P  Y
ctcgagcaggggatgcatttggcggagcagttcaagcagaaagctcttggggttgctccag
 L  E  Q  G  M  H  L  A  E  Q  F  K  Q  K  A  L  G  L  L  Q
acggcatccaaacaaacagagacgatcactcccattgtccagtctaattggcagaagctc
 T  A  S  K  Q  T  E  T  I  T  P  I  V  Q  S  N  W  Q  K  L
gagtctttctgggctaaacacatgtggaacttcgttagcgggatacaatatctggcgggc
 E  S  F  W  A  K  H  M  W  N  F  V  S  G  I  Q  Y  L  A  G
ctatcaacgctgcccgggaaccccgctatagcatcgctgatgtcgtttacggccgcagtg
 L  S  T  L  P  G  N  P  A  I  A  S  L  M  S  F  T  A  V
acgagtccactaaccactcagcagaccctcctctttaacatcttgggggggtggctggct
 T  S  P  L  T  T  Q  Q  T  L  L  F  N  I  L  G  G  W  L  A
gcccagcttgccgccccagccgccgccacagccttcgttggcgcaggcattactggcgcc
 A  Q  L  A  A  P  A  A  A  T  F  V  G  A  G  I  T  G  A
gttgttggcagtgtgggcctagggaaggtcctggtggacattcttgccggctacggggct
 V  V  G  S  V  G  L  G  K  V  L  V  D  I  L  A  G  Y  G  A
ggtgtggccggggccctcgtggctttcaaaatcatgagcggggagaccccccaccacggag
 G  V  A  G  A  L  V  A  F  K  I  M  S  G  E  T  P  T  E
gatctagtcaaccttctgcctgccatcctatcgccaggagctctcgttgtcgccgtggtg
```

Fig. 9 continued AY651061 NS4

```
         D  L  V  N  L  L  P  A  I  L  S  P  G  A  L  V  V  A  V  V
tgcgcagcaatactacgccggcacgtgggccttggcgagggcgccgtgcagtggatgaac
         C  A  A  I  L  R  R  H  V  G  L  G  E  G  A  V  Q  W  M  N
cggctgatagcgtttgcttctcggggtaaccacgtctcccctacacactacgtgccggag
         R  L  I  A  F  A  S  R  G  N  H  V  S  P  T  H  Y  V  P  E
agcgacgcgtcggctcgtgtcacaccaattctcaccaggctcactgttactcagcttctg
         S  D  A  S  A  R  V  T  P  I  L  T  R  L  T  V  T  Q  L  L
aaagggctccacgtgtggataagctcgaattgcatcgccccgtgt
         K  G  L  H  V  W  I  S  S  N  C  I  A  P  C
```

STWVLVGGVLAALAAYCLSTGSVVIVGRIILGGKPAVIPDREVLYREFDEMEECAAHVPY
LEQGMHLAEQFKQKALGLLQTASKQTETITPIVQSNWQKLESFWAKHMWNFVSGIQYLAG
LSTLPGNPAIASLMSFTAAVTSPLTTQQTLLFNILGGWLAAQLAAPAAATAFVGAGITGA
VVGSVGLGKVLVDILAGYGAGVAGALVAFKIMSGETPTTEDLVNLLPAILSPGALVVAVV
CAAILRRHVGLGEGAVQWMNRLIAFASRGNHVSPTHYVPESDASARVTPILTRLTVTQLL
KGLHVWISSNCIAPC

AY651061 NS5 :

```
gctagttcttggcttaaagatgtctggaactggatatgcgaggtgctgagcgacttcaag
         A  S  S  W  L  K  D  V  W  N  W  I  C  E  V  L  S  D  F  K
aattggctgaaggccaaacttgtaccacaactgcccgggatcccattcgtatcctgccaa
         N  W  L  K  A  K  L  V  P  Q  L  P  G  I  P  F  V  S  C  Q
cgcgggtaccgtggggtctggcggggcgagggcatcgtgcacactcgttgcccgtgtggg
         R  G  Y  R  G  V  W  R  G  E  G  I  V  H  T  R  C  P  C  G
gccaatataactggacatgtcaagaacggttcgatgagaatcgtcgggcctaagacttgc
         A  N  I  T  G  H  V  K  N  G  S  M  R  I  V  G  P  K  T  C
agcaacacctggcgtggggtcgttccccattaacgcttacactacaggcccgtgcacgccc
         S  N  T  W  R  G  S  F  P  I  N  A  Y  T  T  G  P  C  T  P
tccccggcgccgaactatacgttcgcgctatggagggtgtctgcagaggagtatgtggag
         S  P  A  P  N  Y  T  F  A  L  W  R  V  S  A  E  E  Y  V  E
gtaaggcggctgggggacttccattacgtcacgggggtgaccactgataaactcaagtgt
         V  R  R  L  G  D  F  H  Y  V  T  G  V  T  T  D  K  L  K  C
ccatgccaggtcccctcacccgagttctccacagaggtggacggggtgcgcctgcatagg
         P  C  Q  V  P  S  P  E  F  S  T  E  V  D  G  V  R  L  H  R
tacgcccctccctgcaaacccctgctacgggatgaggtgacgtttagcgtcgggttcaat
         Y  A  P  P  C  K  P  L  L  R  D  E  V  T  F  S  V  G  F  N
gaatacctggtggggtcccagttgccctgcgagcccgagccagacgtagcagcattaaca
         E  Y  L  V  G  S  Q  L  P  C  E  P  E  P  D  V  A  A  L  T
tcaatgcttacagaccccttcccacatcactgcaaagacggcggcgcgtaggctgaagcgg
         S  M  L  T  D  P  S  H  I  T  A  K  T  A  A  R  R  L  K  R
gggtctccccctccctggccagttcttctgccagccagctgtccgcgccgtcactgaaa
         G  S  P  P  S  L  A  S  S  S  A  S  Q  L  S  A  P  S  L  K
gcaacatgcaccactcaccatgactctccagacgccgacctcatagaagccaacctcctg
         A  T  C  T  T  H  H  D  S  P  D  A  D  L  I  E  A  N  L  L
tggagacgggagatggggggggaacatcaccagagtggagtcggagaacaagattgttgtt
         W  R  R  E  M  G  G  N  I  T  R  V  E  S  E  N  K  I  V  V
ctggattctttcgacccgctcgtggcagaggaggatgaccgggagatttctattccagct
         L  D  S  F  D  P  L  V  A  E  E  D  D  R  E  I  S  I  P  A
gagattctgcggaaatttaagcagtttccccccgccatgcccatatgggcacggccggat
         E  I  L  R  K  F  K  Q  F  P  P  A  M  P  I  W  A  R  P  D
```

Fig. 9 continued AY651061 NS5

```
tataatcctcccccttgtggaaccgtggaagcgcccggactgtgatccacccttagtccac
 Y  N  P  P  L  V  E  P  W  K  R  P  D  C  D  P  P  L  V  H
gggtgccccctaccacctcccaagccgactccggtgccgccacccggaaaaagaggacg
 G  C  P  L  P  P  P  K  P  T  P  V  P  P  P  R  K  K  R  T
gtggtgctggacgagtctacagtatcatctgctctggctgagcttgccactaagaccttc
 V  V  L  D  E  S  T  V  S  S  A  L  A  E  L  A  T  K  T  F
ggcagctctacaacctcaggcgtgacaagtggtgaagcggccgaatcgtccccggcgctt
 G  S  S  T  T  S  G  V  T  S  G  E  A  A  E  S  P  A  L
tcctgcgacggtgagctggactccgaagctgaatcttactcctccatgccccctctcgag
 S  C  D  G  E  L  D  S  E  A  E  S  Y  S  S  M  P  P  L  E
ggggaaccgggggaccccgatctcagcgacgggtcttggtctaccgtgagcagtgatggc
 G  E  P  G  D  P  D  L  S  D  G  S  W  S  T  V  S  S  D  G
ggtacggaggatgtcgtgtgctgctcgatgtcctactcgtggacgggcgccttaattacg
 G  T  E  D  V  V  C  C  S  M  S  Y  S  W  T  G  A  L  I  T
ccctgtgccgcagaggaaaccaaactccccatcaacgcactgagtaactcgctgctgcgc
 P  C  A  A  E  E  T  K  L  P  I  N  A  L  S  N  L  L  R
caccacaatttggtgtattccaccacctctcgcagcgctggcaagaggcagaaaaagtc
 H  H  N  L  V  Y  S  T  T  S  R  S  A  G  K  R  Q  K  K  V
acatttgacaggctgcaggtcctggacgatcattaccgggacgtgctcaaggaggctaag
 T  F  D  R  L  Q  V  L  D  D  H  Y  R  D  V  L  K  E  A  K
gccaaggcatccacagtgaaggctaaattgctatccgtagaggaggcatgtagcctgacg
 A  K  A  S  T  V  K  A  K  L  L  S  V  E  E  A  C  S  L  T
cccccgcactccgccagatcaaaatttggctatgggccgaaggatgtccgaagccattcc
 P  P  H  S  A  R  S  K  F  G  Y  G  P  K  D  V  R  S  H  S
agtaaggctatacgccacatcaactccgtgtggcaggaccttctggaggacaatacaaca
 S  K  A  I  R  H  I  N  S  V  W  Q  D  L  L  E  D  N  T  T
cctatagacactaccatcatggccaagaatgaagtcttctgcgtgaaggccgaaaaaggg
 P  I  D  T  T  I  M  A  K  N  E  V  F  C  V  K  A  E  K  G
ggtcgcaagcccgctcgcccttatcgtgtaccccgacctgggggtgcgcgtgtgcgagaag
 G  R  K  P  A  R  L  I  V  Y  P  D  L  G  V  R  V  C  E  K
agagctttgtatgacgtagtcaaacagctcccccattgccgtgatgggaccctcctacggg
 R  A  L  Y  D  V  V  K  Q  L  P  I  A  V  M  G  P  S  Y  G
ttccagtactcgccagcgcagcgggtcgacttcctgcttaacgcgtggaaatcaaagaaa
 F  Q  Y  S  P  A  Q  R  V  D  F  L  L  N  A  W  K  S  K  K
aaccctatggggttttcctatgacacccgttgctttgactcaacagtcactgaggctgat
 N  P  M  G  F  S  Y  D  T  R  C  F  D  S  T  V  T  E  A  D
atccgtacggaggaagacctctatcaatcttgtgacctggtccctgaggcccgcgcggcc
 I  R  T  E  E  D  L  Y  Q  S  C  D  L  V  P  E  A  R  A  A
ataaggtctctcacagagaggcttacatcggggggcccacttaccaattctaagggacaa
 I  R  S  L  T  E  R  L  Y  I  G  G  P  L  T  N  S  K  G  Q
aactgcggctatcggcgatgccgcgcaagcggcgtgctgaccactagctgcggtaacacc
 N  C  G  Y  R  R  C  R  A  S  G  V  L  T  T  S  C  G  N  T
ataacttgctaccttaaggctagtgcggcctgtcgagctgcaaagctccaggactgcacc
 I  T  C  Y  L  K  A  S  A  A  C  R  A  A  K  L  Q  D  C  T
atgctcgtgtgcggcgacgacctcgtcgttatctgtgaaagcgccggtgtcaaggaggac
 M  L  V  C  G  D  D  L  V  V  I  C  E  S  A  G  V  K  E  D
gctgcgagcctgagagccttcaccgaggctatgaccaggtactccggcccccgggagac
 A  A  S  L  R  A  F  T  E  A  M  T  R  Y  S  G  P  P  G  D
ccggctcaaccagaatacgacttggagcttataacatcctgctcctccaatgtgtcggtc
 P  A  Q  P  E  Y  D  L  E  L  I  T  S  C  S  S  N  V  S  V
gcgcgcgacggcgctggccaaagggtctattatctgacccgtgaacctgagactcccctc
 A  R  D  G  A  G  Q  R  V  Y  Y  L  T  R  E  P  E  T  P  L
gcgcgtgccgcttgggagacagcaagacacactccagtgaactcctggctaggcaacatc
 A  R  A  A  W  E  T  A  R  H  T  P  V  N  S  W  L  G  N  I
atcatgtttgccccccactctgtgggtacggatggtcctcatgacccacttattctccata
 I  M  F  A  P  T  L  W  V  R  M  V  L  M  T  H  L  F  S  I
ctcatagttcaggagcaccttgaaaaggctctagattgtgaaatctatggagccacacac
```

Fig. 9 continued AY651061 NS5

```
         L   I   V   Q   E   H   L   E   K   A   L   D   C   E   I   Y   G   A   T   H
tccgtcccaccgttggacctacctgaaatcattcaaagactccatggcctcagcgcgttt
         S   V   P   P   L   D   L   P   E   I   I   Q   R   L   H   G   L   S   A   F
tcgctccacagttactctccaggtgaaatcaatagggtggcttcatgcctcaggaaactt
         S   L   H   S   Y   S   P   G   E   I   N   R   V   A   S   C   L   R   K   L
ggggttccaccettgcgagcttggagacaccgggcccggagcgtccgcgccacactccta
         G   V   P   P   L   R   A   W   R   H   R   A   R   S   V   R   A   T   L   L
tcccagggggggaaagccgccatatgcggtaagtacctcttcaactgggcggtgaaaacc
         S   Q   G   G   K   A   A   I   C   G   K   Y   L   F   N   W   A   V   K   T
aaactcaaactcattccattaccgctcgcgtctcatttggacttgtccaattggttcacg
         K   L   K   L   I   P   L   P   L   A   S   H   L   D   L   S   N   W   F   T
ggcggctacagcgggggagacatttatcacagcgtgtctcatgcccggccccgttggttt
         G   G   Y   S   G   G   D   I   Y   H   S   V   S   H   A   R   P   R   W   F
ctctggtgcctactcctactctcagtaggggtaggcatctacctccttcccaaccga
         L   W   C   L   L   L   S   V   G   V   G   I   Y   L   L   P   N   R
```

ASSWLKDVWNWICEVLSDFKNWLKAKLVPQLPGIPFVSCQRGYRGVWRGEGIVHTRCPCG
ANITGHVKNGSMRIVGPKTCSNTWRGSFPINAYTTGPCTPSPAPNYTFALWRVSAEEYVE
VRRLGDFHYVTGVTTDKLKCPCQVPSPEFSTEVDGVRLHRYAPPCKPLLRDEVTFSVGFN
EYLVGSQLPCEPEPDVAALTSMLTDPSHITAKTAARRLKRGSPPSLASSSASQLSAPSLK
ATCTTHHDSPDADLIEANLLWRREMGGNITRVESENKIVVLDSFDPLVAEEDDREISIPA
EILRKFKQFPPAMPIWARPDYNPPLVEPWKRPDCDPPLVHGCPLPPPKPTPVPPPRKKRT
VVLDESTVSSALAELATKTFGSSTTSGVTSGEAAESSPALSCDGELDSEAESYSSMPPLE
GEPGDPDLSDGSWSTVSSDGGTEDVVCCSMSYSWTGALITPCAAEETKLPINALSNSLLR
HHNLVYSTTSRSAGKRQKKVTFDRLQVLDDHYRDVLKEAKAKASTVKAKLLSVEEACSLT
PPHSARSKFGYGPKDVRSHSSKAIRHINSVWQDLLEDNTTPIDTTIMAKNEVFCVKAEKG
GRKPARLIVYPDLGVRVCEKRALYDVVKQLPIAVMGPSYGFQYSPAQRVDFLLNAWKSKK
NPMGFSYDTRCFDSTVTEADIRTEEDLYQSCDLVPEARAAIRSLTERLYIGGPLTNSKGQ
NCGYRRCRASGVLTTSCGNTITCYLKASAACRAAKLQDCTMLVCGDDLVVICESAGVKED
AASLRAFTEAMTRYSGPPGDPAQPEYDLELITSCSSNVSVARDGAGQRVYYLTREPETPL
ARAAWETARHTPVNSWLGNIIMFAPTLWVRMVLMTHLFSILIVQEHLEKALDCEIYGATH
SVPPLDLPEIIQRLHGLSAFSLHSYSPGEINRVASCLRKLGVPPLRAWRHRARSVRATLL
SQGGKAAICGKYLFNWAVKTKLKLIPLPLASHLDLSNWFTGGYSGGDIYHSVSHARPRWF
LWCLLLLSVGVGIYLLPNR

Fig. 10

SEQ ID No.2 translation="MSTNPKPQRKTKRNTNRRPQDVKFPGGGQIVGGVYLLPRRGPRL

GVRATRKTSERSQPRGRRQPIPKARRPEGRTWAQPGYPWPLYGNEGCGWAGWLLSPRG

SRPSWGPTDPRRRSRNLGKVIDTLTYGFADLMGYIPLVGAPLGGAARALAHGVRVLED

Fig. 10 continued SEQ ID No.2

GVNYATGNLPGCSFSIFLLALLSCLTVPASAVGVRNSSGVYHVTNDCPNASVVYETDS

LIIHLPGCVPCVREGNGSRCWVSLSPTVAAKDPGVPVNEIRRHVDLIAGAAAFCSAMY

VGHLCGSIFLVGQLFTLSPRRHWTTQDCNCSIYPGHVTGHRMAWDMMMNWSPTTALVV

AQLLRIPQAILDMIAGAHWGVLAGIAYFSMVGNWTKVLVVLLLFAGVDATTIVSGGSA

GRSTAGLVGLFSPGARQNIQLINTNGSWHINRTALNCNDTLQTGWVAGLFYTNKFNSS

GCPERLASCRPLADFDQGWGPISYTNGSGPDQRPYCWHYPPKPCGIVPAESVCGPVYC

FTPSPVVVGTTDRSGAPTYNWGENETDVFVLNNTRPRLGNWFGGTWMNSTGFTKVCGA

PPCAIGGVGNNTLYCPTDCFRKHPEATYSRCGSGPWITPRCLIHYPYRLWHYPCTINY

TIFKIRMFVGGVEHRLDAACNWTRGERCDLDDRDRAELSPLLLSTTQWQVLPCSFTTL

PALSTGLIHLHQNIVDVQYLYGLSSAVTSWVIKWEYVVLLFLLLADARICACLWMMLL

ISQVEAALENLIVLNAASLVGTHGIVPFFIFFCAAWYLKGKWAPGLAYSVYGMWPLLL

LLLALPQRAYALDQELAASCGATVFICLAVLTLSPYYKQYMARGIWWLQYMLTRAEAL

LQVWVPPLNARGGRDGVVLLTCVLHPHLLFEITKIMLAILGPLWILQASLLKVPYFVR

VQGLLRICALARKMVGGHYVQMVTIKLGALTGTYTYNHLTPLRDWAHNGLQDLAVAVE

PVVFSQMETKLITWGADTAACGDIINGLPVSARRGQEILLGPADGMASRGWRLLAPIT

AYAQQTRGLLGCIITSLTGRDKNQVEGEVQIVSTAAQTFLATCINGVCWTVYHGAGTR

TIASSKGPVILMYTNVDQDLGGWTAPQVLGSLTPWSCGSSDLYLVTRHADVIPVPRRG

ETRGSLLSPRPISYLKGSSGGPLLCPMGHAVGIFRAAVCTRGVAKAVDFVPVESLETT

MRSPVFTDNSSPLTVPQSYQVAHLHAPTGSGKSTKVPAAYAAQGYKVLVLNPSVAATL

GFGAYMSKAHGIDPNIRTGVRTITTGSPITYSTYGKFLADGGCPGGAYDIICDECHS

VDATSILGIGTVLDQAETAGVRLTVLATATPPGSVTVPHSNIEEVALSADGEIPFYGK

AIPLNYIKGGRHLIFCHSKKKCDELAAKLVGPGVNAVAFYRGLDVSVIPTTGDVVVVA

TDALMTGFTGDFDSVIDCNTCVVQTVDFSLDPIFSIETSTVPQDAVSRSQRRGRTGRG

KHGIYRYVSPGERPSGMFDSVVLCECYDAGCAWYELTPAETTVRLRAYLNTPGLPVCQ

Fig. 10 continued SEQ ID No.2

DHLEFWESVFTGLTHIDAHFLSQTKQSGENFPYLVAYQATVCARARAPPPSWDQMWKC
LIRLKPTLTGATPLLYRLGSVQNEITLTHPITQYIMACMSADLEVVTSTWVLVGGVLA
ALAAYCLSTGSVVIVGRIILGGKPAVIPDREVLYREFDEMEECAAHVPYLEQGMHLAE
QFKQKALGLLQTASKQTETITPIVQSNWQKLESFWAKHMWNFVSGIQYLAGLSTLPGN
PAIASLMSFTAAVTSPLTTQQTLLFNILGGWLAAQLAAPAAATAFVGAGITGAVVGSV
GLGKVLVDILAGYGAGVAGALVAFKIMSGETPTTEDLVNLLPAILSPGALVVAVVCAA
ILRRHVGLGEGAVQWMNRLIAFASRGNHVSPTHYVPESDASARVTPILTRLTVTQLLK
GLHVWISSNCIAPCASSWLKDVWNWICEVLSDFKNWLKAKLVPQLPGIPFVSCQRGYR
GVWRGEGIVHTRCPCGANITGHVKNGSMRIVGPKTCSNTWRGSFPINAYTTGPCTPSP
APNYTFALWRVSAEEYVEVRRLGDFHYVTGVTTDKLKCPCQVPSPEFSTEVDGVRLHR
YAPPCKPLLRDEVTFSVGFNEYLVGSQLPCEPEPDVAALTSMLTDPSHITAKTAARRL
KRGSPPSLASSSASQLSAPSLKATCTTHHDSPDADLIEANLLWRREMGGNITRVESEN
KIVVLDSFDPLVAEEDDREISIPAEILRKFKQFPPAMPIWARPDYNPPLVEPWKRPDC
DPPLVHGCPLPPPKPTPVPPPRKKRTVVLDESTVSSALAELATKTFGSSTTSGVTSGE
AAESSPALSCDGELDSEAESYSSMPPLEGEPGDPDLSDGSWSTVSSDGGTEDVVCCSM
SYSWTGALITPCAAEETKLPINALSNSLLRHHNLVYSTTSRSAGKRQKKVTFDRLQVL
DDHYRDVLKEAKAKASTVKAKLLSVEEACSLTPPHSARSKFGYGPKDVRSHSSKAIRH
INSVWQDLLEDNTTPIDTTIMAKNEVFCVKAEKGGRKPARLIVYPDLGVRVCEKRALY
DVVKQLPIAVMGPSYGFQYSPAQRVDFLLNAWKSKKNPMGFSYDTRCFDSTVTEADIR
TEEDLYQSCDLVPEARAAIRSLTERLYIGGPLTNSKGQNCGYRRCRASGVLTTSCGNT
ITCYLKASAACRAAKLQDCTMLVCGDDLVVICESAGVKEDAASLRAFTEAMTRYSGPP
GDPAQPEYDLELITSCSSNVSVARDGAGQRVYYLTREPETPLARAAWETARHTPVNSW
LGNIIMFAPTLWVRMVLMTHLFSILIVQEHLEKALDCEIYGATHSVPPLDLPEIIQRL
HGLSAFSLHSYSPGEINRVASCLRKLGVPPLRAWRHRARSVRATLLSQGGKAAICGKY
LFNWAVKTKLKLIPLPLASHLDLSNWFTGGYSGGDIYHSVSHARPRWFLWCLLLLSVG

Fig. 10 continued SEQ ID No.2

VGIYLLPNR"

SEQ ID No. 1

ORIGIN

```
   1 gccagccccc tgatgggggc gacactccgc catgaatcac tccoctgtga ggaactactg
  61 tcttcacgca gaaagcgtct agccatggcg ttagtatgag tgtcgtgcag cctccaggac
 121 cccccctccc gggagagcca tagtggtctg cggaaccggt gagtacaccg gaattgccag
 181 gacgaccggg tcctttcttg gataaacccg ctcaacgcct ggagatttgg gcgtgccccc
 241 gcaagactgc tagccgagta gtgttgggtc gcgaaaggcc ttgtggtact gcctgatagg
 301 gtgcttgcga gtgccccggg aggtctcgta gaccgtgcac catgagcacg aatcctaaac
 361 ctcaaagaaa aaccaaacgt aacaccaacc gtcgcccaca ggacgtcaag ttcccgggtg
 421 gcggacagat cgttggtgga gtttacttgt tgccgcgcag gggccctaga ttgggtgtgc
 481 gcgcgacgag gaagacttcc gagcggtcgc aacctcgagg tagacgtcag cctatcccca
 541 aggcacgtcg gcccgagggc aggacctggg ctcagcccgg gtaccttgg cccctctatg
 601 gcaatgaggg ctgcgggtgg gcgggatggc tcctgtctcc ccgcggctct cggcctagtt
 661 ggggccccac agaccccgg cgtagatcgc gcaatttggg taaggtcatc gatacccta
 721 cgtatggctt cgccgacctc atggggtaca taccgctcgt cggcgccccc cttggggggcg
 781 ctgccagggc cctggcgcac ggcgtccggg tcctggaaga cggcgtgaac tatgcaacag
 841 ggaaccttcc tggttgctct ttctctatct tccttctggc cctgctctct tgcttgactg
 901 tgcccgcttc ggccgtcgga gtgcgcaact cttcgggggt gtaccatgtc accaatgatt
 961 gcccaatgc gtctgttgtg tacgagacag atagcttgat catacatctg ccggggtgtg
1021 tgccctgcgt acgcgagggc aacggttcga ggtgctgggt ctcccttagt cctactgttg
1081 ccgctaagga tccggccgtc ccggtcaacg agattcggcg tcacgtcgac ctgattgccg
1141 gggccgctgc attctgttcg gctatgtatg tagggcactt atgcggttcc atcttcctcg
1201 ttggccagct tttcacccc tcccctaggc gccactggac aacacaagac tgtaattgct
1261 ccatctaccc aggacatgtg acaggccatc gaatggcttg ggacatgatg atgaactggt
1321 cccctacgac ggcgctggta gtagcccagc tgctccggat cccacaagcc atcttggaca
1381 tgatcgctgg tgctcactgg ggagtcctgg cgggcatagc gtatttctcc atggtgggga
1441 actggacgaa ggtcctggta gtgctgctgc tatttgccgg cgtcgacgcg acgaccatcg
1501 tctccggggg aagtgccggc cgcagcacgg ctggacttgt tgggctcttc tcaccaggcg
1561 cccggcagaa catccagctg atcaacacca acggcagttg gcacatcaac cgcacggccc
1621 tgaactgcaa tgatacccct caaaccggct gggtagcagg gcttttctat accaacaaat
1681 tcaactcttc ggggttgccc gagaggttgg ccagctgccg accccttgcc gactttgacc
1741 agggctgggg ccctatcagt tataccaacg gaagcggccc cgaccaacgc ccctactgct
1801 ggcactaccc cccaaaacct tgtggtattg tgcccgcaga gagcgtgtgt ggcccagtat
1861 actgcttcac tcccagcccc gtggtggtgg gaacgaccga caggtcgggc gcgcccacct
1921 acaactgggg tgaaaatgaa acggacgttt cgtcctcaa caacaccagg ccacggctgg
1981 gcaattggtt cggtggtacc tggatgaact caactggatt caccaaggtg tgcggagcgc
2041 cccttgtgc catcggaggg gtgggcaaca acaccttgta ctgccccact gattgtttcc
2101 gcaaacatcc ggaagccacg tactctcggt gcggctccgg tccttggatt acacccaggt
2161 gcttgatcca ctacccgtat aggctttggc attatccttg taccatcaat tacaccatat
2221 tcaagatcag gatgtttgtg ggcggggttg agcacaggct cgacgccgcg tgcaactgga
2281 cgcgggagg agcgctgcgac ttggacgaca gggatcgggc cgagttgagc cctctgttgc
2341 tgtccactac gcaatggcag gtcctccct gtcattcac aacactgcc gccctgtcaa
2401 ctggcctgat acatctccac cagaacatcg tggacgtgca gtacctctat gggttgagct
2461 cggcagtcac atcctgggtc ataaagtggg agtacgttgt gctcctcttc ttgctgctag
2521 cagatgctcg catttgtgcc tgcttgtgga tgatgcttct catatctcag gtagaggcgg
```

Fig. 10 continued  SEQ ID No.1

```
2581 cgctggagaa cttgatagtt ctcaacgctg cttccctagt cgggacacat ggcatcgtcc
2641 ccttcttcat cttttttgt gcagcttggt acctaaaagg caagtgggcc cctggactcg
2701 cctattccgt ctatgggatg tggccactgc tcctgcttct cctggcgttg ccccaacggg
2761 catacgcctt ggatcaggag ttggccgcgt cgtgtggggc cacggtcttc atctgcctag
2821 cggtgctcac tctatcgcca tattacaaac agtacatggc ccgcggcatc tggtggctgc
2881 agtacatgct gaccagagca gaggcgctcc tacaggtttg ggtccccccg ctcaacgccc
2941 gaggagggcg cgacggagtc gtactgctca cgtgtgtgct ccacccgcac ttgctctttg
3001 aaatcaccaa gatcatgctg gccattctcg ggcctttgtg gatcttgcag gccagtctgc
3061 tcaaggtacc gtacttcgtg cgcgttcagg gccttctccg gatctgcgcg ctagcgcgga
3121 agatggtcgg aggccattac gtgcaaatgg tcaccatcaa gttaggggcg ctcactggca
3181 cctatattta taaccatctc actcctcttc gggactgggc gcaaacggc ttgcaagacc
3241 tagccgtagc tgtggagcca gtcgtcttct cccaaatgga gaccaagctc atcacgtggg
3301 gggcagacac agccgcgtgt ggtgacatca tcaacggctt gcccgtctcc gcccgcaggg
3361 gccaggagat actgctcgga ccagccgatg gaatgccctc taggggatgg aggttgctgg
3421 cgcccatcac ggcgtacgct cagcagacaa ggggcctcct agggtgtata atcaccagcc
3481 tgactggccg ggacaagaac caagtggagg gtgaagtcca gattgtgtca actgctgccc
3541 aaacgttctt ggcgacgtgc atcaacgggg tatgctggac tgtctaccac ggggccggaa
3601 ccaggaccat tgcatcatcc aagggtcctg ttattctaat gtataccaat gtagaccaag
3661 acctcggggg ctggaccgct cctcaagtgc tcggctcact gacaccctgg agctgcggct
3721 cctcggacct ttacctggtc acgaggcatg ccgatgtcat tcccgtgccg cggcgaggtg
3781 aaaccagggg cagcctgctt tcgccccggc ccatttccta tctaaaggga tcctcgggag
3841 gccccctgct ctgtccatg ggacatgccg tgggcatttt cagggccgcg gtgtgcaccc
3901 gtggggtcgc aaaggcggtc gactttgtgc ccgttgagtc cttagagacc accatgaggt
3961 ccccagtgtt tactgacaat tccagccctc taacagtgcc ccagagttac caggtggcgc
4021 atctacatgc acccactggg agtggcaaga gcacgaaggt gccggccgct tacgcagctc
4081 aggggtacaa ggtacttgtg ctgaacccgt ctgttgctgc caccttaggg ttcggtgctt
4141 atatgtcaaa ggcccatggg atcgacccaa acatcaggac cggcgtgagg accatcacca
4201 caggctcccc catcacctac tccacctacg gcaaattttt ggctgatggc ggatgcccag
4261 gaggtgcgta cgacatcata atatgtgacg aatgtcactc agtggacgcc acctcgattc
4321 tgggcatagg gaccgtcttg gaccaagcgg agacggcggg ggtcaggctc actgtcctcg
4381 ccaccgctac accacctggt tccgtcaccg tgccacattc caacatcgag gaagttgcac
4441 tgtccgctga cgggggaaata ccattttatg gtaaggccat cccctaaac tacatcaagg
4501 gggggaggca cctcattttc tgccactcca agaagaagtg cgacgagctc gctgcaaagc
4561 tggtcggtcc gggcgtcaac gcggtggcct tttaccgtgg cctcgacgta tctgtcattc
4621 caactacagg agacgtcgtt gttgtagcga ccgacgcctt gatgactggc ttcaccggag
4681 atttcgactc tgtgatagac tgcaacacct gtgtcgtcca gacagtcgac ttcagcctag
4741 accctatatt ctctattgag acttccaccg tgccccagga cgccgtgtcc cgctcccaac
4801 ggagggggtag gaccggtcga gggaagcatg gtatttacag atatgtgtca cccggggagc
4861 ggccgtctgg catgttcgac tccgtggtcc tctgtgagtg ctatgacgcg ggttgtgctt
4921 ggtacgagct tacacccgcc gagaccacag tcaggctacg ggcatacctc aacacccag
4981 gattgcccgt gtgccaggac cacttggagt ctgggagag tgtcttcacc ggcctcaccc
5041 acatagatgc ccacttcctg tcccagacga aacagagtgg ggagaacttc cctacctag
5101 tcgcatacca agccaccgtg tgcgctagag ctagagctcc tcccccgtca tgggaccaaa
5161 tgtggaagtg cctgatacgg ctcaagccca ccctcactgg ggctacccca ttactataca
5221 gactgggtag tgtacagaat gagatcacct taacacaccc aatcacccaa tacatcatgg
5281 cttgcatgtc ggcggacctg gaggtcgtca ctagcacgtg ggtgttggtg ggcggcgtcc
```

Fig. 10 continued SEQ ID No.1

```
5341 tagccgcttt ggccgcttac tgcctgtcca caggcagcgt ggtcatagtg ggcaggataa
5401 tcctaggtgg gaagccggca gtcataccctg acagggaggt tctctaccga gagtttgatg
5461 agatggagga gtgcgccgcc cacgtcccct acctcgagca ggggatgcat ttggcggagc
5521 agttcaagca gaaagctctt gggttgctcc agacggcatc caaacaaaca gagacgatca
5581 ctcccattgt ccagtctaat tggcagaagc tcgagtcttt ctgggctaaa cacatgtgga
5641 acttcgttag cgggatacaa tatctggcgg gcctatcaac gctgcccggg aaccccgcta
5701 tagcatcgct gatgtcgttt acggccgcag tgacgagtcc actaaccact cagcagaccc
5761 tcctctttaa catcttgggg gggtggctgg ctcccagct tgccgcccca gccgccgcca
5821 cagccttcgt tggcgcaggc attactggcg ccgttgttgg cagtgtgggc ctagggaagg
5881 tcctggtgga cattcttgcc ggctacgggg ctggtgtggc cggggccctc gtggctttca
5941 aaatcatgag cggggagacc cccaccacgg aggatctagt caaccttctg cctgccatcc
6001 tatcgccagg agctctcgtt gtcgccgtgg tgtgcgcagc aatactacgc cggcacgtgg
6061 gccttggcga gggcgccgtg cagtggatga accggctgat agcgtttgct tctcggggta
6121 accacgtctc ccctacacac tacgtgccgg agagcgacgc gtcggctcgt gtcacaccaa
6181 ttctcaccag gctcactgtt actcagcttc tgaaagggct ccacgtgtgg ataagctcga
6241 attgcatcgc cccgtgtgct agttcttggc ttaaagatgt ctggaactgg atatgcgagg
6301 tgctgagcga cttcaagaat tggctgaagg ccaaacttgt accacaactg cccgggatcc
6361 cattcgtatc ctgccaacgc gggtaccgtg gggtctggcg gggcgagggc atcgtgcaca
6421 ctcgttgccc gtgtggggcc aatataactg gacatgtcaa gaacggttcg atgagaatcg
6481 tcgggcctaa gacttgcagc aacacctggc gtgggtcgtt ccccattaac gcttacacta
6541 caggcccgtg cacgccctcc ccggcgccga actatacgtt cgcgctatgg agggtgtctg
6601 cagaggagta tgtggaggta aggcggctgg gggacttcca ttacgtcacg ggggtgacca
6661 ctgataaact caagtgtcca tgccaggtcc cctcacccga gttctccaca gaggtggacg
6721 gggtgcgcct gcataggtac gcccctccct gcaaacccct gctacgggat gaggtgacgt
6781 ttagcgtcgg gttcaatgaa tacctggtgg ggtcccagtt gccctgcgag cccgagccag
6841 acgtagcagc attaacatca atgcttacag acccttccca catcactgca agacggcgg
6901 cgcgtaggct gaagcggggg tctcccccct ccctggccag ttcttctgcc agccagctgt
6961 ccgcgccgtc actgaaagca acatgcacca ctcaccatga ctctccagac gccgacctca
7021 tagaagccaa cctcctgtgg agacgggaga tgggggggaa catcaccaga gtggagtcgg
7081 agaacaagat tgttgttctg gattctttcg acccgctcgt ggcagaggag gatgaccggg
7141 agatttctat tccagctgag attctgcgga aatttaagca gtttccccccc gccatgccca
7201 tatgggcacg gccggattat aatcctcccc ttgtggaacc gtggaagcgc ccggactgtg
7261 atccaccctt agtccacggg tgcccctac cacctcccaa gccgactccg gtgccgccac
7321 cccggaaaaa gaggacggtg gtgctggacg agtctacagt atcatctgct ctggctgagc
7381 ttgccactaa gaccttcggc agctctacaa cctcaggcgt gacaagtggt gaagcggccg
7441 aatcgtcccc ggcgctttcc tgcgacggtg agctggactc cgaagctgaa tcttactcct
7501 ccatgccccc tctcgagggg gaaccggggg accccgatct cagcgacggg tcttggtcta
7561 ccgtgagcag tgatggcggt acggaggatg tcgtgtgctg ctcgatgtcc tactcgtgga
7621 cgggcgcctt aattacgccc tgtgccgcag aggaaaccaa actccccatc aacgcactga
7681 gtaactcgct gctgcgccac cacaatttgg tgtattccac cacctctcgc agcgctggca
7741 agaggcagaa aaaagtcaca tttgacaggc tgcaggtcct ggacgatcat taccgggacg
7801 tgctcaagga ggctaaggcc aaggcatcca cagtgaaggc taaattgcta tccgtagagg
7861 aggcatgtag cctgacgccc ccgcactccg ccagatcaaa atttggctat gggccgaagg
7921 atgtccgaag ccattccagt aaggctatac gccacatcaa ctccgtgtgg caggaccttc
7981 tggaggacaa tacaacacct atagacacta ccatcatggc caagaatgaa gtcttctgcg
8041 tgaaggccga aaaaggggt cgcaagcccg ctcgccttat cgtgtacccc gacctggggg
```

Fig. 10 continued SEQ ID No.1

8101 tgcgcgtgtg cgagaagaga gctttgtatg acgtagtcaa acagctcccc attgccgtga
8161 tgggaccctc ctacggggttc cagtactcgc cagcgcagcg ggtcgacttc ctgcttaacg
8221 cgtggaaatc aaagaaaaac cctatgggggt tttcctatga cacccgttgc tttgactcaa
8281 cagtcactga ggctgatatc cgtacggagg aagacctcta tcaatcttgt gacctggtcc
8341 ctgaggcccg cgcggccata aggtctctca cagagaggct ttacatcggg ggcccactta
8401 ccaattctaa gggacaaaac tgcggctatc ggcgatgccg cgcaagcggc gtgctgacca
8461 ctagctgcgg taacaccata acttgctacc ttaaggctag tgcggcctgt cgagctgcaa
8521 agctccagga ctgcaccatg ctcgtgtgcg gcgacgacct cgtcgttatc tgtgaaagcg
8581 ccggtgtcaa ggaggacgct gcgagcctga gagccttcac cgaggctatg accaggtact
8641 ccggcccccc gggagacccg gctcaaccag aatacgactt ggagcttata acatcctgct
8701 cctccaatgt gtcggtcgcg cgcgacggcg ctggccaaag ggtctattat ctgacccgtg
8761 aacctgagac tcccctcgcg cgtgccgctt gggagacagc aagacacact ccagtgaact
8821 cctggctagg caacatcatc atgtttgccc ccactctgtg ggtacggatg gtcctcatga
8881 cccacttatt ctccatactc atagttcagg agcaccttga aaaggctcta gattgtgaaa
8941 tctatggagc cacacactcc gtcccaccgt tggacctacc tgaaatcatt caaagactcc
9001 atggcctcag cgcgtttttcg ctccacagtt actctccagg tgaaatcaat agggtggctt
9061 catgcctcag gaaacttggg gttccaccct tgcgagcttg gagacaccgg gcccggagcg
9121 tccgcgccac actcctatcc caggggggga aagccgccat atgcggtaag tacctcttca
9181 actgggcggt gaaaaccaaa ctcaaactca ttccattacc gctcgcgtct catttggact
9241 tgtccaattg gttcacgggc ggctacagcg ggggagacat ttatcacagc gtgtctcatg
9301 cccggcccccg ttggtttctc tggtgcctac tcctactctc agtaggggta ggcatctacc
9361 tccttcccaa ccgatagacg gttgggcaac cactccaggc ctttaggccc tatttaaaca
9421 ctccaggcct ttaggccccg t Fig: 11

```
              10          20          30          40          50          60
HCV1    GCCAGCCCCCTGATGGGGGCGACACTCCACCATGAATCACTCCCCTGTGAGGAACTACTG
        ::::::::::::::::::::::::::::::: ::::::::::::::::::::::::::::
AY6510  GCCAGCCCCCTGATGGGGGCGACACTCCGCCATGAATCACTCCCCTGTGAGGAACTACTG
              10          20          30          40          50          60

70          80          90         100         110         120
HCV1    TCTTCACGCAGAAAGCGTCTAGCCATGGCGTTAGTATGAGTGTCGTGCAGCCTCCAGGAC
        ::::::::::::::::::::::::::::::::::::::::::::::::::::::::::::
AY6510  TCTTCACGCAGAAAGCGTCTAGCCATGGCGTTAGTATGAGTGTCGTGCAGCCTCCAGGAC
              70          80          90         100         110         120

130         140         150         160         170         180
HCV1    CCCCCCTCCCGGGAGAGCCATAGTGGTCTGCGGAACCGGTGAGTACACCGGAATTGCCAG
        ::::::::::::::::::::::::::::::::::::::::::::::::::::::::::::
AY6510  CCCCCCTCCCGGGAGAGCCATAGTGGTCTGCGGAACCGGTGAGTACACCGGAATTGCCAG
             130         140         150         160         170         180

190         200         210         220         230         240
HCV1    GACGACCGGGTCCTTTCTTGGATCAACCCGCTCAATGCCTGGAGATTTGGGCGTGCCCCC
        :::::::::::::::::::::::::: :::::::::: ::::::::::::::::::::::
AY6510  GACGACCGGGTCCTTTCTTGGATAAACCCGCTCAACGCCTGGAGATTTGGGCGTGCCCCC
             190         200         210         220         230         240

250         260         270         280         290         300
```

Fig. 11 continued

```
HCV1    GCAAGACTGCTAGCCGAGTAGTGTTGGGTCGCGAAAGGCCTTGTGGTACTGCCTGATAGG
        ::::::::::::::::::::::::::::::::::::::::::::::::::::::::::::
AY6510  GCAAGACTGCTAGCCGAGTAGTGTTGGGTCGCGAAAGGCCTTGTGGTACTGCCTGATAGG
            250       260       270       280       290       300

310       320       330       340
HCV1    GTGCTTGCGAGTGCCCCGGGAGGTCTCGTAGACCGTGCACC
        ::::::::::::::::::::::::::::::::::::::::
AY6510  GTGCTTGCGAGTGCCCCGGGAGGTCTCGTAGACCGTGCACC
            310       320       330       340
```

Fig: 12

```
            10        20        30        40        50        60
HCV1    ATGAGCACGAATCCTAAACCTCAAAAAAAAAACAAACGTAACACCAACCGTCGCCCACAG
        ::::::::::::::::::::::::::::::       :::::::::::::::::::::::
AY6510  ATGAGCACGAATCCTAAACCTCAAAGAAAAACCAAACGTAACACCAACCGTCGCCCACAG
            10        20        30        40        50        60

70        80        90       100       110       120
HCV1    GACGTCAAGTTCCCGGGTGGCGGTCAGATCGTTGGTGGAGTTTACTTGTTGCCGCGCAGG
        ::::::::::::::::::::::::::   :::::::::::::::::::::::::::::::
AY6510  GACGTCAAGTTCCCGGGTGGCGGACAGATCGTTGGTGGAGTTTACTTGTTGCCGCGCAGG
            70        80        90       100       110       120

130       140       150       160       170       180
HCV1    GGCCCTAGATTGGGTGTGCGCGCGACGAGAAAGACTTCCGAGCGGTCGCAACCTCGAGGT
        ::::::::::::::::::::::::::::::::: ::::::::::::::::::::::::::
AY6510  GGCCCTAGATTGGGTGTGCGCGCGACGAGGAAGACTTCCGAGCGGTCGCAACCTCGAGGT
            130       140       150       160       170       180

190       200       210       220       230       240
HCV1    AGACGTCAGCCTATCCCCAAGGCTCGTCGGCCCGAGGGCAGGACCTGGGCTCAGCCCGGG
        ::::::::::::::::::::::::  ::::::::::::::::::::::::::::::::::
AY6510  AGACGTCAGCCTATCCCCAAGGCACGTCGGCCCGAGGGCAGGACCTGGGCTCAGCCCGGG
            190       200       210       220       230       240

250       260       270       280       290       300
HCV1    TACCCTTGGCCCCTCTATGGCAATGAGGGCTGCGGGTGGGCGGGATGGCTCCTGTCTCCC
        ::::::::::::::::::::::::::::::::::::::::::::::::::::::::::::
AY6510  TACCCTTGGCCCCTCTATGGCAATGAGGGCTGCGGGTGGGCGGGATGGCTCCTGTCTCCC
            250       260       270       280       290       300

310       320       330       340       350       360
HCV1    CGTGGCTCTCGGCCTAGCTGGGGCCCCACAGACCCCCGGCGTAGGTCGCGCAATTTGGGT
        ::  ::::::::::::::::: ::::::::::::::::::::::::    ::::::::::
AY6510  CGCGGCTCTCGGCCTAGTTGGGGCCCCACAGACCCCCGGCGTAGATCGCGCAATTTGGGT
            310       320       330       340       350       360

370       380       390       400       410       420
HCV1    AAGGTCATCGATACCCTTACGTGCGGCTTCGCCGACCTCATGGGGTACATACCGCTCGTC
        ::::::::::::::::::::::::      ::::::::::::::::::::::::::::::
AY6510  AAGGTCATCGATACCCTTACGTATGGCTTCGCCGACCTCATGGGGTACATACCGCTCGTC
            370       380       390       400       410       420

430       440       450       460       470       480
HCV1    GGCGCCCCTCTTGGAGGCGCTGCCAGGGCCCTGGCGCATGGCGTCCGGGTTCTGGAAGAC
```

Fig. 12 continued

```
        : : : : : : : : :    : : : : :    : : : : : : : : : : : : : : : : : : :    : : : : : : : : : : :    : : : : : : : : : :
AY6510  GGCGCCCCCCTTGGGGGCGCTGCCAGGGCCCTGGCGCACGGCGTCCGGGTCCTGGAAGAC
            430       440       450       460       470       480

490       500       510       520       530       540
HCV1    GGCGTGAACTATGCAACAGGGAACCTTCCTGGTTGCTCTTTCTCTATCTTCCTTCTGGCC
        : : : : : : : : : : : : : : : : : : : : : : : : : : : : : : : : : : : : : : : : : : : : : : : : : : : : : : : : : : : : :
AY6510  GGCGTGAACTATGCAACAGGGAACCTTCCTGGTTGCTCTTTCTCTATCTTCCTTCTGGCC
             490       500       510       520       530       540

550       560       570
HCV1    CTGCTCTCTTGCTTGACTGTGCCCGCTTCGGCC
        : : : : : : : : : : : : : : : : : : : : : : : : : : : : : : :
AY6510  CTGCTCTCTTGCTTGACTGTGCCCGCTTCGGCC
             550       560       570
```

FIG: 13

```
             10        20        30        40        50        60
HCV1    AGTGCGCAACTCCACGGGGCTTTACCACGTCACCAATGATTGCCCTAACTCGAGTATTGT
        : : : : : : : : : :    : : : : :    : : : : : : : : : : : : : : : : : : :    : :    : :    :  : : : :
AY6510  AGTGCGCAACTCTTCGGGGGTGTACCATGTCACCAATGATTGCCCCAATGCGTCTGTTGT
             10        20        30        40        50        60

70        80        90       100       110       120
HCV1    GTACGAGGCGGCCGATGCCATCCTGCACACTCCGGGGTGCGTCCCTTGCGTTCGTGAGGG
        : : : : : : :  : :           : : :   :   : :      : : : : : : : : :  : :    : :    : : : : :  : :    : : : : :
AY6510  GTACGAGACAGATAGCTTGATCATACATCTGCCGGGGTGTGTGCCCTGCGTACGCGAGGG
             70        80        90       100       110       120

130       140       150       160       170       180
HCV1    CAACGCCTCGAGGTGTTGGGTGGCGATGACCCCTACGGTGGCCACCAGGGATGGCAAACT
        : : : : :    : : : : : : : :    : : : : :      :    :  :    : : : : :   : :   : : :    :  :    : : : :              :
AY6510  CAACGGTTCGAGGTGCTGGGTCTCCCTTAGTCCTACTGTTGCCGCTAAGGATCCGGGCGT
            130       140       150       160       170       180

190       200       210       220       230       240
HCV1    CCCCG-CGACGCAGCTTCGACGTCACATCGATCTGCTTGTCGGGAGCGCCACCCTCTGTT
        : : :    :    :    : : :    : :    : : : :    : : : : : :    : : : :    : : :    : : :    : : : :      : : :      :    : : : : : :
AY6510  CCCGGTCAACG-AGATTCGGCGTCACGTCGACCTGATTGCCGGGGCCGCTGCATTCTGTT
            190       200       210       220       230       240

250       260       270       280       290       300
HCV1    CGGCCCTCTACGTGGGGGACCTATGCGGGTCTGTCTTTCTTGTCGGCCAACTGTTCACCT
        : : : :    :    : :. : :    : : :    : :    : : : : : : : :    : :      : : : :    : :    : :    : : : : :    : :    : : : : : :
AY6510  CGGCTATGTATGTAGGGCACTTATGCGGTTCCATCTTCCTCGTTGGCCAGCTTTTCACCC
            250       260       270       280       290       300

310       320       330       340       350       360
HCV1    TCTCTCCCAGGCGCCACTGGACGACGCAAGGTTGCAATTGCTCTATCTATCCCGGCCATA
        : : : :    : : : : : : : : : : : : : : : :   : :    : : : :      : :    : : : : : : : : :      : : : : :    : :    : :    : : :
AY6510  TCTCCCCTAGGCGCCACTGGACAACACAAGACTGTAATTGCTCCATCTACCCAGGACATG
            310       320       330       340       350       360
```

Fig. 13 continued

```
              370       380       390       400       410       420
   HCV1    TAACGGGTCACCGCATGGCATGGGATATGATGATGAACTGGTCCCCTACGACGGCGTTGG
           :  ::  ::  :: ::  :::::  :::::  :::::::::::::::::::::::  :::
   AY6510  TGACAGGCCATCGAATGGCTTGGGACATGATGATGAACTGGTCCCCTACGACGGCGCTGG
              370       380       390       400       410       420

430       440       450       460       470       480
   HCV1    TAATGGCTCAGCTGCTCCGGATCCCACAAGCCATCTTGGACATGATCGCTGGTGCTCACT
           ::  :  ::  :::::::::::::::::::::::::::::::::::::::::::::::::
   AY6510  TAGTAGCCCAGCTGCTCCGGATCCCACAAGCCATCTTGGACATGATCGCTGGTGCTCACT
              430       440       450       460       470       480

490       500       510       520       530       540
   HCV1    GGGGAGTCCTGGCGGGCATAGCGTATTTCTCCATGGTGGGGAACTGGGCGAAGGTCCTGG
           ::::::::::::::::::::::::::::::::::::::::::::::::  ::::::::::
   AY6510  GGGGAGTCCTGGCGGGCATAGCGTATTTCTCCATGGTGGGGAACTGGACGAAGGTCCTGG
              490       500       510       520       530       540

550       560       570
   HCV1    TAGTGCTGCTGCTATTTGCCGGCGTCGACGCG
           ::::::::::::::::::::::::::::::::
   AY6510  TAGTGCTGCTGCTATTTGCCGGCGTCGACGCG
              550       560       570
```

Fig: 14

```
              10        20        30        40        50        60
   HCV1    ACCCACGTCACCGGGGGAAGTGCCGGCCACACTGTGTCTGGATTTGTTAGCCTCCTCGCA
           :   ::    ::::  :::::::::::::::::   ::     :  :::::  :::::  ::   ::   ::
   AY6510  ACCATCGTCTCCGGGGGAAGTGCCGGCCGCAGCACGGCTGGACTTGTTGGGCTCTTCTCA
              10        20        30        40        50        60

70        80        90        100       110       120
   HCV1    CCAGGCGCCAAGCAGAACGTCCAGCTGATCAACACCAACGGCAGTTGGCACCTCAATAGC
           ::::::::::  ::::::  :::::::::::::::::::::::::::::::::::  ::::::    ::   ::
   AY6510  CCAGGCGCCCGGCAGAACATCCAGCTGATCAACACCAACGGCAGTTGGCACATCAACCGC
              70        80        90        100       110       120

130       140       150       160       170       180
   HCV1    ACGGCCCTGAACTGCAATGATAGCCTCAACACCGGCTGGTTGGCAGGGCTTTTCTATCAC
           :::::::::::::::::::::::::  :::  :  :  ::::::::   : :::::::::::::::::::::::::  :
   AY6510  ACGGCCCTGAACTGCAATGATACCCTTCAAACCGGCTGGGTAGCAGGGCTTTTCTATACC
              130       140       150       160       170       180

190       200       210       220       230       240
   HCV1    CACAAGTTCAACTCTTCAGGCTGTCCTGAGAGGCTAGCCAGCTGCCGACCCCTTACCGAT
           ::::   :::::::::::::  :: ::  ::  ::::::  :   :::::::::::::::::::::::  ::::
   AY6510  AACAAATTCAACTCTTCGGGTTGCCCCGAGAGGTTGGCCAGCTGCCGACCCCTTGCCGAC
              190       200       210       220       230       240

250       260       270       280       290       300
   HCV1    TTTGACCAGGGCTGGGGCCCTATCAGTTATGCCAACGGAAGCGGCCCCGACCAGCGCCCC
           ::::::::::::::::::::::::::::::::::::::  :::::::::::::::::::::::::  ::::::
   AY6510  TTTGACCAGGGCTGGGGCCCTATCAGTTATACCAACGGAAGCGGCCCCGACCAACGCCCC
              250       260       270       280       290       300

310       320       330       340       350       360
```

Fig. 14 continued

```
HCV1    TACTGCTGGCACTACCCCCCAAAACCTTGCGGTATTGTGCCCGCGAAGAGTGTGTGTGGT
        ::::::::::::::::::::::::::::::::  :::::::::::::::  ::::  :::::::::::
AY6510  TACTGCTGGCACTACCCCCCAAAACCTTGTGGTATTGTGCCCGCAGAGAGCGTGTGTGGC
              310       320       330       340       350       360

370       380       390       400       410       420
HCV1    CCGGTATATTGCTTCACTCCCAGCCCCGTGGTGGTGGGAACGACCGACAGGTCGGGCGCG
        ::  :::::  ::::::::::::::::::::::::::::::::::::::::::::::::::::::::::::
AY6510  CCAGTATACTGCTTCACTCCCAGCCCCGTGGTGGTGGGAACGACCGACAGGTCGGGCGCG
              370       380       390       400       410       420

430       440       450       460       470       480
HCV1    CCCACCTACAGCTGGGGTGAAAATGATACGGACGTCTTCGTCCTTAACAATACCAGGCCA
        ::::::::::::  :::::::::::::::::  ::::::::  ::::::::  :::::  :::::::::
AY6510  CCCACCTACAACTGGGGTGAAAATGAAACGGACGTTTTCGTCCTCAACAACACCAGGCCA
              430       440       450       460       470       480

490       500       510       520       530       540
HCV1    CCGCTGGGCAATTGGTTCGGTTGTACCTGGATGAACTCAACTGGATTCACCAAAGTGTGC
        :  :::::::::::::::::::::::  ::::::::::::::::::::::::::::::::  ::::::
AY6510  CGGCTGGGCAATTGGTTCGGTTGGTACCTGGATGAACTCAACTGGATTCACCAAGGTGTGC
              490       500       510       520       530       540

550       560       570       580       590       600
HCV1    GGAGCGCCTCCTTGTGTCATCGGAGGGGCGGGCAACAACACCCTGCACTGCCCCACTGAT
        :::::::::  :::::::  ::::::::::  :::::::::::::::::  ::  :::::::::::::::
AY6510  GGAGCGCCCCCTTGTGCCATCGGAGGGGTGGGCAACAACACCTTGTACTGCCCCACTGAT
              550       560       570       580       590       600

610       620       630       640       650       660
HCV1    TGCTTCCGCAAGCATCCGGACGCCACATACTCTCGGTGCGGCTCCGGTCCCTGGATCACA
        ::  ::::::::  :::::::::  :::::  ::::::::::::::::::::::::  :::::  :::
AY6510  TGTTTCCGCAAACATCCGGAAGCCACGTACTCTCGGTGCGGCTCCGGTCCTTGGATTACA
              610       620       630       640       650       660

670       680       690       700       710       720
HCV1    CCCAGGTGCCTGGTCGACTACCCGTATAGGCTTTGGCATTATCCTTGTACCATCAACTAC
        ::::::::::  ::  ::::::::::::::::::::::::::::::::::::::::::::  :::
AY6510  CCCAGGTGCTTGATCCACTACCCGTATAGGCTTTGGCATTATCCTTGTACCATCAATTAC
              670       680       690       700       710       720

730       740       750       760       770       780
HCV1    ACCATATTTAAAATCAGGATGTACGTGGGAGGGGTCGAACACAGGCTGGAAGCTGCCTGC
        :::::::::  ::  ::::::::::::  :::::  ::::::  ::::::::::  :::  ::  :::
AY6510  ACCATATTCAAGATCAGGATGTTTGTGGGCGGGGTTGAGCACAGGCTCGACGCCGCGTGC
              730       740       750       760       770       780

790       800       810       820       830       840
HCV1    AACTGGACGCGGGGCGAACGTTGCGATCTGGAAGACAGGGACAGGTCCGAGCTCAGCCCG
        ::::::::::::::::::  ::  :::::  ::::  :::::::::  :::::  :  :::::
AY6510  AACTGGACGCGGGGAGAGCGCTGCGACTTGGACGACAGGGATCGGGCCGAGTTGAGCCCT
              790       800       810       820       830       840

850       860       870       880       890       900
HCV1    TTACTGCTGACCACTACACAGTGGCAGGTCCTCCCGTGTTCCTTCACAACCCTACCAGCC
        :  :::::  :::::::::  ::  ::::::::::::  ::  :::::::::  ::  ::  :::
AY6510  CTGTTGCTGTCCACTACGCAATGGCAGGTCCTCCCCTGCTCATTCACAACACTGCCCGCC
```

Fig. 14 continued

```
              850       860       870       880       890       900

910       920       930       940       950       960
HCV1    TTGTCCACCGGCCTCATCCACCTCCACCAGAACATTGTGGACGTGCAGTACTTGTACGGG
        ::::  ::  :::::  ::  ::  :::::::::::::::  ::::::::::::::::: :  :: :::
AY6510  CTGTCAACTGGCCTGATACATCTCCACCAGAACATCGTGGACGTGCAGTACCTCTATGGG
              910       920       930       940       950       960

970       980       990       1000      1010      1020
HCV1    GTGGGGTCAAGCA-TCGCGTCCTGGGCCATTAAGTGGGAGTACGTCGTTCTCCTGTTCCT
        ::  :  ::    :::  ::  :  :::::::    :::   :::::::::::  ::  ::::: :::  :
AY6510  TTGAGCTCG-GCAGTCACATCCTGGGTCATAAAGTGGGAGTACGTTGTGCTCCTCTTCTT
              970       980       990       1000      1010      1020

1030      1040      1050      1060      1070      1080
HCV1    TCTGCTTGCAGACGCGCGCGTCTGCTCCTGCTTGTGGATGATGCTACTCATATCCCAAGC
        :::::  :::::::  ::   :::   :  ::   :::::::::::::::::::: ::::::::: :: :
AY6510  GCTGCTAGCAGATGCTCGCATTTGTGCCTGCTTGTGGATGATGCTTCTCATATCTCAGGT
              1030      1040      1050      1060      1070      1080

1090      1100      1110      1120      1130      1140
HCV1    GGAGGCGGCTTTGGAGAACCTCGTAATACTTAATGCAGCATCCCTGGCCGGGACGCACGG
        ::::::::: :::::::::  ::  ::  :: ::  :: :: :::::  : ::::::: :: ::
AY6510  AGAGGCGGCGCTGGAGAACTTGATAGTTCTCAACGCTGCTTCCCTAGTCGGGACACATGG
              1090      1100      1110      1120      1130      1140

1150      1160      1170      1180      1190      1200
HCV1    TCTTGTATCCTTCCTCGTGTTCTTCTGCTTTGCATGGTATTTGAAGGGTAAGTGGGTGCC
        :  ::  :::::: ::  ::  ::  ::           ::  :::::  :  ::  ::  :::::::::    ::
AY6510  CATCGTCCCCTTCTTCATCTTTTTTTGTGCAGCTTGGTACCTAAAAGGCAAGTGGGCCCC
              1150      1160      1170      1180      1190      1200

1210      1220      1230      1240      1250      1260
HCV1    CGGAGCGGTCTACACCTTCTACGGGATGTGGCCTCTCCTCCTGCTCCTGTTGGCGTTGCC
        :::     :  :::    ::  ::::   :::::::::::::  ::   :::::::::   ::.  :::::::::::
AY6510  TGGACTCGCCTATTCCGTCTATGGGATGTGGCCACTGCTCCTGCTTCTCCTGGCGTTGCC
              1210      1220      1230      1240      1250      1260

1270
HCV1    CCAGCGGGCGTACGC
        :::  :::::  :::::
AY6510  CCAACGGGCATACGC
              1270
```

FIG: 15

```
              10        20        30        40        50        60
HCV1    TGGACACGGAGGTGGCCGCGTCGTGTGGCGGTGTTGTTCTCGTCGGGTTGATGGCGCTGA
        ::::   ::::  ::::::::::::::::: :     ::   ::  ::  :   ::  :::  :
AY6510  TGGATCAGGAGTTGGCCGCGTCGTGTGGGGCCACGGTCTTCATCTGCCTAGCGGTGCTCA
              10        20        30        40        50        60.

70        80        90        100       110       120
HCV1    CTCTGTCACCATATTACAAGCGCTATATCAGCTGGTGCTTGTGGTGGCTTCAGTATTTTC
        ::::  ::  :::::::::::::  :    ::  ::  :   ::  ::  ::::::::::: :  :
AY6510  CTCTATCGCCATATTACAAACAGTACATGGCCCGCGGCATCTGGTGGCTGCAGTACATGC
              70        80        90        100       110       120
```

Fig. 15 continued

```
             130       140       150       160       170       180
HCV1    TGACCAGAGTGGAAGCGCAACTGCACGTGTGGATTCCCCCCCTCAACGTCCGAGGGGGGC
        ::::::::: :: :::: :: :: :: ::: :::::  :::::::  :::::::  :::: 
AY6510  TGACCAGAGCAGAGGCGCTCCTACAGGTTTGGGTCCCCCCGCTCAACGCCCGAGGAGGGC
             130       140       150       160       170       180

190       200       210       220       230       240
HCV1    GCGACGCCGTCATCTTACTCATGTGTGCTGTACACCCG-ACTCTGGTATTTGACATCACC
        ::::::  :::  :  :  :::: :::::      :  :::::::   ::  : ::::: ::::::
AY6510  GCGACGGAGTCGTACTGCTCACGTGTGTGCTCCACCCGCACT-TGCTCTTTGAAATCACC
             190       200       210       220       230       240

250       260       270       280       290       300
HCV1    AAATTGCTGCTGGCCGTCTTCGGACCCCTTTGGATTCTTCAAGCCAGTTTGCTTAAAGTA
        ::  :  :::::::::  ::::  :: ::  ::::::  :  :::::::  ::::  :  :::
AY6510  AAGATCATGCTGGCCATTCTCGGGCCTTTGTGGATCTTGCAGGCCAGTCTGCTCAAGGTA
             250       260       270       280       290       300

310       320       330       340       350       360
HCV1    CCCTACTTTGTGCGCGTCCAAGGCCTTCTCCGGTTCTGCGCGTTAGCGCGGAAGATGATC
        :: ::::: ::::::::  :: :::::::::::::::: :::::::::::::::::::::: :: 
AY6510  CCGTACTTCGTGCGCGTTCAGGGCCTTCTCCGGATCTGCGCGCTAGCGCGGAAGATGGTC
             310       320       330       340       350       360

370       380       390       400       410       420
HCV1    GGAGGCCATTACGTGCAAATGGTCATCATTAAGTTAGGGGCGCTTACTGGCACCTATGTT
        :::::::::::::::::::::::::::: ::: ::::::::::::::: ::::::::::::: ::
AY6510  GGAGGCCATTACGTGCAAATGGTCACCATCAAGTTAGGGGCGCTCACTGGCACCTATATT
             370       380       390       400       410       420

430       440       450       460       470       480
HCV1    TATAACCATCTCACTCCTCTTCGGGACTGGGCGCACAACGGCTTGCGAGATCTGGCCGTG
        :::::::::::::::::::::::::::::::::::::::::::::::: ::: :: :::::
AY6510  TATAACCATCTCACTCCTCTTCGGGACTGGGCGCACAACGGCTTGCAAGACCTAGCCGTA
             430       440       450       460       470       480

490       500       510       520       530       540
HCV1    GCTGTAGAGCCAGTCGTCTTCTCCCAAATGGAGACCAAGCTCATCACGTGGGGGGCAGAT
        ::::: :::::::::::::::::::::::::::::::::::::::::::::::::::::: 
AY6510  GCTGTGGAGCCAGTCGTCTTCTCCCAAATGGAGACCAAGCTCATCACGTGGGGGGCAGAC
             490       500       510       520       530       540

550       560       570       580       590
HCV1    ACCGCCGCGTGCGGTGACATCATCAACGGCTTGCCTGTTTCCGCCCGCAGG
        ::  ::::::::  ::::::::::::::::::::::::  ::  :::::::::::::
AY6510  ACAGCCGCGTGTGGTGACATCATCAACGGCTTGCCCGTCTCCGCCCGCAGG
             550       560       570       580       590
```

Fig: 16

```
             10        20        30        40        50        60
HCV1    GGCCGGGAGATACTGCTCGGGCCAGCCGATGGAATGGTCTCCAAGGGGTGGAGGTTGCTG
        ::::  :::::::::::::::::  ::::::::::::::::::::: ::: ::::::::::::::::::
AY6510  GGCCAGGAGATACTGCTCGGACCAGCCGATGGAATGGCCTCTAGGGGATGGAGGTTGCTG
             10        20        30        40        50        60
```

Fig. 16 continued

```
                 70        80        90       100       110       120
HCV1     GCGCCCATCACGGCGTACGCCCAGCAGACAAGGGGCCTCCTAGGGTGCATAATCACCAGC
         ::::::::::::::::::::: :::::::::::::::::::::::::: :::::::::::
AY6510   GCGCCCATCACGGCGTACGCTCAGCAGACAAGGGGCCTCCTAGGGTGTATAATCACCAGC
                 70        80        90       100       110       120

130       140       150       160       170       180
HCV1     CTAACTGGCCGGGACAAAAACCAAGTGGAGGGTGAGGTCCAGATTGTGTCAACTGCTGCC
         :: :::::::::::::::: :::::::::::::::: :::::::::::::::::::::::
AY6510   CTGACTGGCCGGGACAAGAACCAAGTGGAGGGTGAAGTCCAGATTGTGTCAACTGCTGCC
                130       140       150       160       170       180

190       200       210       220       230       240
HCV1     CAAACCTTCCTGGCAACGTGCATCAATGGGGTGTGCTGGACTGTCTACCACGGGGCCGGA
         ::::: ::: :::: ::::::::::::: :::: ::::::::::::::::::::::::::
AY6510   CAAACGTTCTTGGCGACGTGCATCAACGGGGTATGCTGGACTGTCTACCACGGGGCCGGA
                190       200       210       220       230       240

250       260       270       280       290       300
HCV1     ACGAGGACCATCGCGTCACCCAAGGGTCCTGTCATCCAGATGTATACCAATGTAGACCAA
         :: :::::::::: :: ::: ::::::::::::: :: : ::::::::::::::::::::
AY6510   ACCAGGACCATTGCATCATCCAAGGGTCCTGTTATTCTAATGTATACCAATGTAGACCAA
                250       260       270       280       290       300

310       320       330       340       350       360
HCV1     GACCTTGTGGGCTGGCCCGCTCCGCAAGGTAGCCGCTCATTGACACCCTGCACTTGCGGC
         ::::: : ::::::::: ::::: :::: : ::::: ::::::::::::::: :::::::
AY6510   GACCTCGGGGGCTGGACCGCTCCTCAAGTGCTCGGCTCACTGACACCCTGGAGCTGCGGC
                310       320       330       340       350       360

370       380       390       400       410       420
HCV1     TCCTCGGACCTTTACCTGGTCACGAGGCACGCCGATGTCATTCCCGTGCGCCGGCGGGGT
         :::::::::::::::::::::::::::: :::::::::::::::::::: : ::::: :::
AY6510   TCCTCGGACCTTTACCTGGTCACGAGGCATGCCGATGTCATTCCCGTGCCGCGGCGAGGT
                370       380       390       400       410       420

430       440       450       460       470       480
HCV1     GATAGCAGGGGCAGCCTGCTGTCGCCCCGGCCCATTTCCTACTTGAAAGGCTCCTCGGGG
         :: : :::::::::::::: :::::::::::::::::::::: :: :: ::::::::::
AY6510   GAAACCAGGGGCAGCCTGCTTTCGCCCCGGCCCATTTCCTATCTAAAGGGATCCTCGGGA
                430       440       450       460       470       480

490       500       510       520       530       540
HCV1     GGTCCGCTGTTGTGCCCCGCGGGGCACGCCGTGGGCATATTTAGGGCCGCGGTGTGCACC
         :: :: ::: : :: ::: ::: :: :::::::::::::: :: ::::::::::::::::
AY6510   GGCCCCCTGCTCTGTCCCATGGGACATGCCGTGGGCATTTTCAGGGCCGCGGTGTGCACC
                490       500       510       520       530       540

550       560       570       580       590       600
HCV1     CGTGGAGTGGCTAAGGCGGTGGACTTTATCCCTGTGGAGAACCTAGAGACAACCATGAGG
         ::::: :: :: :::::::::: ::::: : :: :: :::  : :::::::: :::::::
AY6510   CGTGGGGTCGCAAAGGCGGTCGACTTTGTGCCCGTTGAGTCCTTAGAGACCACCATGAGG
                550       560       570       580       590       600

610       620       630       640       650       660
HCV1     TCCCCGGTGTTCACGGATAACTCCTCTCCACCAGTAGTGCCCCAGAGCTTCCAGGTGGCT
```

Fig. 16 continued

```
       :::::  :::::  ::  ::  ::  :::      ::  :  :   ::::::::::::  :  :::::::::::
AY6510 TCCCCAGTGTTTACTGACAATTCCAGCCCTCTAACAGTGCCCCAGAGTTACCAGGTGGCG
           610       620       630       640       650       660

670       680       690       700       710       720
HCV1   CACCTCCATGCTCCCACAGGCAGCGGCAAAAGCACCAAGGTCCCGGCTGCATATGCAGCT
       ::  ::  :::::  :::::  ::  ::  :::::  :::::  :::::  :::::  ::  ::  :::::
AY6510 CATCTACATGCACCCACTGGGAGTGGCAAGAGCACGAAGGTGCCGGCCGCTTACGCAGCT
           670       680       690       700       710       720

730       740       750       760       770       780
HCV1   CAGGGCTATAAGGTGCTAGTACTCAACCCCTCTGTTGCTGCAACACTGGGCTTTGGTGCT
       :::::  ::  :::::  ::  ::  ::  :::::  ::::::::::::  ::   :::  ::  ::::::
AY6510 CAGGGGTACAAGGTACTTGTGCTGAACCCGTCTGTTGCTGCCACCTTAGGGTTCGGTGCT
           730       740       750       760       770       780

790       800       810       820       830       840
HCV1   TACATGTCCAAGGCTCATGGGATCGATCCTAACATCAGGACCGGGGTGAGAACAATTACC
       ::  :::::  :::::  :::::::::::::  ::  ::::::::::::::  :::::  ::  ::  :::
AY6510 TATATGTCAAAGGCCCATGGGATCGACCCAAACATCAGGACCGGCGTGAGGACCATCACC
           790       800       810       820       830       840

850       860       870       880       890       900
HCV1   ACTGGCAGCCCCATCACGTACTCCACCTACGGCAAGTTCCTTGCCGACGGCGGGTGCTCG
       ::  :::  :::::::::::  :::::::::::::::::  ::   ::  ::  :::::  :::  :
AY6510 ACAGGCTCCCCCATCACCTACTCCACCTACGGCAAATTTTTGGCTGATGGCGGATGCCCA
           850       860       870       880       890       900

910       920       930       940       950       960
HCV1   GGGGGCGCTTATGACATAATAATTTGTGACGAGTGCCACTCCACGGATGCCACATCCATC
       ::  ::  ::  ::  :::::  :::::  :::::::::  ::  :::::     :::  :::::  ::  ::
AY6510 GGAGGTGCGTACGACATCATAATATGTGACGAATGTCACTCAGTGGACGCCACCTCGATT
           910       920       930       940       950       960

970       980       990      1000      1010      1020
HCV1   TTGGGCATCGGCACTGTCCTTGACCAAGCAGAGACTGCGGGGGCGAGACTGGTTGTGCTC
       :::::::  ::  ::  :::  :  :::::::::  :::::  ::::::::  ::  ::   :::  :::
AY6510 CTGGGCATAGGGACCGTCTTGGACCAAGCGGAGACGGCGGGGGTCAGGCTCACTGTCCTC
           970       980       990      1000      1010      1020

1030      1040      1050      1060      1070      1080
HCV1   GCCACCGCCACCCCTCCGGGCTCCGTCACTGTGCCCCATCCCAACATCGAGGAGGTTGCT
       :::::::::  ::  ::  ::  ::  :::::::::  :::::  :::  :::::::::::::  :::::
AY6510 GCCACCGCTACACCACCTGGTTCCGTCACCGTGCCACATTCCAACATCGAGGAAGTTGCA
          1030      1040      1050      1060      1070      1080

1090      1100      1110      1120      1130
HCV1   CTGTCCACCACCGGAGAGATCCCTTTTTACGGCAAGGCTATCCCCCTCGAAGTA-ATCAA
       ::::::  :   :::  ::  ::  ::  :::::  ::  :::::  :::::::  ::  :: :::::
AY6510 CTGTCCGCTGACGGGGAAATACCATTTTATGGTAAGGCCATCCCCCTA-AACTACATCAA
          1090      1100      1110      1120      1130

1140      1150      1160      1170      1180      1190
HCV1   GGGGGGAGACATCTCATCTTCTGTCATTCAAAGAAGAAGTGCGACGAACTCGCCGCAAA
       ::::::::::  ::  :::::  :::::  ::  ::  ::::::::::::::  :::::  :::::
AY6510 GGGGGGGAGGCACCTCATTTTCTGCCACTCCAAGAAGAAGTGCGACGAGCTCGCTGCAAA
          1140      1150      1160      1170      1180      1190
```

Fig. 16 continued

```
              1200      1210      1220      1230      1240      1250
HCV1    GCTGGTCGCATTGGGCATCAATGCCGTGGCCTACTACCGCGGTCTTGACGTGTCCGTCAT
        ::::::::  ::::  ::::  ::  ::::::::   :::::  ::  ::  :::::  ::  :::::
AY6510  GCTGGTCGGTCCGGGCGTCAACGCGGTGGCCTTTTACCGTGGCCTCGACGTATCTGTCAT
              1200      1210      1220      1230      1240      1250

1260      1270      1280      1290      1300      1310
HCV1    CCCGACCAGCGGCGATGTTGTCGTCGTGGCAACCGATGCCCTCATGACCGGCTATACCGG
        ::  ::   :   ::  ::  ::  ::  ::  ::  ::  :::::  :::   :  :::::  ::::   :::::
AY6510  TCCAACTACAGGAGACGTCGTTGTTGTAGCGACCGACGCCTTGATGACTGGCTTCACCGG
              1260      1270      1280      1290      1300      1310

1320      1330      1340      1350      1360      1370
HCV1    CGACTTCGACTCGGTGATAGACTGCAATACGTGTGTCACCCAGACAGTCGATTTCAGCCT
        ::  ::::::::::  ::::::::::::::  ::  ::::::   ::::::::::::  ::::::::
AY6510  AGATTTCGACTCTGTGATAGACTGCAACACCTGTGTCGTCCAGACAGTCGACTTCAGCCT
              1320      1330      1340      1350      1360      1370

1380      1390      1400      1410      1420      1430
HCV1    TGACCCTACCTTCACCATTGAGACAATACGCTCCCCCAGGATGCTGTCTCCCGCACTCA
        ::::::::    :::   :    :::::::::      :::   :    ::::::::::  ::  ::   ::::::   :   ::
AY6510  AGACCCTATATTCTCTATTGAGACTTCCACCGTGCCCCAGGACGCCGTGTCCCGCTCCCA
              1380      1390      1400      1410      1420      1430

1440      1450      1460      1470      1480      1490
HCV1    ACGTCGGGGCAGGACTGGCAGGGGGAAGCCAGGCATCTACAGATTTGTGGCACCGGGGGA
        :::    ::::  ::::  ::   :    ::::::::    ::  ::  ::::::::   ::::  ::::  :::::
AY6510  ACGGAGGGGTAGGACCGGTCGAGGGAAGCATGGTATTTACAGATATGTGTCACCCGGGGA
              1440      1450      1460      1470      1480      1490

1500      1510      1520      1530      1540      1550
HCV1    GCGCCCCTCCGGCATGTTCGACTCGTCCGTCCTCTGTGAGTGCTATGACGCAGGCTGTGC
        :::  ::  ::  ::::::::::::::      ::::::::::::::::::::::::  ::  :::::
AY6510  GCGGCCGTCTGGCATGTTCGACTCCGTGGTCCTCTGTGAGTGCTATGACGCGGGTTGTGC
              1500      1510      1520      1530      1540      1550

1560      1570      1580      1590      1600      1610
HCV1    TTGGTATGAGCTCACGCCCGCCGAGACTACAGTTAGGCTACGAGCGTACATGAACACCCC
        ::::::  :::::  ::  ::::::::::  :::::  ::::::::::  ::  :::   :  :::::::::
AY6510  TTGGTACGAGCTTACACCCGCCGAGACCACAGTCAGGCTACGGGCATACCTCAACACCCC
              1560      1570      1580      1590      1600      1610

1620      1630      1640      1650      1660      1670
HCV1    GGGGCTTCCCGTGTGCCAGGACCATCTTGAATTTTGGGAGGGCGTCTTTACAGGCCTCAC
        ::    :  :::::::::::::  :  ::::::::  ::::::  :   ::::::  ::  :::::::::
AY6510  AGGATTGCCCGTGTGCCAGGACCACTTGGAGTTCTGGGAGAGTGTCTTCACCGGCCTCAC
              1620      1630      1640      1650      1660      1670

1680      1690      1700      1710      1720      1730
HCV1    TCATATAGATGCCCACTTTCTATCCCAGACAAAGCAGAGTGGGGAGAACCTTCCTTACCT
        ::  ::::::::::::::  ::  ::::::::  ::  ::::::::::  ::  :::::::::  ::::::::
AY6510  CCACATAGATGCCCACTTCCTGTCCCAGACGAAACAGAGTGGGGAGAACTTCCCCTACCT
              1680      1690      1700      1710      1720      1730

1740      1750      1760      1770      1780      1790
HCV1    GGTAGCGTACCAAGCCACCGTGTGCGCTAGGGCTCAAGCCCCTCCCCCATCGTGGGACCA
```

Fig. 16 continued

```
       :: ::  ::::::::::::::::::::: :::    :::  ::::::::: :: :::::::::
AY6510 AGTCGCATACCAAGCCACCGTGTGCGCTAGAGCTAGAGCTCCTCCCCCGTCATGGGACCA
          1740      1750      1760      1770      1780      1790

1800      1810      1820      1830      1840      1850
HCV1   GATGTGGAAGTGTTTGATTCGCCTCAAGCCCACCCTCCATGGGCCAACACCCCTGCTATA
       ::::::::::::  :::::  ::  ::::::::::::::::   ::::  :  ::  ::   :  :::::
AY6510 AATGTGGAAGTGCCTGATACGGCTCAAGCCCACCCTCACTGGGGCTACCCCATTACTATA
          1800      1810      1820      1830      1840      1850

1860      1870      1880      1890      1900      1910
HCV1   CAGACTGGGCGCTGTTCAGAATGAAATCACCCTGACGCACCCAGTCACCAAATACATCAT
       ::::::::::     :::  :::::::::  ::::::: : ::  ::::::  :::::  :::::::::::
AY6510 CAGACTGGGTAGTGTACAGAATGAGATCACCTTAACACACCCAATCACCCAATACATCAT
          1860      1870      1880      1890      1900      1910

1920      1930      1940      1950
HCV1   GACATGCATGTCGGCCGACCTGGAGGTCGTCAC
       : :  ::::::::::::  ::::::::::::::::::
AY6510 GGCTTGCATGTCGGCGGACCTGGAGGTCGTCAC
          1920      1930      1940      1950
```

Fig: 17

```
              10        20        30        40        50        60
HCV1   AGCACCTGGGTGCTCGTTGGCGGCGTCCTGGCTGCTTTGGCCGCGTATTGCCTGTCAACA
       :::::  ::::::  :   ::  :::::::::::  ::  :::::::::::::  ::  :::::::::  :::
AY6510 AGCACGTGGGTGTTGGTGGGCGGCGTCCTAGCCGCTTTGGCCGCTTACTGCCTGTCCACA
              10        20        30        40        50        60

70        80        90       100       110       120
HCV1   GGCTGCGTGGTCATAGTGGGCAGGGTCGTCTTGTCCGGGAAGCCGGCAATCATACCTGAC
       :::  :::::::::::::::::::::::::  :   ::  :            :::::::::::::  ::::::::::::
AY6510 GGCAGCGTGGTCATAGTGGGCAGGATAATCCTAGGTGGGAAGCCGGCAGTCATACCTGAC
              70        80        90       100       110       120

130       140       150       160       170       180
HCV1   AGGGAAGTCCTCTACCGAGAGTTCGATGAGATGGAAGAGTGCTCTCAGCACTTACCGTAC
       :::::  ::  ::::::::::::::::  ::::::::::::::  :::::::  :        :::  :  ::  :::
AY6510 AGGGAGGTTCTCTACCGAGAGTTTGATGAGATGGAGGAGTGCGCCGCCCACGTCCCCTAC
             130       140       150       160       170       180

190       200       210       220       230       240
HCV1   ATCGAGCAAGGGATGATGCTCGCCGAGCAGTTCAAGCAGAAGGCCCTCGGCCTCCTGCAG
       ::::::::::  ::::::::::  :::::::::::::::::::  ::  ::  ::   :  ::  :::
AY6510 CTCGAGCAGGGGATGCATTTGGCGGAGCAGTTCAAGCAGAAAGCTCTTGGGTTGCTCCAG
             190       200       210       220       230       240

250       260       270       280       290       300
HCV1   ACCGCGTCCCGTCAGGCAGAGGTTATCGCCCCTGCTGTCCAGACCAACTGGCAAAAACTC
       ::  ::  :::  ::  :::::  :::  :::::  ::::::::::  :  :::::  ::  :::
AY6510 ACGGCATCCAAACAAACAGAGACGATCACTCCCATTGTCCAGTCTAATTGGCAGAAGCTC
             250       260       270       280       290       300
```

Fig. 17 continued

```
              310        320        330        340        350        360
HCV1    GAGACCTTCTGGGCGAAGCATATGTGGAACTTCATCAGTGGGATACAATACTTGGCGGGC
        ::: : :::::::: :: :: :::::::::::: : :: :::::::::::  ::::::::
AY6510  GAGTCTTTCTGGGCTAAACACATGTGGAACTTCGTTAGCGGGATACAATATCTGGCGGGC
              310        320        330        340        350        360

370        380        390        400        410        420
HCV1    TTGTCAACGCTGCCTGGTAACCCCGCCATTGCTTCATTGATGGCTTTTACAGCTGCTGTC
        : ::::::::::: :: ::::::::: :: :: ::  ::::: : ::::: :: :: ::
AY6510  CTATCAACGCTGCCCGGGAACCCCGCTATAGCATCGCTGATGTCGTTTACGGCCGCAGTG
              370        380        390        400        410        420

430        440        450        460        470        480
HCV1    ACCAGCCCACTAACCACTAGCCAAACCCTCCTCTTCAACATATTGGGGGGGTGGGTGGCT
        :: :: ::::::::::::: :: :::::::::::: :::::::::::::::: :::::
AY6510  ACGAGTCCACTAACCACTCAGCAGACCCTCCTCTTTAACATCTTGGGGGGGTGGCTGGCT
              430        440        450        460        470        480

490        500        510        520        530        540
HCV1    GCCCAGCTCGCCGCCCCCGGTGCCGCTACTGCCTTTGTGGGCGCTGGCTTAGCTGGCGCC
        :::::::: :::::::: ::::: :: ::::: :: ::::: ::: : ::::::::::
AY6510  GCCCAGCTTGCCGCCCCAGCCGCCGCCACAGCCTTCGTTGGCGCAGGCATTACTGGCGCC
              490        500        510        520        530        540

550        560        570        580        590        600
HCV1    GCCATCGGCAGTGTTGGACTGGGGAAGGTCCTCATAGACATCCTTGCAGGGTATGGCGCG
        :  :  ::::::::: :: ::::::::::::::: : ::::: :::: :: :: :: ::
AY6510  GTTGTTGGCAGTGTGGGCCTAGGGAAGGTCCTGGTGGACATTCTTGCCGGCTACGGGGCT
              550        560        570        580        590        600

610        620        630        640        650        660
HCV1    GGCGTGGCGGGAGCTCTTGTGGCATTCAAGATCATGAGCGGTGAGGTCCCCTCCACGGAG
        :: :::::: :: :: :: ::::: ::::: :::::::::: :: ::::::::::::::
AY6510  GGTGTGGCCGGGGCCCTCGTGGCTTTCAAAATCATGAGCGGGGAGACCCCCACCACGGAG
              610        620        630        640        650        660

670        680        690        700        710        720
HCV1    GACCTGGTCAATCTACTGCCCGCCATCCTCTCGCCCGGAGCCCTCGTAGTCGGCGTGGTC
        :: ::  ::::: :: :::::  ::::: :::::::: ::::: ::::: :::: ::::
AY6510  GATCTAGTCAACCTTCTGCCTGCCATCCTATCGCCAGGAGCTCTCGTTGTCGCCGTGGTG
              670        680        690        700        710        720

730        740        750        760        770        780
HCV1    TGTGCAGCAATACTGCGCCGGCACGTTGGCCCGGGCGAGGGGGCAGTGCAGTGGATGAAC
        :: ::::::::::: :::::::::::: :::::: ::::: :: :::::::::::::::
AY6510  TGCGCAGCAATACTACGCCGGCACGTGGGCCTTGGCGAGGGCGCCGTGCAGTGGATGAAC
              730        740        750        760        770        780

790        800        810        820        830        840
HCV1    CGGCTGATAGCCTTCGCCTCCCGGGGGAACCATGTTTCCCCCACGCACTACGTGCCGGAG
        :::::::::::::: :: :: :: :::::::: :: ::::: :: :::::::::::::::
AY6510  CGGCTGATAGCGTTTGCTTCTCGGGGTAACCACGTCTCCCCTACACACTACGTGCCGGAG
              790        800        810        820        830        840

850        860        870        880        890        900
HCV1    AGCGATGCAGCTGCCCGCGTCACTGCCATACTCAGCAGCCTCACTGTAACCCAGCTCCTG
        ::::: ::  :  :: ::::: ::::: : ::::::::: ::::::  ::::: :::  :
```

Fig. 17 continued

```
AY6510 AGCGACGCGTCGGCTCGTGTCACACCAATTCTCACCAGGCTCACTGTTACTCAGCTTCTG
              850       860       870       880       890       900

910       920       930       940
HCV1   AGGCGACTGCACCAGTGGATAAGCTCGGAGTGTACCACTCCATG
        :  :  :: :::    ::::::::::::: :  ::  :  :  ::  ::
AY6510 AAAGGGCTCCACGTGTGGATAAGCTCGAATTGCATCGCCCCGTG
              910       920       930       940
```

FIG: 18

```
              10        20        30        40        50        60
HCV1   GTTCCTGGCTAAGGGACATCTGGGACTGGATATGCGAGGTGTTGAGCGACTTTAAGACCT
       ::::  :::::  :   ::   :::::  :::::::::::::::::::  ::::::::::::  ::::   :
AY6510 GTTCTTGGCTTAAAGATGTCTGGAACTGGATATGCGAGGTGCTGAGCGACTTCAAGAATT
              10        20        30        40        50        60

70        80        90       100       110       120
HCV1   GGCTAAAAGCTAAGCTCATGCCACAGCTGCCTGGGATCCCCTTTGTGTCCTGCCAGCGCG
       ::::  ::  ::  ::  ::   :  :::::  :::::  :::::::  ::  ::  ::::::::::  ::::
AY6510 GGCTGAAGGCCAAACTTGTACCACAACTGCCCGGGATCCCATTCGTATCCTGCCAACGCG
              70        80        90       100       110       120

130       140       150       160       170       180
HCV1   GGTATAAGGGGGTCTGGCGAGTGGACGGCATCATGCACACTCGCTGCCACTGTGGAGCTG
       ::::         :::::::::::  :  ::  ::::::  ::::::::::  ::::   :::::  ::
AY6510 GGTACCGTGGGGTCTGGCGGGGCGAGGGCATCGTGCACACTCGTTGCCCGTGTGGGGCCA
              130       140       150       160       170       180

190       200       210       220       230       240
HCV1   AGATCACTGGACATGTCAAAAACGGGACGATGAGGATCGTCGGTCCTAGGACCTGCAGGA
       :  ::  :::::::::::::::     :::::  :::::::  ::::::::  :::  :::::: :
AY6510 ATATAACTGGACATGTCAAGAACGGTTCGATGAGAATCGTCGGGCCTAAGACTTGCAGCA
              190       200       210       220       230       240

250       260       270       280       290       300
HCV1   ACATGTGGAGTGGGACCTTCCCCATTAATGCCTACACCACGGGCCCCTGTACCCCCCTTC
       :::    :::   :::::  :   :::::::::::  :::::  ::   :::::  ::  :::       :
AY6510 ACACCTGGCGTGGGTCGTTCCCCATTAACGCTTACACTACAGGCCCGTGCACGCCCTCCC
              250       260       270       280       290       300

310       320       330       340       350       360
HCV1   CTGCGCCGAACTACACGTTCGCGCTATGGAGGGTGTCTGCAGAGGAATATGTGGAGATAA
       :  ::::::::::  ::::::::::::::::::::::::::::::::::::  ::::::::::  :::
AY6510 CGGCGCCGAACTATACGTTCGCGCTATGGAGGGTGTCTGCAGAGGAGTATGTGGAGGTAA
              310       320       330       340       350       360

370       380       390       400       410       420
HCV1   GGCAGGTGGGGGACTTCCACTACGTGACGGGTATGACTACTGACAATCTCAAATGCCCGT
       :::  :  ::::::::::::::  ::::::  :::::   ::::  ::::::  ::  ::::  ::  :
AY6510 GGCGGCTGGGGGACTTCCATTACGTCACGGGGGTGACCACTGATAAACTCAAGTGTCCAT
              370       380       390       400       410       420

430       440       450       460       470       480
```

Fig. 18 continued

```
HCV1    GCCAGGTCCCATCGCCCGAATTTTTCACAGAATTGGACGGGGTGCGCCTACATAGGTTTG
        :::::::::: ::  :::::: ::  :  ::::::   :::::::::::::::::::: :
AY6510  GCCAGGTCCCCTCACCCGAGTTCTCCACAGAGGTGGACGGGGTGCGCCTGCATAGGTACG
              430       440       450       460       470       480

490       500       510       520       530       540
HCV1    CGCCCCCCTGCAAGCCCTTGCTGCGGGAGGAGGTATCATTCAGAGTAGGACTCCACGAAT
        : ::  :::::::: :::  ::::  :::::   :::::  :  :: :: :: :  ::::
AY6510  CCCCTCCCTGCAAACCCCTGCTACGGGATGAGGTGACGTTTAGCGTCGGGTTCAATGAAT
              490       500       510       520       530       540

550       560       570       580       590       600
HCV1    ACCCGGTAGGGTCGCAATTACCTTGCGAGCCCGAACCGGACGTGGCCGTGTTGACGTCCA
        ::: :::  :::::  ::  ::  :::::::::::  :: :::: :: :: :::: :  :
AY6510  ACCTGGTGGGGTCCCAGTTGCCCTGCGAGCCCGAGCCAGACGTAGCAGCATTAACATCAA
              550       560       570       580       590       600

610       620       630       640       650       660
HCV1    TGCTCACTGATCCCTCCCATATAACAGCAGAGGCGGCCGGGCGAAGGTTGGCGAGGGGAT
        :::: :: :: ::  ::::: :: :: ::  :: :::: ::: :::  :  : :::: :
AY6510  TGCTTACAGACCCCTTCCCACATCACTGCAAAGACGGCGGCGCGTAGGCTGAAGCGGGGT
              610       620       630       640       650       660

670       680       690       700       710       720
HCV1    CACCCCCCTCTGTGGCCAGCTCCTCGGCTAGCCAGCTATCCGCTCCATCTCTCAAGGCAA
        : ::::::::  :::::: ::  :: :: ::::::::::: :: :: :: :: :: ::::
AY6510  CTCCCCCCTCCCTGGCCAGTTCTTCTGCCAGCCAGCTGTCCGCGCCGTCACTGAAAGCAA
              670       680       690       700       710       720

730       740       750       760       770       780
HCV1    CTTGCACCGCTAACCATGACTCCCCTGATGCTGAGCTCATAGAGGCCAACCTCCTATGGA
        :  :::::: :::::::::::: :: :: :: ::  :::::::: :::::::::: ::::
AY6510  CATGCACCACTCACCATGACTCTCCAGACGCCGACCTCATAGAAGCCAACCTCCTGTGGA
              730       740       750       760       770       780

790       800       810       820       830       840
HCV1    GGCAGGAGATGGGCGGCAACATCACCAGGGTTGAGTCAGAAAACAAAGTGGTGATTCTGG
        :  :  :::::::::  :: :::::::: :: ::::: :::::::: : :  :: ::::::
AY6510  GACGGGAGATGGGGGGGAACATCACCAGAGTGGAGTCGGAGAACAAGATTGTTGTTCTGG
              790       800       810       820       830       840

850       860       870       880       890       900
HCV1    ACTCCTTCGATCCGCTTGTGGCGGAGGAGGACGAGCGGGAGATCTCCGTACCCGCAGAAA
        :  ::  ::::: :::: :::::  :::::::  ::::::::: ::  : :: :: :: :
AY6510  ATTCTTTCGACCCGCTCGTGGCAGAGGAGGATGACCGGGAGATTTCTATTCCAGCTGAGA
              850       860       870       880       890       900

910       920       930       940       950       960
HCV1    TCCTGCGGAAGTCTCGG-AGATTCGCCCAGGCCCTGCCCGTTTGGGCGCGGCCGGACTAT
        :  :::::::::  : :  : ::: ::: ::: :::::::    :::: :::::::: :::
AY6510  TTCTGCGGAAATTTAAGCAGTTTCCCCCCCG-CCATGCCCATATGGGCACGGCCGGATTAT
              910       920       930       940       950       960

970       980       990       1000      1010      1020
HCV1    AACCCCCCGCTAGTGGAGACGTGGAAAAAGCCCGACTACGAACCACCTGTGGTCCATGGC
        :: :: :: :: :::::  :::::: :::::::::::::: :: :::::  :: ::::::
AY6510  AATCCTCCCCTTGTGGAACCGTGGAAGCGCCCGGACTGTGATCCACCCTTAGTCCACGGG
```

Fig. 18 continued

```
                970       980       990      1000      1010      1020

1030      1040      1050      1060      1070      1080
HCV1    TGTCCGCTTCCACCTCCAAAGTCCCCTCCTGTGCCTCCGCCTCGGAAGAAGCGGACGGTG
        ::  ::  ::  :::::::::  :::  :   ::::  :::::  ::  ::  :::::  :::  :::::::::
AY6510  TGCCCCCTACCACCTCCCAAGCCGACTCCGGTGCCGCCACCCCGGAAAAAGAGGACGGTG
               1030      1040      1050      1060      1070      1080

1090      1100      1110      1120      1130      1140
HCV1    GTCCTCACTGAATCAACCCTATCTACTGCCTTGGCCGAGCTCGCCACCAGAAGCTTTGGC
        ::  ::        ::  ::  ::    ::::      ::::      ::::  :::::  :::::  :    :  :::  :::
AY6510  GTGCTGGACGAGTCTACAGTATCATCTGCTCTGGCTGAGCTTGCCACTAAGACCTTCGGC
               1090      1100      1110      1120      1130      1140

1150      1160      1170      1180      1190      1200
HCV1    AGCTCCTCAACTTCCGGCATTACGGGCGACAATACGACAACATCCTCTGAGCCCGCCCCT
        :::::    ::::  ::  :::  :  ::    :  :      :    :::  :      :::  ::          ::::  :  ::
AY6510  AGCTCTACAACCTCAGGCGTGACAAGTGGTGAAGCGGCCGAATCGTC----CCCGGCGCT
               1150      1160      1170      1180      1190

1210      1220      1230      1240      1250
HCV1    T--CTGG--CTGCCCCCCCGACTCCGACGCTGAGTCCTATTCCTCCATGCCCCCCCTGGA
          :   :::   :  :        :        :::::::::  :::::  ::  ::  :::::::::::  ::  ::
AY6510  TTCCTGCGACGGTGAGCTGGACTCCGAAGCTGAATCTTACTCCTCCATGCCCCCTCTCGA
        1200      1210      1220      1230      1240      1250

1260      1270      1280      1290      1300      1310
HCV1    GGGGGAGCCTGGGGATCCGGATCTTAGCGACGGGTCATGGTCAACGGTCAGTAGTGAGGC
        :::::  ::  :::::  ::  :::::  :::::::::::::  :::::  ::  ::  ::  :::::  :
AY6510  GGGGGAACCGGGGGACCCCGATCTCAGCGACGGGTCTTGGTCTACCGTGAGCAGTGATGG
               1260      1270      1280      1290      1300      1310

1320      1330      1340      1350      1360      1370
HCV1    CAACGCGGAGGATGTCGTGTGCTGCTCAATGTCTTACTCTTGGACAGGCGCACTCGTCAC
        :        :::::::::::::::::::::    :::::    :::::  :::::  :::::    :      :  ::
AY6510  CGGTACGGAGGATGTCGTGTGCTGCTCGATGTCCTACTCGTGGACGGGCGCCTTAATTAC
               1320      1330      1340      1350      1360      1370

1380      1390      1400      1410      1420      1430
HCV1    CCCGTGCGCCGCGGAAGAACAGAAACTGCCCATCAATGCACTAAGCAACTCGTTGCTACG
        ::  ::  ::::::  :::  :::   :::::  :::::::  :::::  ::  ::::::  ::::  ::
AY6510  GCCCTGTGCCGCAGAGGAAACCAAACTCCCCATCAACGCACTGAGTAACTCGCTGCTGCG
               1380      1390      1400      1410      1420      1430

1440      1450      1460      1470      1480      1490
HCV1    TCACCACAATTTGGTGTATTCCACCACCTCACGCAGTGCTTGCCAAAGGCAGAAGAAAGT
        ::::::::::::::::::::::::::::  :::::  :::  ::  :  :::::::::  :::::
AY6510  CCACCACAATTTGGTGTATTCCACCACCTCTCGCAGCGCTGGCAAGAGGCAGAAAAAAGT
               1440      1450      1460      1470      1480      1490

1500      1510      1520      1530      1540      1550
HCV1    CACATTTGACAGACTGCAAGTTCTGGACAGCCATTACCAGGACGTACTCAAGGAGGTTAA
        ::::::::::::  :::::  ::::::  ::  :::::::      :::::::  ::::::  :::::::::::  :::
AY6510  CACATTTGACAGGCTGCAGGTCCTGGACGATCATTACCGGGACGTGCTCAAGGAGGCTAA
               1500      1510      1520      1530      1540      1550

1560      1570      1580      1590      1600      1610
```

Fig. 18 continued

```
HCV1    AGCAGCGGCGTCAAAAGTGAAGGCTAACTTGCTATCCGTAGAGGAAGCTTGCAGCCTGAC
        ::  :::  ::  : ::::::::::::: :::::::::::::::::  :: :: :::::::::
AY6510  GGCCAAGGCATCCACAGTGAAGGCTAAATTGCTATCCGTAGAGGAGGCATGTAGCCTGAC
            1560      1570      1580      1590      1600      1610

1620      1630      1640      1650      1660      1670
HCV1    GCCCCCACACTCAGCCAAATCCAAGTTTGGTTATGGGGCAAAAGACGTCCGTTGCCATGC
        ::::::  :::::  :::  ::  ::::: ::::::  : :: :: :::::  :::::  :
AY6510  GCCCCCGCACTCCGCCAGATCAAAATTTGGCTATGGGCCGAAGGATGTCCGAAGCCATTC
            1620      1630      1640      1650      1660      1670

1680      1690      1700      1710      1720      1730
HCV1    CAGAAAGGCCGTAACCCACATCAACTCCGTGTGGAAAGACCTTCTGGAAGACAATGTAAC
        :::  :::::  ::  :::::::::::::::::::::  ::::::::::::  ::::::  :::
AY6510  CAGTAAGGCTATACGCCACATCAACTCCGTGTGGCAGGACCTTCTGGAGGACAATACAAC
            1680      1690      1700      1710      1720      1730

1740      1750      1760      1770      1780      1790
HCV1    ACCAATAGACACTACCATCATGGCTAAGAACGAGGTTTTCTGCGTTCAGCCTGAGAAGGG
        :::  :::::::::::::::::::::  :::::  :: :: :::::::::   ::  :: :: ::
AY6510  ACCTATAGACACTACCATCATGGCCAAGAATGAAGTCTTCTGCGTGAAGGCCGAAAAAGG
            1740      1750      1760      1770      1780      1790

1800      1810      1820      1830      1840      1850
HCV1    GGGTCGTAAGCCAGCTCGTCTCATCGTGTTCCCCGATCTGGGCGTGCGCGTGTGCGAAAA
        ::::::  :::::  :::::  ::  :::::::::  :::::  :::::  :::::::::::::::  ::
AY6510  GGGTCGCAAGCCCGCTCGCCTTATCGTGTACCCCGACCTGGGGGTGCGCGTGTGCGAGAA
            1800      1810      1820      1830      1840      1850

1860      1870      1880      1890      1900      1910
HCV1    GATGGCTTTGTACGACGTGGTTACAAAGCTCCCCTTGGCCGTGATGGGAAGCTCCTACGG
        ::  :::::::::  :::::  ::  : :  :::::::::  :  ::::::::::::  ::::::::::
AY6510  GAGAGCTTTGTATGACGTAGTCAAACAGCTCCCCATTGCCGTGATGGGACCCTCCTACGG
            1860      1870      1880      1890      1900      1910

1920      1930      1940      1950      1960      1970
HCV1    ATTCCAATACTCACCAGGACAGCGGGTTGAATTCCTCGTGCAAGCGTGGAAGTCCAAGAA
        :::::  :::::  ::::  :::::::::  ::  :::::  :  :  :::::::::  ::  :::::
AY6510  GTTCCAGTACTCGCCAGCGCAGCGGGTCGACTTCCTGCTTAACGCGTGGAAATCAAAGAA
            1920      1930      1940      1950      1960      1970

1980      1990      2000      2010      2020      2030
HCV1    AACCCCAATGGGGGTTCTCGTATGATACCCGCTGCTTTGACTCCACAGTCACTGAGAGCGA
        ::  ::: :::::::::  ::  ::::::  ::::: :::::::::::  :::::::::::::  ::
AY6510  AAACCCTATGGGGTTTTCCTATGACACCCGTTGCTTTGACTCAACAGTCACTGAGGCTGA
            1980      1990      2000      2010      2020      2030

2040      2050      2060      2070      2080      2090
HCV1    CATCCGTACGGAGGAGGCAATCTACCAATGTTGTGACCTCGACCCCCAAGCCCGCGTGGC
        :::::::::::::  :  ::::  ::::  :::::::::::  :::  : :::::::::  :::
AY6510  TATCCGTACGGAGGAAGACCTCTATCAATCTTGTGACCTGGTCCCTGAGGCCCGCGCGGC
            2040      2050      2060      2070      2080      2090

2100      2110      2120      2130      2140      2150
HCV1    CATCAAGTCCCTCACCGAGAGGCTTTATGTTGGGGGCCCTCTTACCAATTCAAGGGGGA
        :::  : :::  :::::  ::::::::::::  :  :::::::::  ::::::::::  :::  :
AY6510  CATAAGGTCTCTCACAGAGAGGCTTTACATCGGGGGCCCACTTACCAATTCTAAGGGACA
```

Fig. 18 continued

```
          2100       2110       2120       2130       2140       2150

2160       2170       2180       2190       2200       2210
HCV1   GAACTGCGGCTATCGCAGGTGCCGCGCGAGCGGCGTACTGACAACTAGCTGTGGTAACAC
       ::::::::::::   :  :::::::: :::::::::  :::::  ::::::::: :::::::
AY6510 AAACTGCGGCTATCGGCGATGCCGCGCAAGCGGCGTGCTGACCACTAGCTGCGGTAACAC
          2160       2170       2180       2190       2200       2210

2220       2230       2240       2250       2260       2270
HCV1   CCTCACTTGCTACATCAAGGCCCGGGCAGCCTGTCGAGCCGCAGGGCTCCAGGACTGCAC
       :  :  ::::::::: : :::::   : ::   :::::::::::::   :::::::::::::::
AY6510 CATAACTTGCTACCTTAAGGCTAGTGCGGCCTGTCGAGCTGCAAAGCTCCAGGACTGCAC
          2220       2230       2240       2250       2260       2270

2280       2290       2300       2310       2320       2330
HCV1   CATGCTCGTGTGTGGCGACGACTTAGTCGTTATCTGTGAAAGCGCGGGGGTCCAGGAGGA
       :::::::::::: ::::::::::::   :  ::::::::::::::::::::   :  :::::::
AY6510 CATGCTCGTGTGCGGCGACGACCTCGTCGTTATCTGTGAAAGCGCCGGTGTCAAGGAGGA
          2280       2290       2300       2310       2320       2330

2340       2350       2360       2370       2380       2390
HCV1   CGCGGCGAGCCTGAGAGCCTTCACGGAGGCTATGACCAGGTACTCCGCCCCCCCTGGGGA
       :::   ::::::::::::::::::::  ::::::::::::::::::::::::::::::::  ::
AY6510 CGCTGCGAGCCTGAGAGCCTTCACCGAGGCTATGACCAGGTACTCCGGCCCCCCGGGAGA
          2340       2350       2360       2370       2380       2390

2400       2410       2420       2430       2440       2450
HCV1   CCCCCCACAACCAGAATACGACTTGGAGCTCATAACATCATGCTCCTCCAACGTGTCAGT
       :::  : :::::::::::::::::::::::  :::::::: :::::::::::::  :::::  ::
AY6510 CCCGGCTCAACCAGAATACGACTTGGAGCTTATAACATCCTGCTCCTCCAATGTGTCGGT
          2400       2410       2420       2430       2440       2450

2460       2470       2480       2490       2500       2510
HCV1   CGCCCACGACGGCGCTGGAAAGAGGGTCTACTACCTCACCCGTGACCCTACAACCCCCCT
       :::  : ::::::::::::::  : :: :::::::::::   ::::::  ::  :::::
AY6510 CGCGCGCGACGGCGCTGGCCAAAGGGTCTATTATCTGACCCGTGAACCTGAGACTCCCCT
          2460       2470       2480       2490       2500       2510

2520       2530       2540       2550       2560       2570
HCV1   CGCGAGAGCTGCGTGGGAGACAGCAAGACACACTCCAGTCAATTCCTGGCTAGGCAACAT
       ::::   :  ::  :: ::::::::::::::::::::::::::  ::::::::::::::::::::
AY6510 CGCGCGTGCCGCTTGGGAGACAGCAAGACACACTCCAGTGAACTCCTGGCTAGGCAACAT
          2520       2530       2540       2550       2560       2570

2580       2590       2600       2610       2620       2630
HCV1   AATCATGTTTGCCCCCACACTGTGGGCGAGGATGATACTGATGACCCATTTCTTTAGCGT
       :::::::::::::::::: :::::::  :::::  : :: ::::::::::  ::  ::    :  :
AY6510 CATCATGTTTGCCCCCACTCTGTGGGTACGGATGGTCCTCATGACCCACTTATTCTCCAT
          2580       2590       2600       2610       2620       2630

2640       2650       2660       2670       2680       2690
HCV1   CCTTATAGCCAGGGACCAGCTTGAACAGGCCCTCGATTGCGAGATCTACGGGGCCTGCTA
       ::  :::::   :::  ::  :::::: :::: :: ::::: ::  :::::  :: :::       :
AY6510 ACTCATAGTTCAGGAGCACCTTGAAAAGGCTCTAGATTGTGAAATCTATGGAGCCACACA
          2640       2650       2660       2670       2680       2690

2700       2710       2720       2730       2740       2750
```

Fig. 18 continued

```
HCV1    CTCCATAGAACCACTTGATCTACCTCCAATCATTCAAAGACTCCATGGCCTCAGCGCATT
        ::::  :    :::   :  ::  ::::::    :::::::::::::::::::::::  ::
AY6510  CTCCGTCCCACCGTTGGACCTACCTGAAATCATTCAAAGACTCCATGGCCTCAGCGCGTT
         2700      2710      2720      2730      2740      2750

2760      2770      2780      2790      2800      2810
HCV1    TTCACTCCACAGTTACTCTCCAGGTGAAATTAATAGGGTGGCCGCATGCCTCAGAAAACT
        :::  :::::::::::::::::::::::::::  :::::::::  :::::::::  :::::
AY6510  TTCGCTCCACAGTTACTCTCCAGGTGAAATCAATAGGGTGGCTTCATGCCTCAGGAAACT
         2760      2770      2780      2790      2800      2810

2820      2830      2840      2850      2860      2870
HCV1    TGGGGTACCGCCCTTGCGAGCTTGGAGACACCGGGCCCGGAGCGTCCGCGCTAGGCTTCT
        ::::::  ::  ::::::::::::::::::::::::::::::::::::::::   :: ::
AY6510  TGGGGTTCCACCCTTGCGAGCTTGGAGACACCGGGCCCGGAGCGTCCGCGCCACACTCCT
         2820      2830      2840      2850      2860      2870

2880      2890      2900      2910      2920      2930
HCV1    GGCCAGAGGAGGCAGGGCTGCCATATGTGGCAAGTACCTCTTCAACTGGGCAGTAAGAAC
         ::    ::  ::  :    ::  ::::::::::: :: :::::::::::::::: :  :::
AY6510  ATCCCAGGGGGGGAAAGCCGCCATATGCGGTAAGTACCTCTTCAACTGGGCGGTGAAAAC
         2880      2890      2900      2910      2920      2930

2940      2950      2960      2970      2980      2990
HCV1    AAAGCTCAAACTCACTCCAATAGCGGCCGCTGGCCAGCTGGACTTGTCCGGCTGGTTCAC
        ::  :::::::::: :: :: :::    ::    :::::::::  ::::::::::::::::
AY6510  CAAACTCAAACTCATTCCATTACCGCTCGCGTCTCATTTGGACTTGTCCAATTGGTTCAC
         2940      2950      2960      2970      2980      2990

3000      3010      3020      3030      3040      3050
HCV1    GGCTGGCTACAGCGGGGGAGACATTTATCACAGCGTGTCTCATGCCCGGCCCCGCTGGAT
        ::    :::::::::::::::::::::::::::::::::::::::::::::::: :::  :
AY6510  GGGCGGCTACAGCGGGGGAGACATTTATCACAGCGTGTCTCATGCCCGGCCCCGTTGGTT
         3000      3010      3020      3030      3040      3050

3060      3070      3080      3090      3100      3110
HCV1    CTGGTTTTGCCTACTCCTGCTTGCTGCAGGGGTAGGCATCTACCTCCTCCCCAACCGA
        :          ::::::::::: ::  : : ::::::::::::::::::::: ::::::::
AY6510  TCTCTGGTGCCTACTCCTACTCTCAGTAGGGGTAGGCATCTACCTCCTTCCCAACCGA
         3060      3070      3080      3090      3100      3110
```

Fig: 19

```
              10        20
HCV1    GAAGGTTGGGGTAAACACTCC-GGCCT
        ::  ::::::::  ::  :::::::   :::::
AY6510  GACGGTTGGGC-AACCACTCCAGGCCT
              10        20
```

Fig 20

```
              10        20        30        40        50        60
HCV1    MSTNPKPQKKNKRNTNRRPQDVKFPGGGQIVGGVYLLPRRGPRLGVRATRKTSERSQPRG
        ::::::::::..:::::::::::::::::::::::::::::::::::::::::::::::::
Ay6510  MSTNPKPQRKTKRNTNRRPQDVKFPGGGQIVGGVYLLPRRGPRLGVRATRKTSERSQPRG
```

Fig. 20 continued

```
                 10        20        30        40        50        60
              70        80        90       100       110       120
HCV1   RRQPIPKARRPEGRTWAQPGYPWPLYGNEGCGWAGWLLSPRGSRPSWGPTDPRRRSRNLG
       ::::::::::::::::::::::::::::::::::::::::::::::::::::::::::::
Ay6510 RRQPIPKARRPEGRTWAQPGYPWPLYGNEGCGWAGWLLSPRGSRPSWGPTDPRRRSRNLG
              70        80        90       100       110       120

130       140       150       160       170       180
HCV1   KVIDTLTCGFADLMGYIPLVGAPLGGAARALAHGVRVLEDGVNYATGNLPGCSFSIFLLA
       :::::::.::::::::::::::::::::::::::::::::::::::::::::::::::::
Ay6510 KVIDTLTYGFADLMGYIPLVGAPLGGAARALAHGVRVLEDGVNYATGNLPGCSFSIFLLA
             130       140       150       160       170       180

190
HCV1   LLSCLTVPASA
       :::::::::::
Ay6510 LLSCLTVPASA
             190
```

Fig 21

```
                 10        20        30        40        50        60
HCV1   VRNSTGLYHVTNDCPNSSIVYEAADAILHTPGCVPCVREGNASRCWVAMTPTVATRDGKL
       ::::.:.:::::::::.:.:::.  .  :.:  :::::::::::..::::::...:::..  .
Ay6510 VRNSSGVYHVTNDCPNASVVYETDSLIIHLPGCVPCVREGNGSRCWVSLSPTVAAKDPGV
              10        20        30        40        50        60

70        80        90       100       110       120
HCV1   PATQLRRHIDLLVGSATLCSALYVGDLCGSVFLVGQLFTFSPRRHWTTQGCNCSIYPGHI
       :....:::.:..:.:::.::.:::  ::::::::::::::::::.:::::::::  :::::::::.
Ay6510 PVNEIRRHVDLIAGAAAFCSAMYVGHLCGSIFLVGQLFTLSPRRHWTTQDCNCSIYPGHV
              70        80        90       100       110       120

130       140       150       160       170       180
HCV1   TGHRMAWDMMMNWSPTTALVMAQLLRIPQAILDMIAGAHWGVLAGIAYFSMVGNWAKVLV
       ::::::::::::::::::::::.::::::::::::::::::::::::::::::::.::::
Ay6510 TGHRMAWDMMMNWSPTTALVVAQLLRIPQAILDMIAGAHWGVLAGIAYFSMVGNWTKVLV
             130       140       150       160       170       180

190
HCV1   VLLLFAGVDA
       ::::::::::
Ay6510 VLLLFAGVDA
             190
```

Fig 22

```
                 10        20        30        40        50        60
E2     THVTGGSAGHTVSGFVSLLAPGAKQNVQLINTNGSWHLNSTALNCNDSLNTGWLAGLFYH
       : :..:::....:.:.:.::.::::::.:::::::::::.: ::::::::::.:::::::.
Ay6510 TIVSGGSAGRSTAGLVGLFSPGARQNIQLINTNGSWHINRTALNCNDTLQTGWVAGLFYT
              10        20        30        40        50        60
```

Fig. 22 continued

```
              70         80         90        100        110        120
E2      HKFNSSGCPERLASCRPLTDFDQGWGPISYANGSGPDQRPYCWHYPPKPCGIVPAKSVCG
        .:::::::::::::::::.:::::::::::::::::.:::::::::::::::::.::::
Ay6510  NKFNSSGCPERLASCRPLADFDQGWGPISYTNGSGPDQRPYCWHYPPKPCGIVPAESVCG
              70         80         90        100        110        120

130        140        150        160        170        180
E2      PVYCFTPSPVVVGTTDRSGAPTYSWGENDTDVFVLNNTRPPLGNWFGCTWMNSTGFTKVC
        :::::::::::::::::::::::::::.:::::.:::::::::: :::::: ::::::::::::
Ay6510  PVYCFTPSPVVVGTTDRSGAPTYNWGENETDVFVLNNTRPRLGNWFGGTWMNSTGFTKVC
             130        140        150        160        170        180

190        200        210        220        230        240
E2      GAPPCVIGGAGNNTLHCPTDCFRKHPDATYSRCGSGPWITPRCLVDYPYRLWHYPCTINY
        ::::::.:::.:::::::::::::::::::.::::::::::::::. ::::::::::::::
Ay6510  GAPPCAIGGVGNNTLYCPTDCFRKHPEATYSRCGSGPWITPRCLIHYPYRLWHYPCTINY
             190        200        210        220        230        240

250        260        270        280        290        300
E2      TIFKIRMYVGGVEHRLEAACNWTRGERCDLEDRDRSELSPLLLTTTQWQVLPCSFTTLPA
        :::::::.:::::::::.:::::::::::::.::::.:::::::.::::::::::::::::
Ay6510  TIFKIRMFVGGVEHRLDAACNWTRGERCDLDDRDRAELSPLLLSTTQWQVLPCSFTTLPA
             250        260        270        280        290        300

310        320        330        340        350        360
E2      LSTGLIHLHQNIVDVQYLYGVGSSIASWAIKWEYVVLLFLLLADARVCSCLWMMLLISQA
        ::::::::::::::::::::::...:..::.:::::::::::::::::.::::::::::.
Ay6510  LSTGLIHLHQNIVDVQYLYGLSSAVTSWVIKWEYVVLLFLLLADARICACLWMMLLISQV
             310        320        330        340        350        360

370        380        390        400        410        420
E2      EAALENLVILNAASLAGTHGLVSFLVFFCFAWYLKGKWVPGAVYTFYGMWPLLLLLLALP
        ::::::..:::::::.::::::.:  ..:::   :::::::::.::  .:.  :::::::::::
Ay6510  EAALENLIVLNAASLVGTHGIVPFFIFFCAAWYLKGKWAPGLAYSVYGMWPLLLLLLALP
             370        380        390        400        410        420

E2      QRAYA
        :::::
Ay6510  QRAYA
```

Fig 23

```
              10         20         30         40         50         60
HCV1    LDTEVAASCGGVVLVGLMALTLSPYYKRYISWCLWWLQYFLTRVEAQLHVWIPPLNVRGG
        ::  :.::::....  :  .::::::::.::..   .::::::.:: :.::.:::::.:::
Ay6510  LDQELAASCGATVFICLAVLTLSPYYKQYMARGIWWLQYMLTRAEALLQVWVPPLNARGG
              10         20         30         40         50         60

70         80         90        100        110        120
HCV1    RDAVILLMCAVHPTLVFDITKLLLAVFGPLWILQASLLKVPYFVRVQGLLRFCALARKMI
        ::.:..:::  :...::  :.::..:..:::::::::::::::::::::::::.:::::::.
Ay6510  RDGVVLLTCVLHPHLLFEITKIMLAILGPLWILQASLLKVPYFVRVQGLLRICALARKMV
              70         80         90        100        110        120
```

Fig. 23 continued

```
                130       140       150       160       170       180
HCV1    GGHYVQMVIIKLGALTGTYVYNHLTPLRDWAHNGLRDLAVAVEPVVFSQMETKLITWGAD
        ::::::::  :::::::::.::::::::::::::.:::::::::::::::::::::::::
Ay6510  GGHYVQMVTIKLGALTGTYIYNHLTPLRDWAHNGLQDLAVAVEPVVFSQMETKLITWGAD
                130       140       150       160       170       180

190
HCV1    TAACGDIINGLPVSARR
        :::::::::::::::::
Ay6510  TAACGDIINGLPVSARR
                190
```

Fig 24:

```
                10        20        30        40        50        60
HCV1    GREILLGPADGMVSKGWRLLAPITAYAQQTRGLLGCIITSLTGRDKNQVEGEVQIVSTAA
        : .:::::::::::.: :::::::::::::::::::::::::::::::::::::::::::
Ay6510  GQEILLGPADGMASRGWRLLAPITAYAQQTRGLLGCIITSLTGRDKNQVEGEVQIVSTAA
                10        20        30        40        50        60

70        80        90       100       110       120
HCV1    QTFLATCINGVCWTVYHGAGTRTIASPKGPVIQMYTNVDQDLVGWPAPQGSRSLTPCTCG
        ::::::::::::::::::::::::::: ::::: ::::::::: ::  :::  ::: ::
Ay6510  QTFLATCINGVCWTVYHGAGTRTIASSKGPVILMYTNVDQDLGGWTAPQVLGSLTPWSCG
                70        80        90       100       110       120

130       140       150       160       170       180
HCV1    SSDLYLVTRHADVIPVRRRGDSRGSLLSPRPISYLKGSSGGPLLCPAGHAVGIFRAAVCT
        ::::::::::::::::::::.:::.:::::::::::::::::::::: ::::::::::::
Ay6510  SSDLYLVTRHADVIPVPRRGETRGSLLSPRPISYLKGSSGGPLLCPMGHAVGIFRAAVCT
                130       140       150       160       170       180

190       200       210       220       230       240
HCV1    RGVAKAVDFIPVENLETTMRSPVFTDNSSPPVVPQSFQVAHLHAPTGSGKSTKVPAAYAA
        :::::::::.:::::::::::::::::::.:::::::.::::::::::::::::::::::
Ay6510  RGVAKAVDFVPVESLETTMRSPVFTDNSSPLTVPQSYQVAHLHAPTGSGKSTKVPAAYAA
                190       200       210       220       230       240

250       260       270       280       290       300
HCV1    QGYKVLVLNPSVAATLGFGAYMSKAHGIDPNIRTGVRTITTGSPITYSTYGKFLADGGCS
        :::::::::::::::::::::::::::::::::::::::::::::::::::::::::::
Ay6510  QGYKVLVLNPSVAATLGFGAYMSKAHGIDPNIRTGVRTITTGSPITYSTYGKFLADGGCP
                250       260       270       280       290       300

310       320       330       340       350       360
HCV1    GGAYDIIICDECHSTDATSILGIGTVLDQAETAGARLVVLATATPPGSVTVPHPNIEEVA
        ::::::::::::::.:::::::::::::::::::.:: ::::::::::::::::.:::::
Ay6510  GGAYDIIICDECHSVDATSILGIGTVLDQAETAGVRLTVLATATPPGSVTVPHSNIEEVA
                310       320       330       340       350       360

370       380       390       400       410       420
HCV1    LSTTGEIPFYGKAIPLEVIKGGRHLIFCHSKKKCDELAAKLVALGINAVAYYRGLDVSVI
        :::. :::::::::::::::. :::::::::::::::::::::::. :.:::.::::::::
Ay6510  LSADGEIPFYGKAIPLNYIKGGRHLIFCHSKKKCDELAAKLVGPGVNAVAFYRGLDVSVI
                370       380       390       400       410       420
```

Fig. 24 continued

```
              430        440        450        460        470        480
HCV1    PTSGDVVVVATDALMTGYTGDFDSVIDCNTCVTQTVDFSLDPTFTIETITLPQDAVSRTQ
        ::.::::::::::::::::::.::::::::::::.::::::::: :..::: :.:::::::.:
Ay6510  PTTGDVVVVATDALMTGFTGDFDSVIDCNTCVVQTVDFSLDPIFSIETSTVPQDAVSRSQ
              430        440        450        460        470        480

490        500        510        520        530        540
HCV1    RRGRTGRGKPGIYRFVAPGERPSGMFDSSVLCECYDAGCAWYELTPAETTVRLRAYMNTP
        ::::::::::  ::::..:::::::::::: ::::::::::::::::::::::::::.:::
Ay6510  RRGRTGRGKHGIYRYVSPGERPSGMFDSVVLCECYDAGCAWYELTPAETTVRLRAYLNTP
              490        500        510        520        530        540

550        560        570        580        590        600
HCV1    GLPVCQDHLEFWEGVFTGLTHIDAHFLSQTKQSGENLPYLVAYQATVCARAQAPPPSWDQ
        :::::::::::::: :::::::::::::::::::::::.:::::::::::::.:::::::
Ay6510  GLPVCQDHLEFWESVFTGLTHIDAHFLSQTKQSGENFPYLVAYQATVCARARAPPPSWDQ
              550        560        570        580        590        600

610        620        630        640        650
HCV1    MWKCLIRLKPTLHGPTPLLYRLGAVQNEITLTHPVTKYIMTCMSADLEVVT
        :::::::::: : :::::::::.::::::.::::::::.:.::.::::::::
Ay6510  MWKCLIRLKPTLTGATPLLYRLGSVQNEITLTHPITQYIMACMSADLEVVT
              610        620        630        640        650
```

Fig 25

```
              10         20         30         40         50         60
HCV1    STWVLVGGVLAALAAYCLSTGCVVIVGRVVLSGKPAIIPDREVLYREFDEMEECSQHLPY
        ::::::::::::::::::::::: ::::::::.::::::.::::::::::::::::. :.::
Ay6510  STWVLVGGVLAALAAYCLSTGSVVIVGRIILGGKPAVIPDREVLYREFDEMEECAAHVPY
              10         20         30         40         50         60

70         80         90         100        110        120
HCV1    IEQGMMLAEQFKQKALGLLQTASRQAEVIAPAVQTNWQKLETFWAKHMWNFISGIQYLAG
        .::::  :::::::::::::::::::.:.:.:  ::.::.::::.::::::::.:::::::::
Ay6510  LEQGMHLAEQFKQKALGLLQTASKQTETITPIVQSNWQKLESFWAKHMWNFVSGIQYLAG
              70         80         90         100        110        120

130        140        150        160        170        180
HCV1    LSTLPGNPAIASLMAFTAAVTSPLTTSQTLLFNILGGWVAAQLAAPGAATAFVGAGLAGA
        :::::::::::::::.::::::::::::.:::::::::::::.::::::.::::::::..::
Ay6510  LSTLPGNPAIASLMSFTAAVTSPLTTQQTLLFNILGGWLAAQLAAPAAATAFVGAGITGA
              130        140        150        160        170        180

190        200        210        220        230        240
HCV1    AIGSVGLGKVLIDILAGYGAGVAGALVAFKIMSGEVPSTEDLVNLLPAILSPGALVVGVV
        ..:::::::::::::.:::::::::::::::::::::.:.::::::::::::::::::::..::
Ay6510  VVGSVGLGKVLVDILAGYGAGVAGALVAFKIMSGETPTTEDLVNLLPAILSPGALVVAVV
              190        200        210        220        230        240

250        260        270        280        290        300
HCV1    CAAILRRHVGPGEGAVQWMNRLIAFASRGNHVSPTHYVPESDAAARVTAILSSLTVTQLL
        ::::::::::: :::::::::::::::::::::::::::::::::: :::. ::. :::::::
Ay6510  CAAILRRHVGLGEGAVQWMNRLIAFASRGNHVSPTHYVPESDASARVTPILTRLTVTQLL
```

Fig. 25 continued

```
                  250       260       270       280       290       300
            310
HCV1    RRLHQWISSECTTPC
        . ::  :::::.: .::
Ay6510  KGLHVWISSNCIAPC
            310
```

Fig 26

```
            10        20        30        40        50        60
HCV1    SGSWLRDIWDWICEVLSDFKTWLKAKLMPQLPGIPFVSCQRGYKGVWRVDGIMHTRCHCG
        ..::.:..:.:::::::.:::::::.::::::::::::::::::.:::  .::.::::  ::
Ay6510  ASSWLKDVWNWICEVLSDFKNWLKAKLVPQLPGIPFVSCQRGYRGVWRGEGIVHTRCPCG
            10        20        30        40        50        60

70        80        90        100       110       120
HCV1    AEITGHVKNGTMRIVGPRTCRNMWSGTFPINAYTTGPCTPLPAPNYTFALWRVSAEEYVE
        :.::::::::.::::::.:: : :.::::::::::::: :::::::::::::::::::::
Ay6510  ANITGHVKNGSMRIVGPKTCSNTWRGSFPINAYTTGPCTPSPAPNYTFALWRVSAEEYVE
            70        80        90        100       110       120

130       140       150       160       170       180
HCV1    IRQVGDFHYVTGMTTDNLKCPCQVPSPEFFTELDGVRLHRFAPPCKPLLREEVSFRVGLH
        .:..:::::::::.:::::::::::::::::: ::.:::::::.:::::::::.::.: ..
Ay6510  VRRLGDFHYVTGVTTDKLKCPCQVPSPEFSTEVDGVRLHRYAPPCKPLLRDEVTFSVGFN
            130       140       150       160       170       180

190       200       210       220       230       240
HCV1    EYPVGSQLPCEPEPDVAVLTSMLTDPSHITAEAAGRRLARGSPPSVASSSASQLSAPSLK
        ::  :::::::::::::.:::::::::::::::.:.:::: ::::.::::::::::::::
Ay6510  EYLVGSQLPCEPEPDVAALTSMLTDPSHITAKTAARRLKRGSPPSLASSSASQLSAPSLK
            190       200       210       220       230       240

250       260       270       280       290       300
HCV1    ATCTANHDSPDAELIEANLLWRQEMGGNITRVESENKVVILDSFDPLVAEEDEREISVPA
        ::::..::::::.:::::::::::.::::::::::::::.:::::::::::::::::::.:
Ay6510  ATCTTHHDSPDADLIEANLLWRREMGGNITRVESENKIVVLDSFDPLVAEEDDREISIPA
            250       260       270       280       290       300

310       320       330       340       350       360
HCV1    EILRKSRRFAQALPVWARPDYNPPLVETWKKPDYEPPVVHGCPLPPPKSPPVPPPRKKRT
        :::::  ..: :.::::::::::::::: :: ::  .::::::::::  :::::::::::
Ay6510  EILRKFKQFPPAMPIWARPDYNPPLVEPWKRPDCDPPLVHGCPLPPPKPTPVPPPRKKRT
            310       320       330       340       350       360

370       380       390       400       410       420
HCV1    VVLTESTLSTALAELATRSFGSSSTSGITGDNTTTSSEPAPSGCPPDSDAESYSSMPPLE
        :::  ::::.:::::::.::.::::::::.... ::         :.:::::::::::::
Ay6510  VVLDESTVSSALAELATKTFGSSTTSGVTSGEAAESSPALSCDGELDSEAESYSSMPPLE
            370       380       390       400       410       420

430       440       450       460       470       480
HCV1    GEPGDPDLSDGSWSTVSSEANAEDVVCCSMSYSWTGALVTPCAAEEQKLPINALSNSLLR
        ::::::::::::::::::::...::::::::::::::::::::::::::::::::::::
```

Fig. 26 continued

```
Ay6510  GEPGDPDLSDGSWSTVSSDGGTEDVVCCSMSYSWTGALITPCAAEETKLPINALSNSLLR
               430       440       450       460       470       480

490       500       510       520       530       540
HCV1    HHNLVYSTTSRSACQRQKKVTFDRLQVLDSHYQDVLKEVKAAASKVKANLLSVEEACSLT
        ::::::::::::: .::::::::::::.::.:::::.:: :: :::.:::::::::::
Ay6510  HHNLVYSTTSRSAGKRQKKVTFDRLQVLDDHYRDVLKEAKAKASTVKAKLLSVEEACSLT
               490       500       510       520       530       540

550       560       570       580       590       600
HCV1    PPHSAKSKFGYGAKDVRCHARKAVTHINSVWKDLLEDNVTPIDTTIMAKNEVFCVQPEKG
        :::::.:::::::  ::::  :.   ::. ::::::.::::::.:::::::::::. :::
Ay6510  PPHSARSKFGYGPKDVRSHSSKAIRHINSVWQDLLEDNTTPIDTTIMAKNEVFCVKAEKG
               550       560       570       580       590       600

610       620       630       640       650       660
HCV1    GRKPARLIVFPDLGVRVCEKMALYDVVTKLPLAVMGSSYGFQYSPGQRVEFLVQAWKSKK
        :::::::::: .:::::::::::: :::::: .:. :::: :::::::::.::.. :::::
Ay6510  GRKPARLIVYPDLGVRVCEKRALYDVVKQLPIAVMGPSYGFQYSPAQRVDFLLNAWKSKK
               610       620       630       640       650       660

670       680       690       700       710       720
HCV1    TPMGFSYDTRCFDSTVTESDIRTEEAIYQCCDLDPQARVAIKSLTERLYVGGPLTNSRGE
        .:::::::::::::::::.::: .:: :.:.::.::::::::::::::::::::::::..
Ay6510  NPMGFSYDTRCFDSTVTEADIRTEEDLYQSCDLVPEARAAIRSLTERLYIGGPLTNSKGQ
               670       680       690       700       710       720

730       740       750       760       770       780
HCV1    NCGYRRCRASGVLTTSCGNTLTCYIKARAACRAAGLQDCTMLVCGDDLVVICESAGVQED
        :::::::::::::::::::::.:::.:: :::::: :::::::::::::::::::.::
Ay6510  NCGYRRCRASGVLTTSCGNTITCYLKASAACRAAKLQDCTMLVCGDDLVVICESAGVKED
               730       740       750       760       770       780

790       800       810       820       830       840
HCV1    AASLRAFTEAMTRYSAPPGDPPQPEYDLELITSCSSNVSVAHDGAGKRVYYLTRDPTTPL
        :::::::::::::::.:::::::.:::::::::::::::::::.:::.::::::.: :::
Ay6510  AASLRAFTEAMTRYSGPPGDPAQPEYDLELITSCSSNVSVARDGAGQRVYYLTREPETPL
               790       800       810       820       830       840

850       860       870       880       890       900
HCV1    ARAAWETARHTPVNSWLGNIIMFAPTLWARMILMTHFFSVLIARDQLEQALDCEIYGACY
        ::::::::::::::::::::::::::::.::.::::.:.:::..::::::::::::::.
Ay6510  ARAAWETARHTPVNSWLGNIIMFAPTLWVRMVLMTHLFSILIVQEHLEKALDCEIYGATH
               850       860       870       880       890       900

910       920       930       940       950       960
HCV1    SIEPLDLPPIIQRLHGLSAFSLHSYSPGEINRVAACLRKLGVPPLRAWRHRARSVRARLL
        :. ::::: ::::::::::::::::::::::::::.:::::::::::::::::::::.::
Ay6510  SVPPLDLPEIIQRLHGLSAFSLHSYSPGEINRVASCLRKLGVPPLRAWRHRARSVRATLL
               910       920       930       940       950       960

970       980       990       1000      1010      1020
HCV1    ARGGRAAICGKYLFNWAVRTKLKLTPIAAAGQLDLSGWFTAGYSGGDIYHSVSHARPRWI
        ..:::::::::::::::::.::::::.: :...:.::.:::::::::::::::::::::.
Ay6510  SQGGKAAICGKYLFNWAVKTKLKLIPLPLASHLDLSNWFTGGYSGGDIYHSVSHARPRWF
               970       980       990       1000      1010      1020
```

Fig. 26 continued

```
                    1030
HCV1     WFCLLLLAAGVGIYLLPNR
         .:::::..::::::::::
Ay6510   LWCLLLLSVGVGIYLLPNR
                    1030
```

Fig: 27

The sequence of the primers for the 5'UTR region were:

SEQ ID No. 19 HCV -1F : 5' - GCC AGC CCCCTG ATG GGG G 3'

SEQ ID No. 20 HCV-383R: 5' - gtt tag gat tcg tgc tca tgg tgc 3'

The sequence of the primers for the Core region were:

SEQ ID No. 21 HCV – 340F: 5' gaccgtgcaccatgagcacgaatcc 3'

SEQ ID No. 22 HCV – 920R: 5' tcc gac ggc cga agc ggg ca 3'

The sequence of the primers for the E1 region were:

SEQ ID No. 23 HCV- 837F: 5' ccc ggt tgc tct ttc tct atc ttc 3'

SEQ ID No. 24 HCV-1262R: 5' gga tag atg gag caa ttg cag tct tg 3'

The sequence of the primers for the E1 and E2 region were:

SEQ ID No. 25 HCV-1233F: 5' caa gac tgc aat tgc tcc atc tat c 3'

SEQ ID No. 26 HCV-2248R: 5' agc ctg tgc tcg acc ccc ccc aca tac atc ct 3's

The sequence of the primers for the E2 and NS1 region were:

SEQ ID No. 27 HCV-2010F: 5' caa ctgg attc acc aag gtg 3'

SEQ ID No. 28 HCV-3040R: 5' gca gac tgg cct gca aga tc 3'

The sequence of the primers for the NS2 and NS3 region were:

SEQ ID No. 29 HCV-3000F: 5' aca tca cca aaa tca tgc t 3'

SEQ ID No. 30 HCV-4040R: 5' ccc agt ggg tgc gta atg 3'

The sequence of the primers for the NS3 region were:

SEQ ID No. 31 HCV-3891F - 5' cgc gga tcc gtg tgc acc cgt ggg gtt gca aag 3'

SEQ ID No. 32 HCV-5315R: 5' cga ggc ttc tag cta gtg acg acc tcc agg tcc gc 3'

The sequence of the primers for the NS4 region were:

SEQ ID No. 33 HCV-5477F: 5' cgc gga tcc gcc cac gtc ccc tac ctc gag cag 3'

SEQ ID No. 34 HCV-6260R: 5' cga agc ttc taa gca cac ggg gcg atg caa tcc ga 3'

The sequence of the primers for the NS5A region were:

SEQ ID No. 35 HCV-6281F: 5' ctg gga ctg gat atg cga ggt gct gag cg 3'

SEQ ID No. 36 HCV-7405R: 5' gag ctg cca agg tct tag tgg caa gct c 3'

Fig. 27 continued

The sequence of the primers for the NS5B region were:

SEQ ID No. 37 HCV – 7200F: 5` tat ggg cac ggc cgg att at 3`

SEQ ID No. 38 HCV – 8030R: 5` ttc att ctt ggc cat gat ggt a 3`

The sequence of the primers for the NS5B and 3`UTR region were:

SEQ ID No. 39 HCV-8000F: 5` ata gac act acc atc atg gcc a 3`

SEQ ID No. 40 HCV – 9414: 5`acg ggg cct aaa ggc ctg gag 3`

HEPATITIS C VIRUS VACCINE

This nonprovisional application claims the benefit of U.S. Provisional Application No. 60/689,090, filed Jun. 10, 2005.

FIELD OF INVENTION

The present invention relates to isolation of a novel Hepatitis C virus. More particularly, the present invention relates to a viral class Hepatitis C, polypeptides, polynucleotide, vaccine and antibodies derived there from.

BACKGROUND OF THE INVENTION

Viral hepatitis, caused by the six hepatotropic viruses, viz., hepatitis A virus (HAV) hepatitis B virus (HBV), Hepatitis D virus (HDV), hepatitis E virus (HEV) and hepatitis G virus (HGV), represents a major health problem world wide. Hepatitis B Virus (HBV) and Hepatitis C Virus (HCV) are the major cause of devastating liver diseases all over the world. Recent estimates indicate that more than 500 million people appeared to have been infected by these liver-tropic viruses. With about 180 million people currently infected worldwide, HCV represents a daunting public health problem. Out of these, at least 15-20 million in India and about 4 million people in the USA suffer from chronic infection by HCV. In some countries like Egypt about 10 to 15 per cent of general population appears to carry HCV. More than 30 to 40% of the infected people develop liver cirrhosis and/or hepatocellular carcinoma after suffering with chronic infection for a decade or two and therefore HCV infection is considered to be a silent killer. Although interferon a in combination with ribavirin work well with some patients infected by some genotypes, more than 50% of the patients are refractory to such treatment.

Non-A, Non-B hepatitis (NANBH) are transmissible diseases that are believed to be viral induced, and that are distinguishable from other forms of viral-associated liver diseases, including that caused by the known hepatitis viruses. Viral hepatitis, caused by the hepatotropic viruses, viz, hepatitis A virus (HAV) hepatitis B virus (HBV), Hepatitis D virus (HDV), hepatitis E virus (HEV) and hepatitis G virus (HGV), represents a major health problem world wide. Until recently there has been neither clarity nor agreement as to the identity or specificity of the antigen antibody systems associated with agents of NANBH. It is possible that NANBH is caused by more than one infectious agent and unclear what the serological assays detect in the serum of patients with NANBH.

In 1987, Houghton, et al. cloned the first virus definitively linked to NANBH. Houghton et al. described there in the cloning of an isolate from a new viral class, hepatitis C virus (HCV), the prototype isolate described therein being named "HCV 1". HCV is a Flavi-like virus, with an RNA genome. They described the production of recombinant proteins from HCV sequences that are useful as diagnostic reagents, as well as polynucleotides useful in diagnostics hybridization assays and in cloning of additional HCV isolates.

Hepatitis C virus (HCV) has emerged in recent years as the leading cause of worldwide blood-transmitted chronic hepatitis, liver cirrhosis, and hepatocellular carcinoma A vaccine to prevent HCV infection has not yet been available any where in the world and the existing antiviral treatments are ineffective in the majority of the HCV infected patients.

Despite significant progress in the field of biotechnology, reliable diagnostic procedures, an alternative animal model other than chimpanzee, efficient cell culture systems that can support long-term replication of the virus and effective therapeutic strategies are still lacking.

As with any disease, an accurate diagnosis of HCV infection is essential before patients are counseled and treatment is initiated. Since, the identification and molecular characterization of the HCV in 1989 by Choo and colleagues, a number of diagnostic tests based on the detection of either the anti HCV antibodies or HCV-RNA by PCR in patient sera have been developed.

Presently, a third generation ELISA that incorporates antigens from the Core, NS3, NS4 and NS5 proteins of HCV, representing about 60% of the total amino acid sequence of HCV polyprotein, is available in the market. Although, this ELISA is significantly sensitive, a major drawback of this assay is that it fails to differentiate between active and post infection cases. In addition to this, it is now well documented that the commercially available third generation ELISA can not be used to detect all the viral infections in Indian patients owing to genotype sequence variations.

It may be noted at this stage that the commercial $3^{rd}$ EIA is based on genotype 1 (other than Indian HCV strain) and genotype specific antibody response in this virus is now documented. Hepatitis, Cirrhosis and Hepatocellular carcinoma, caused by Hepatitis C Virus remain a global health problem and development of a vaccine to prevent this silent killer is of utmost priority. Every major country's goal is to produce a therapeutic vaccine for those 180 million people who are already infected by HCV and a preventive vaccine to eradicate future HCV infections. Just a few years ago, there was a lot of skepticism about the possibility of developing a viable vaccine for HCV. The situation, however, has changed in the last two to three years mainly because i) about 40 to 50% of the patients spontaneously recover from infection, implying that their immune system can fight off the virus; ii) infected chimpanzees (the only animal model available for HCV produced viremia) and convalescent humans are protected against the re-exposure; and iii) chronically infected patients improved their immune response and liver functions when the viral envelope protein E1 was administered as therapeutic vaccine.

Luckily for Hepatitis B, there is a preventive vaccine available in most of the countries; thus, future infections can be prevented. A therapeutic vaccine for HBV to boost the immunity of the infected people may be forthcoming. Unfortunately such a vaccine is not available for HCV any where in the world. Because of the propensity of the virus to undergo genetic variation, resulting in the evolution of quasispecies, a vaccine developed in the western countries will not be effective in India. For that matter, a vaccine developed against the strain(s) prevalent in Northern India may not be effective in South India. Therefore, controlling HCV infection is a challenging task. With the recent breakthroughs in research and development on HCV, there is a lot of optimism now about the development of at least a therapeutic and a potential preventive vaccine. The major problem, however, is that a single vaccine may not be suitable for every country as there are several different genotypes. In India genotypes 1 and 3 are more prevalent, which are quite different from genotypes existing in other regions of the world. Therefore, our major goal is to make the vaccine candidate proteins, E1 and E2 for both genotypes in yeast and/or animal cells and test for their efficacy as therapeutic and preventive vaccines. We already know the sequence of these genotypes and we have also completed cloning of the genes encoding E1 and E2 proteins. Now, the major goal of this project is to make these proteins in large quantities, purify and characterize, and carry out human trials.

There is an ever-increasing demand for sensitive and accurate tests for detection and screening of Hepatitis viral carriers. There is also a need for effective vaccines and therapeutic agents for preventing and treating viral hepatitis. Moreover, there is tremendous genetic variation among existing strains from each country and thus development of potential vaccines depend upon characterization of the strian (s) existing among Indian population.

To overcome the problems associated with the prior art, the applicant has cloned and sequenced the genome of a novel Indian strain of HCV. This sequence can be used to develop HCV antigens, diagnostic kits and therapeutic vaccines.

OBJECTS OF THE INVENTION

The principal objective of the present invention is to isolate a novel strain of Hepatitis C Virus from a pool of Indian patients.

Another objective of the present invention is to characterize the novel strain of Hepatitis C Virus.

Yet another objective of the present invention is to identify the polynucleotide sequence for the novel strain of Hepatitis C Virus.

Still another objective of the present invention is to identify the polypeptide sequence for the novel strain of Hepatitis C Virus.

Still another objective of the present invention is to identify the primers.

Still another objective of the present invention is to develop a therapeutic vaccine for immunizing a subject with Hepatitis C infection.

Still another objective of the present invention is to develop a kit for identifying a subject with Hepatitis C infection.

Still another objective of the present invention is to develop a method of diagnosing a patient with Hepatitis C infection.

Still another objective of the present invention is to immunize a subject with Hepatitis C infection.

SUMMARY OF THE INVENTION

New isolates of HCV has been characterized from different parts of the world have been implicated as NANBH carriers. These isolates exhibit nucleotide and amino acid sequence heterogeneity with respect to the prototype isolate HCV1, in several viral domains. It is believed that these distinct sequences are of in importance, particularly in diagnostic assays and in vaccine development.

The invention relates to a novel class of Hepatitis C virus that has been isolated and characterized from an Indian infected host. The entire genomic structure and the nucleotide sequence of the novel HCV isolate have been deduced. The genome appears to be single-stranded RNA comprising about 9442 nucleotides. When compared with all known viral sequences, several distinct domains and sequences that are of much importance clinically, particularly for diagnostic purposes and for vaccine development have been observed. The said sequence has been deposited at the GenBank at accession number AY651061. The said novel strain has been designated as Khajal.

Indian HCV isolate has been characterized from a chronic hepatitis C patient. Blood was collected form this patient, the RNA and cDNA was isolated and the PCR reaction was set up using specific primers. The PCR amplicons were cloned and sequenced. This isolate exhibits nucleotide and amino acid sequence heterogeneity with respective to prototype isolate in several viral domains. These distinct sequences are much in importance, particularly in diagnostic assays and in vaccine development.

In one aspect, the invention provides novel nucleotide sequences, obtained from the novel HCV strain resulting polynucleotide, polypeptides and antibodies derived there from. The invention also provides purified polypeptide sequences obtained from novel isolate, said sequence being distinct from that of currently known HCV isolates. The invention includes recombinant vectors comprising said sequences and host cells transformed with such vectors.

Further, the invention provides probes derived from the HCV cDNA useful for diagnose of the presence of HCV in samples, and to isolate naturally occurring variants of the virus.

The invention also provides antibodies, both polyclonal and monoclonal, directed against HCV epitopes contained within these polypeptide sequences are also useful for diagnostic tests, as therapeutic agents, for screening of antiviral agents.

Also included within scope of the invention is an monoclonal antibody directed against an HCV epitope and an anti-idiotype antibody comprising a region which mimics an HCV epitope.

Another aspect of the invention relates to kit for detection of HCV comprising: polynucleotides derived from the novel HCV isolate comprising a polynucleotide probe provided in a suitable container; an HCV antigen comprising an antibody directed against the HCV antigen to be detected, provided in a suitable container; antibodies directed against an HCV antigen comprising a polypeptide containing an HCV epitope present in the HCV antigen, provided in a suitable container.

Immunoassays are also included in the invention. These include an immunoassay for detecting an HCV antigen comprising incubating a sample suspected of containing an HCV antigen with a probe antibody directed against the HCV antigen to be detected under conditions which allow the formation of an antigen-antibody complex; and detecting an antigen-antibody complex containing the probe antibody. An immunoassay for detecting antibodies directed against an HCV antigen comprising incubating a sample suspected of containing anti-HCV antibodies with a probe polypeptide which contains an epitope of the HCV, under conditions which allow the formation of an antibody-antigen complex; and detecting the antibody-antigen complex containing the probe antigen.

Also included in the invention are vaccines for treatment of HCV infection comprising an immunogenic peptide containing an HCV epitope, or an inactivated preparation of HCV, or an attenuated preparation of HCV. These and other embodiments of the present invention will be readily apparent to those of ordinary skill in the art in view of the following description.

DETAILED DESCRIPTION OF THE INVENTION

The present invention is in relation to a hepatitis C virus polynucleotide sequence set forth in SEQ ID NO: 1 (FIG. 10) deposited at GenBank under accession number under AY 651061.

Yet another embodiment of the present invention, wherein said sequence is isolated from Indian patient pool.

The present invention relates to a Hepatitis C virus polypeptide sequence set forth in SEQ ID NO: 2 (as shown in FIG. 10).

The present invention also relates to a polynucleotide sequence as set forth in SEQ ID NO: 3, SEQ ID NO: 4, SEQ ID NO: 5, SEQ ID NO: 7, SEQ ID NO: 9, SEQ ID NO. 11, SEQ ID NO: 13, SEQ ID NO: 15, or SEQ ID NO: 17 encoding 5' untranslated region (UTR), 3' untranslated region (UTR), Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively.

The present invention further relates to a polypeptide sequence as set forth in SEQ ID No. 6, SEQ ID NO: 8, SEQ ID NO: 10, SEQ ID NO: 12, SEQ ID NO: 14, SEQ ID NO: 16 and SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively.

The present invention further relates to a hepatitis C virus strain isolated from a Hepatitis C virus infected Indian patient pool.

The present invention furthermore relates to a pair of primers having sequences set forth in SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and ID NOS: 39 and 40.

The present invention further relates to a vaccine for immunizing a subject against hepatitis C virus comprising at least one protein having a polypeptide sequence as set forth in SEQ ID NO: 6, SEQ ID NO: 8, SEQ ID NO: 10, SEQ ID NO: 12, SEQ ID NO: 14, SEQ ID NO: 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively optionally along with a pharmaceutically acceptable vaccine adjuvant.

Yet another embodiment of the present invention, wherein the subject is a mammal including humans.

In still another embodiment of the present invention, wherein said vaccine adjuvant is selected from a group comprising mineral salts (aluminium hydroxide and aluminium or calcium phosphate gels, oil emulsions and surfactant based formulations (MF59, micro-fluidized detergent stabilized oil-in-water emulsion)), particulate adjuvants (virosomes, polylactide co-glycolide, structured complex of saponins and lipids), microbial derivatives(-natural and synthetic), endogenous human immunomodulators (hGM-CSF or hIL-12, Immudaptin) and inert vehicles such as gold particles.

The present invention relates to a kit for identifying hepatitis C virus comprising at least one antigenic peptide selected from a polypeptide sequence as set forth in SEQ ID NO: 6, SEQ ID NO: 8, SEQ ID NO: 10, SEQ ID NO: 12, SEQ ID NO: 14, SEQ ID 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively, capable of reacting specifically with antibodies directed against said virus.

Yet another embodiment of the present invention, wherein said kit further comprises control standards and instructions for use of the kit.

The present invention relates to a method for detecting the presence of hepatitis C virus comprises contacting sera with at least one antigenic polypeptide selected from a polypeptide sequence as set forth in SEQ ID NO: 6, SEQ ID NO: 8, SEQ ID NO: 10, SEQ ID NO: 12, or SEQ ID NO: 14 , SEQ ID NO: 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively wherein formation of an immunogenic complex confirms detection of said virus.

The present invention relates to a method of immunization against hepatitis C virus in a subject in need thereof, wherein said method comprises administering a pharmaceutically effective immunizing dose of the vaccine.

BRIEF DESCRIPTION OF THE FIGS.

Figure 2:
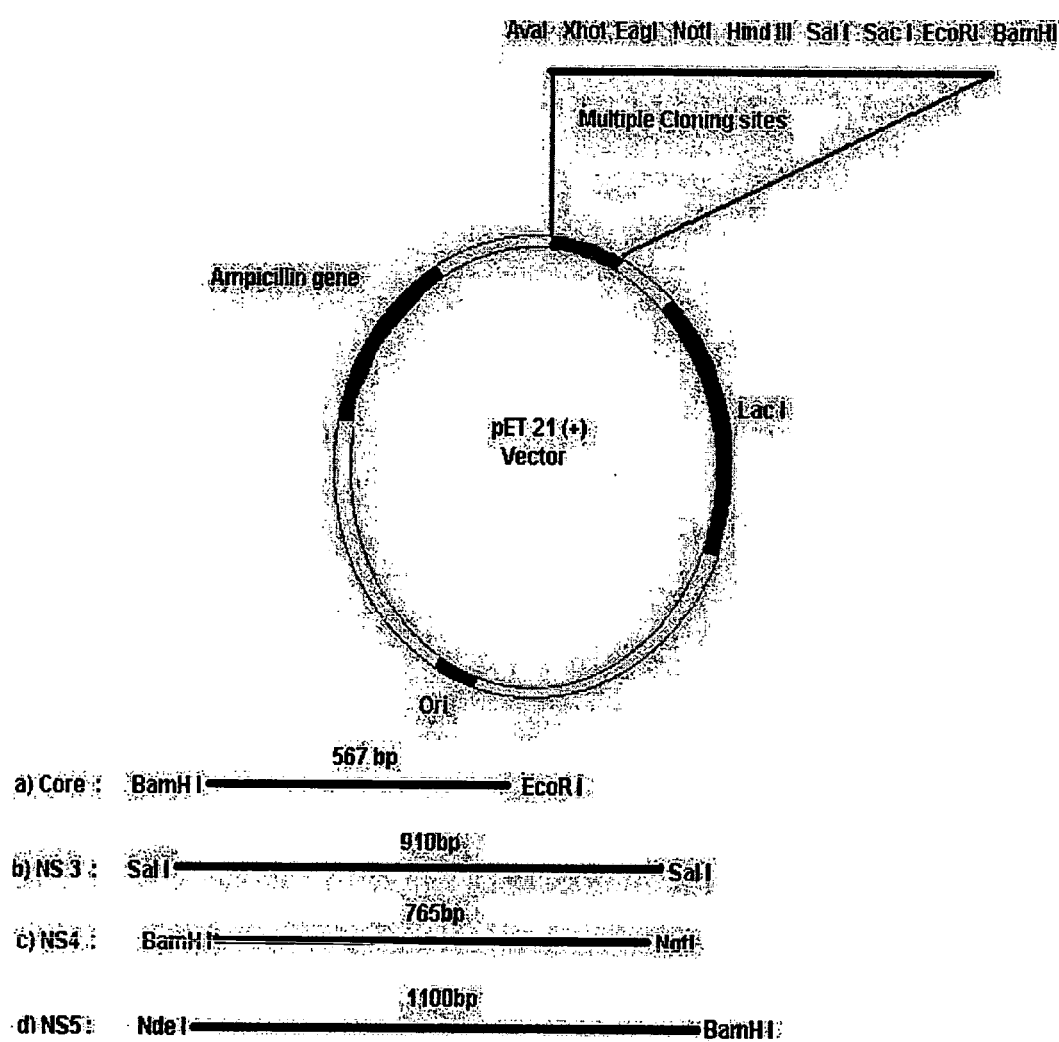
Figure 3:
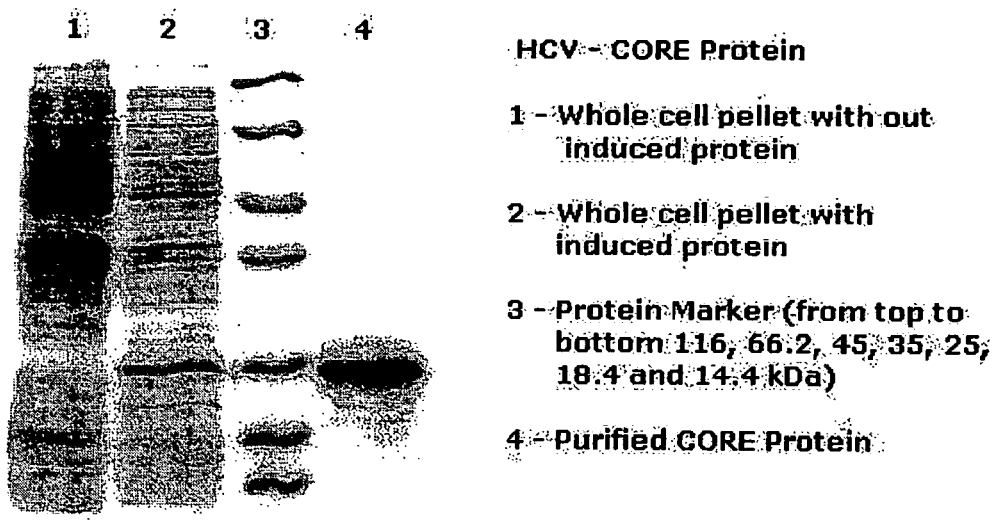

FIG. 1: Map of ORF of Hepatitis C virus isolate AY651061 and recombinant antigens FIG. 2: Hepatitis C virus isolate AY651061 restriction enzyme map FIG. 3: Photograph of the SDS PAGE gel for the core protein of HCV isolate AY651061

Figure 4:
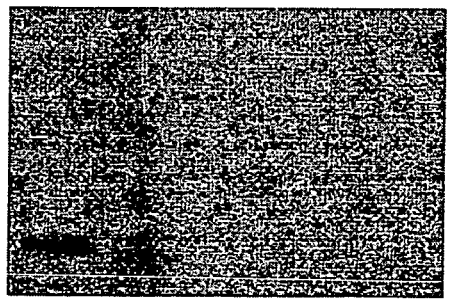

FIG. 4: Photograph of the Western Blot analysis showing the presence of the core protein of HCV isolate AY651061

Figure 5:
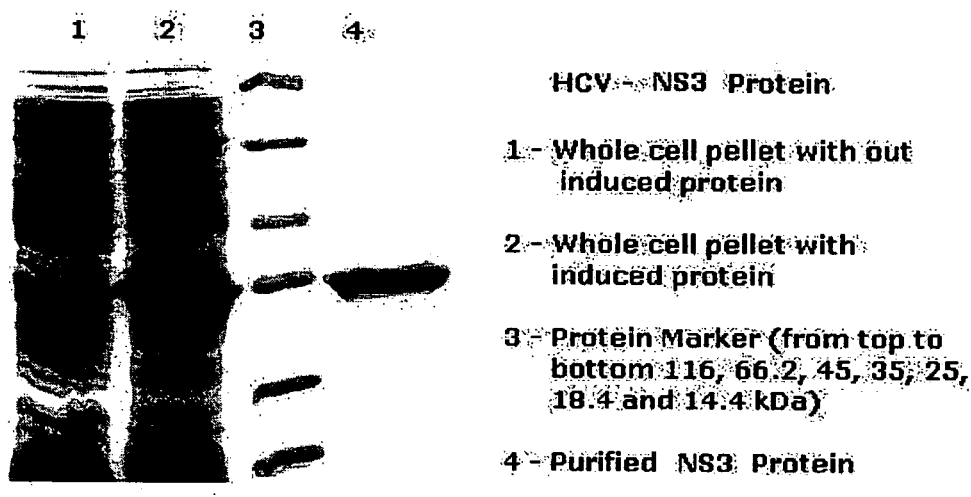

FIG. 5: Photograph of the SDS PAGE gel for the NS3 protein of HCV isolate AY651061

Figure 6:
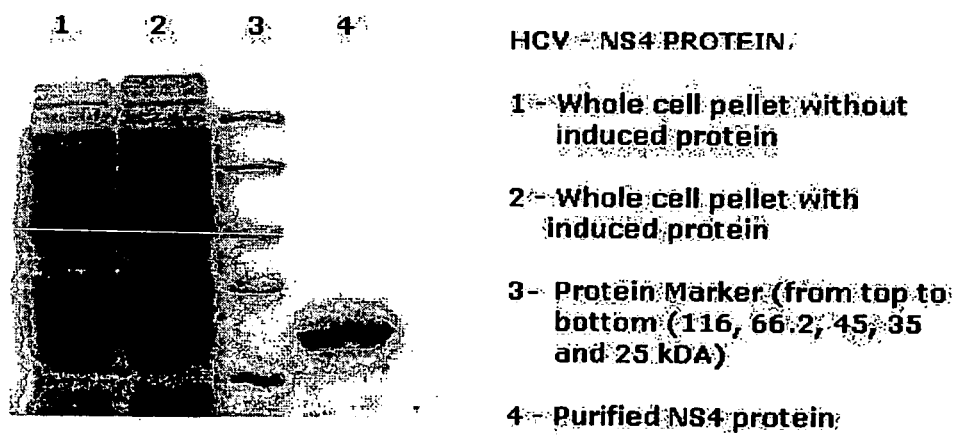

FIG. 6: Photograph of the SDS PAGE gel for the NS4 protein of HCV isolate AY651061

Figure 7:
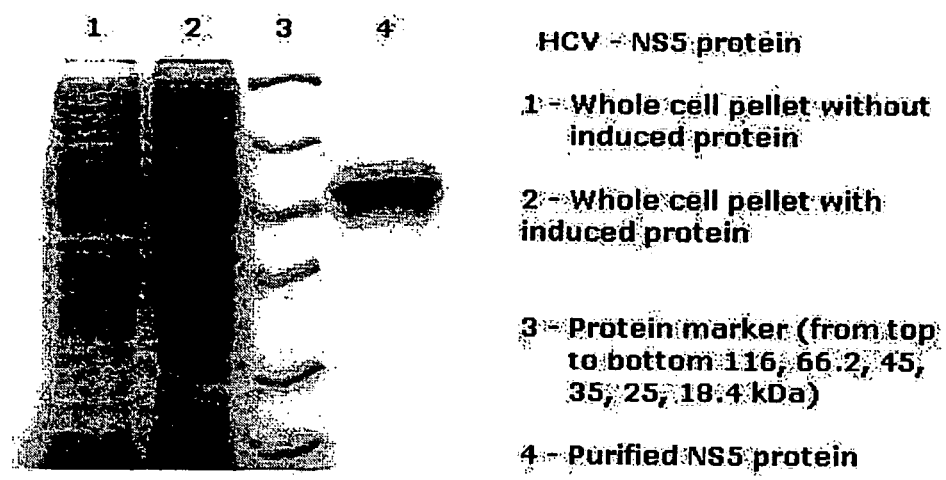

FIG. 7: Photograph of the SDS PAGE gel for the NS5 protein of HCV isolate AY651061

Figure 8:
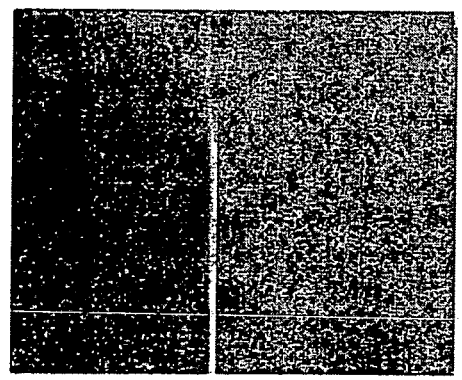

FIG. 8: Photograph of the Western blot analysis showing the presence of the NS5 protein of HCV isolate AY651061

FIG. 9: Nucleotide and polypeptide sequences of the HCV isolate AY651061 (SEQ ID NOS:3-18)

FIG. 10: Polypeptide and nucleotide sequences of the HCV isolate AY651061, complete sequence (SEQ ID NOS: 1 and 2)

FIG: 11: Nucleotide sequence comparison of HCV1 5' UTR (SEQ ID NO: 41) vs. AY651061 5' UTR (SEQ ID NO: 3)

FIG: 12: Nucleotide sequence comparison of HCV1 CORE (SEQ ID NO: 42) vs. AY651061 CORE (SEQ ID NO: 5)

FIG: 13: Nucleotide sequence comparison of HCV1 El (SEQ ID NO: 43) vs. AY651061 El (SEQ ID NO: 7)

FIG: 14: Nucleotide sequence comparison of HCV1 E2/NS1 (SEQ ID NO: 44) vs. AY651061 E2/NS1 (SEQ ID NO: 9)

FIG: 15: Nucleotide sequence comparison of HCV1 NS2 (SEQ ID NO: 45) vs. AY651061 NS2(SEQ ID NO: 11)

FIG: 16: Nucleotide sequence comparison of HCV1 NS3 (SEQ ID NO: 46) vs. AY651061 NS3 (SEQ ID NO: 13)

FIG: 17: Nucleotide sequence comparison of HCV1 NS4 (SEQ ID NO: 47) vs. AY651061 N54 (SEQ ID NO: 15)

FIG: 18: Nucleotide sequence comparison of HCV1 N55 (SEQ ID NO: 48) vs. AY651061 N55 (SEQ ID NO: 17)

FIG: 19: Nucleotide sequence comparison of HCV1 3 ' UTR (SEQ ID NO: 49) vs. AY651061 3 ' UTR (SEQ ID NO: 4)

FIG: 20: Amino acid comparison of HCV1 Core (SEQ ID NO: 50) vs. AY651061 Core (SEQ ID NO: 6)

FIG: 21: Amino acid comparison of HCV1 E1 (SEQ ID NO: 51) vs. AY651061 E1 (SEQ ID NO: 8)

FIG: 22: Amino acid comparison of HCV1 E2/NS1 (SEQ ID NO: 52) vs. AY651061 E2/NS1 (SEQ ID NO: 10)

FIG: 23: Amino acid comparison of HCV1 N52 (SEQ ID NO: 53) vs. AY651061 N52 (SEQ ID NO: 12)

FIG: 24: Amino acid comparison of HCV1 N53 (SEQ ID NO: 54) vs. AY651061 N53 (SEQ ID NO: 14)

FIG: 25: Amino acid comparison of HCV1 N54 (SEQ ID NO: 55) vs. AY651061 N54 (SEQ ID NO: 16)

FIG: 26: Amino acid comparison of HCV1 NS5 (SEQ ID NO: 56) vs. AY651061 NS5 (SEQ ID NO: 18)

FIG: 27: Nucleotide sequences for primers (SEQ ID NOS: 19-40)

The practice of the present invention will employ, unless otherwise indicated, conventional techniques of molecular biology, microbiology, recombinant DNA techniques and immunology, which are within the skill of the art. The term "hepatitis C virus" has been reserved by workers in the field for an unknown etiologic agent of NANBH. Accordingly, as used "hepatitis C virus" refers to an agent causative of NANBH, which was formerly referred to as NANBV and/or BB-NANBV from the class of the prototype isolate, HCV1 described by Houghton et al. HCV is a Flavi-like virus. The morphology and composition of flavivirus particle are known, and are discussed by Brinton (1986). Generally, with respect to morphology, Flaviviruses contain a central nucleocapsid surrounded by a lipid bilayer. Virions are spherical and have a diameter of about 40-50 nm. Their cores are about 25-30 nm in diameter. Along the outer surface of the virion envelope are projections that are about 5-10 nm long with terminal knobs about 2 nm in diameter.

In one of the embodiment, the HCV genome is comprised of RNA. It is known that RNA containing viruses have relatively high rates of spontaneous mutation, i.e., reportedly on the order of $10^{-3}$ to $10^{-4}$ per incorporated nucleotide. Therefore, there are multiple strains, which may be virulent or avirulent, within the HCV class of species. It is believed that the genome of HCV isolates is comprised of a single ORF of approximately 9,000 nucleotides to approximately 12,000 nucleotides encoding a polyprotein similar hydrophobic and antigenic character to that of HCV1. In addition, the genome is believed to be a positive stranded RNA.

Yet another embodiment comprises isolates of HCV comprise epitopes that are immunologically cross-reactive with epitopes in the HCV1 genome. At least some of these are epitopes unique to HCV when compared to other known Flaviviruses. the uniqueness of the epitope may be determined by its immunological reactivity with anti-HCV antibodies and lack of immunological reactivity with antibodies to other Flaviviruses species. Methods for determining immunological reactivity are known in the art, such as, for example, radioimmunoassay by ELISAs, hemagglutination, and the several examples of suitable techniques provided herein.

In still another embodiment it is expected that the overall homology of HCV isolates and HCV1 genomes at the nucleotide level probably will be about 40% or greater, probably about 60% or greater, and even more probably about 80% to about 90% or greater. In addition that there are many corresponding contiguous sequences of at least 13 nucleotides that are fully homologous. The correspondence between the sequence from a new isolate and the HCV1 sequence can be determined by techniques known in the art. For example they can be determined by a direct comparison of the sequence information of the polynucleotide from the new isolate and HCV1 sequences. Alternatively homology can be determined by hybridization of the poly nucleotides under conditions which form stable duplexes between homologous regions.

In still another embodiment the evolutionary relationship strains or isolates of HCV the putative HCV strains or isolates are identifiable by their homology at the polypeptide level. Thus, new HCV isolates are expected to be more than about 40% homologous. probably more than about 70% homologous. and even more probably more than about 80% homologous, and possibly even more than about 90% homologous at the polypeptide level. The techniques for determining amino acid sequence homology are known in the art. For example, the amino acid sequence may be determined directly and compared to the sequences provided. Alternatively the nucleotide sequence of the genomic material of the putative HCV may be determined, the amino acid sequence encoded therein can be determined and the corresponding regions compared.

In still another embodiment the non-structural core and envelope domains of the polyprotein have been predicted for HCV1. The "C", or core, polypeptide is believed to be encoded from the 5' terminus to about nucleotide 345 of HCV1. The putative "E", or envelope, domain is believed to be encode from about nucleotid 346 to about nucleotide 1050. Putative NS1 or non-structural one domain, is thought to encoded from about nucleotide 1051 to about nucleotide 1953. For the remaining domains, putative NS2 is thought to be encoded from about nucleotide 1954 to about nucleotide 3018, putative NS3 from about nucleotide 3019 to about nucleotide, 4950, putative NS4 from about nucleotide 4951 to about nucleotide 6297, and putative NS 5 from about nucleotide 6298 to the 3' terminus.

In still another embodiment the portions of the cDNA sequences derived from HCV are useful as probes to diagnose the presence of virus in HCV infected individuals, and to isolate naturally occurring variants of the virus. These cDNAs also make available polypeptide sequences of HCV antigens encoded within the HCV genome(s) and permits the production of polypeptides which are useful as standards or reagents in diagnostic tests and are components as vaccines. Antibodies, including for example both polyclonal and monoclonal, directed against HCV epitopes contained within these polypeptide sequences are also useful for diagnostic tests, as therapeutic agents, for screening of antiviral agents, and for the isolation of the NANB virus agent which these cDNAs derive. In addition, by utilizing probes derived from these cDNSs it is possible to isolate and sequence other portions of the HCV genome, thus giving rise to additional probes and polypeptides which are useful in the diagnosis and/or treatment, both prophylactic therapeutic, of NANBH.

In still another embodiment it is with respect to polynucleotides, some aspects of the invention are: a purified HCV polynucleotide; a recombinant HCV polynucleotide; a recombinant polynucleotide comprising a sequence derived from an HCV genome or from HCV cDNA; a recombinant polynucleotide encoding—an epitope of HCV; a recombinant vector containing any of the above recombinant polynucleotides, and a host cell transformed with any of these vectors.

In still another embodiments of the invention: a recombinant expression system comprising an open reading frame (ORF) of DNA derived from an HCV genome or from HCV cDNA, wherein the ORF is operably linked to a control sequence compatible with a desired host, a cell transformed with the recombinant expression system, and a polypeptide produced by the transformed cell. Still other aspects of the invention are: a preparation of polypeptides from the purified HCV; a purified HCV polypeptide; a purified polypeptide comprising an epitope which is immunologically identifiable with an epitope contained in HCV.

In still another embodiment invention immunoassays are also included. These include an immunoassay for detecting an HCV antigen comprising incubating a sample suspected of containing an HCV antigen with a probe antibody directed against the HCV antigen to be detected under conditions which allow the formation of an antigen-antibody complex; and detecting an antigen-antibody complex containing the probe antibody. An immunoassay for detecting antibodies directed against an HCV antigen comprising incubating a sample suspected of containing anti-HCV antibodies with a probe polypeptide which contains an epitope of the HCV, under conditions which allow the formation of an antibody-antigen complex; and detecting the antibody-antigen complex containing the probe antigen.

In still another embodiment the term polypeptide is used referring to a polymeric form of nucleotide of any length, either ribonucleotides or deoxyribonucleotides. It also includes the known types of modifications, for example, labels which are known in the art, methylation, "caps", substitution of one or more of the naturally occurring nucleotides with an analog, internucleotide modifications, such as, for example, those with unchanged linkages, e.g., methyl phosphates, phosphotriesters, phosphoamidates, carbamates, etc, and with charged linkages. "Purified polypeptide" refers to a composition comprising a specified polypeptide that is substantially free of other components, such composition typically comprising at least about 70% of the specified polypeptide, more typically at least about 80%, 90% or even 95% to 99% of the specified polypeptide.

In still another embodiment the "recombinant host cells", "host cells", "cells", "cell lines", "cell cultures", and other such terms denote microorganisms or higher eukaryotic cell lines cultured as unicellular entities that can be, or have been, used as recipients for a recombinant vector or other transfer DNA, and include the progeny of the original cell which has been transformed. It is understood that the progeny of a single parental cell may not necessarily be completely identical in morphology or in genomic or total DNA complement as the original parent due to natural, accidental, or deliberate mutation.

In still another embodiment the term "replicon" is any genetic element, e.g., a plasmid, a a chromosome, a virus, a cosmid, etc. that behaves as an autonomous unit of polynucleotide replication within a cell, i.e., capable of replication under its own control. A "cloning vector" is a replicon that can transform a selected host cell and in which another polynucleotide segment is attached, so as to bring about the replication and/or expression of the attached segment. Typically, cloning vectors include plasmids, virus, e.g., bacteriophage vector, and cosmids. An "integrating vector" is a vector that does not behave as a replicon in a selected host cell, but has the ability to integrate into a replicon (typically a chromosome) resident in the selected host to stably transform host. An "expression vector" is a construct that can transform a selected host cell a provides for 30 expression of a heterologous coding sequence in the selected host. Expression vectors can be either a cloning vector or an integrating vector.

In still another embodiment the "coding sequence" is a polynucleotide sequence which is transcribed into, RNA and/or translated into apolypeptide when placed under the control of appropriate regulatory sequences. The boundaries of the coding sequence are determined by a translation start codon at the 5' terminus and a translation stop codon 3' terminus. A coding sequence can include, but is not limited to mRNA, cDNA and recombinant polynucleotide sequences. "Control sequence" refers to polynucleotide regulatory sequences which are necessary to affect the expression of coding sequences to which they are ligated. The nature of such control sequences differs depending upon the host organism. In prokaryotes, control sequences generally include promoter, ribosomal binding site and terminators. In eukaryotes generally control sequences include promoters, terminators and, in some instances, enhancers. The term "control sequences" is intended to include, at a minimum, all components the presence of which are necessary for expression and may also include additional advantageous components. "Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In still another embodiment an open reading frame or ORF is a region of a polynucleotide sequence which encodes a polypeptide: this region may represent a portion of a coding sequence or a total coding sequence.

In still another embodiment the term "immunologically cross reactive" refers to two or more epitopes or polypeptides that are bound by the same antibody. Cross-reactivity can be determined by any of a number of immunoassay techniques, such as a competition assay. As used, the term "antibody" refers to a polypeptide or group of polypeptides which comprise at least one epitope. An "antigen binding site" is formed from the folding of the variable domains of an antibody molecule (s) to form three-dimensional binding sites with an internal surface shape and charge distribution complementary to the features of an epitope of an antigen, which allows for specific binding to form an antibody-antigen complex. An antigen binding site may be formed from a heavy -and/or light-chain domain (VH and VL, respectively), which form hypervariable loops which contribute to antigen binding.

In still another embodiment the term "epitope" refers to an antibody binding site usually defined by a polypeptide, but also by non-amino acid haptens. An epitope could comprise 3 amino acids in a spatial conformation which is unique to the epitope, generally an epitope consists of at least 5 such amino acids and more usually consists of at least 8-10 such amino acids. "Antigen-antibody complex" refers to the complex formed by an antibody that is specifically bound to an epitope on an antigen. "Immunogenic polypeptide" refers to a polypeptide that elicits a cellular and/or humoral immune response in a mammal whether alone or linked to a carrier in the presence or absence of an adjuvant. "Polypeptide" refers to a polymer of amino acids and does not refer to a specific length of the molecule. Thus peptides, oligopeptides,and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid including, for example, unnatural amino acids. etc.), polypeptides with substituted linkages, as well as other modifications known in the art both naturally occurring and non-naturally occurring. "Transformation", as used refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid or alternatively, may be integrated into the host genome. A "transformed" host cell refers to both the immediate cell that has undergone transformation and its progeny that maintain the originally exogenous polynucleotide. "Treatment" as used refers to prophylaxis and/or therapy. "Sense strand" refers to the strand of a DNA molecule that is homologous to a mRNA transcript thereof. The "anti-sense strand" contains a sequence which is complementary to that of the "sense strand".

In still another embodiment an "Antibody-containing body component" refers to a component of an individual's body which is a source of the antibodies of interest. Antibody -containing body components are known in the art, limited to, whole blood and components thereof, plasma, serum, spinal fluid, lymph fluid, the external secretions of the respiratory, intestinal, and genitourinary tracts, tears, saliva, milk, white blood cells, and myelomas. "Purified HCV" isolate refers to a preparation of HCV particles which have been isolated from the cellular constituents with which the virus is normally associated, and from other types of viruses which may be present in the infected tissue. The techniques for isolating viruses of skill in the art, and include, for example centrifugation and affinity chromatography.

In still another embodiment an HCV "particle" is an entire virion, as well as particles which are intermediates in virion formation. HCV proteins associated with the HCV proteins associated with the HCV nucleic acid. "Probe" refers to a polynucleotide which forms a hybrid structure with a sequence in a target polynucleotide, due to complementarity of at least one region in the probe with a region in the target. "Biological sample" refers to a sample of tissue or fluid isolated from an individual, including but not limited to, for example, whole blood and components thereof, plasma, serum, spinal fluid, and lymph fluid. The external secretions of the skin and respiratory, intestinal, and genitourinary tracts, tears, saliva, milk, blood cells, tumors, organs and samples of in vitro cell culture constituents (including, but not limited to, conditioned medium resulting from the growth of cells in cell culture medium, putatively virally infected cells, recombinant cells, and cell components). In still another embodiment the present pertains to the isolation and characterization of a newly discovered isolate of HCV Indian isolate (AY651061), its nucleotide sequence, protein sequences and resulting polynucleotides, and antibodies derived. Isolate Indian isolate (AY651061) is novel in its nucleotide and amino acid sequences and is believed to characteristic of HCV isolates from Indonesia.

In still another embodiment the nucleotide sequences derived from Indian isolate (AY651061) are useful as probes to diagnose the presence of virus in samples, and to isolate other naturally occurring variants of the virus. these nucleotide sequences also make available polypeptide sequences of HCV antigens encoded within the Indian isolate (AY651061) genome and permit the production of polypeptides which are useful as standards or reagents in diagnostic tests and/or as components of vaccines. Antibodies, both polyclonal and monoclonal, directed against HCV epitopes contained within these polypeptide sequences are also useful for diagnostic tests, as therapeutic agents, for screening of antiviral agents, and for isolating the NANBH virus. In addition, by utilizing probes derived from the sequences disclosed herein it, is possible to isolate and sequence other portions of the Indian isolate (AY651061) genome, thus giving rise to, additional probes and polypeptides which are useful in the diagnosis and/or treatment, both prophylactic and therapeutic, of NANB Hepatitis.

In still another embodiment the availability of the Indian isolate (AY651061) nucleotide sequences enable the construction of polynucleotide probes and polypeptides useful in diagnosing NANBH due to HCV infection and in screening blood donors as well as donated blood and blood products for infection. The Indian isolate (AY651061) sequences also allow the design and production of HCV specific polypeptides which are useful as diagnostic reagents for the presence of antibodies raised during NANBH. Antibodies to purified polypeptides derived from the Indian isolate (AY651061) sequences may also be used to detect viral antigens in infected individuals and in blood.

The knowledge of the Indian isolate (AY651061) sequences also enables the design and production of polypeptides which may be used as vaccines against HCV and also for the production of antibodies, which in turn may be used for protection against the disease and/or for therapy of HCV infected individuals. Moreover, the disclosed Indian isolate (AY651061) sequences enable further characterization of the HCV genome. Polynucleotide probes derived from these sequences, as well as from the HCV genome may be used to screen cDNA libraries for additional viral cDNA sequences.

The Indian isolate (AY651061) polynucleotide sequences, the polypeptides derived and the antibodies directed against these polypeptides, are useful in the isolation and identification of the BBNANBV agent(s). For example, antibodies directed against HCV epitopes contained in polypeptides derived from the Indian isolate (AY651061) sequences may be used in processes based upon affinity chromatography to isolate the virus. Alternatively, the antibodies may be used to identify viral particles isolated by other techniques. The viral antigens and the genomic material within the isolated viral particles may then be further characterized.

The information obtained from further sequencing of the Indian isolate (AY651061) genome, as well as from further characterization of the Indian isolate (AY651061) antigens and characterization of the genomes enable the design and synthesis of additional probes and polypeptides and antibodies which may be used for diagnosis, for prevention, and for therapy of HCV induced NANB Hepatitis and for screening for infected blood and blood-related products.

In still another embodiment the DNA encoding the desired polypeptide, whether in fused or mature form, and whether or not it contains a signal sequence to permit secretion, may be ligated into expression vectors suitable for any convenient host. Both eukaryotic and prokaryotic host systems are presently used in forming recombinant polypeptides, and a summary of some of the more common control systems and host cells is given below. The polypeptide produced in such host cells is then isolated from lysed cells or from the culture medium and purified to the extent needed for its intended use. Such recombinant or synthetic HCV polypeptides can be used as diagnostics or those which give rise to neutralizing antibodies may be formulated into vaccines. Antibodies raised against these polypeptides can also be used as diagnostics or for passive immunotherapy. In addition, antibodies to these polypeptides are useful for isolating and identifying HCV particles.

In still another embodiment the observed relationship of the putative polyproteins of HCV and the Flaviviruses allows a predictor of the putative domains of the HCV "non-structural" (NS) proteins. The locations of the individual NS proteins in the putative Flavivirus precursor polyprotein are fairly well-known. Moreover, these also coincide with observed gross fluctuations in the hydrophobicity profile of the polyprotein. It is established that NS5 of Flaviviruses encodes the virion polymerase, and that NSI corresponds with a complement fixation antigen which has been shown to be an effective vaccine in animals. Recently, it has been shown that a flavivirus protease function resides in NS3. Due to the observed similarities between HCV and the Flaviviruses, deductions concerning the approximate locations of the corresponding protein domains and functions in the HCV polyprotein are possible. The expression of polypeptides containing these domains in a variety of recombinant host cells including, for example, bacteria, yeast, insect and vertebrate cells, should give rise to important immunological reagents which can be used for diagnosis, detection and vaccines.

In still another embodiment although the non-structural protein region of the putative polyproteins of the HCV isolate described herein and of Flaviviruses appears to be generally similar, there is less similarity between the putative structural regions which are towards the N-terminus. In this region, there is a greater divergence in sequence, and in addition the hydrophobic profile of the two regions show less similarity. This "divergence" begins in the N-terminal region of the putative NS1 domain in HCV and extends to the presumed N-terminus. Nevertheless, it is still possible to predict the approximate locations of the putative nucleocapsid (N-terminal basic domain) and E (generally hydrophobic) domains within the HCV polyprotein.

In still another embodiment from these predictions it may be possible to identify approximate regions of the HCV polyprotein that could correspond with useful immunological reagents. For example, the E and NS1 proteins of Flaviviruses are known to have efficacy as protective vaccines. These regions, as well as some which are shown to be antigenic in the HCV1, for example those within putative NS3, C, and NS5, etc. should also provide diagnostic reagents.

In still another embodiment the immunogenicity of the HCV sequences may also be enhanced by preparing the sequences fused to or assembled with particle-forming proteins. In addition, all of the vectors prepared include epitopes specific to HCV having various degrees of immunogenicity such as, for example, the pre-S peptide. Thus, particles constructed from particle forming protein which includes HCV sequences are immunogenic with respect to HCV and particle-form protein.

In still another embodiment therapeutic vaccine may be prepared from one or more immunogenic polypeptides derived from Indian isolate (AY651061). The observed homology between HCV and Flaviviruses provides information concerning the polypeptides which are likely to be most effective as vaccines as well as the regions of the genome in which they are encoded. The general structure of the Flavivirus genome is discussed in Rice et al. (1986) in THE VIRUSES: THE TOGAVIRIDAE AND FLAVIVIRIDAE (Series eds. Fraenkel-Conrat and Wagner. Vol eds. Schlesinger and Schlesinger. Plenum Press). It is known that major neutralizing epitopes for Flaviviruses reside in the E (envelope) protein. Roehrig (1986) in THE VIRUSES: THE TOGAVIRIDAE AND FLAVIVIRIDAE, (Series eds. Fraenkel-Conrat and Wagner, Vol eds. Schlesinger and Schlesinger, Plenum Press). The corresponding HCV E gene and polypeptide encoding region may be predicted, based upon the homology to Flaviviruses. Thus, vaccines may be comprised of recombinant polypeptides containing epitopes of HCV E. These polypeptides may be expressed in bacteria, yeast, or mammalian cells, or alternatively may be isolated from viral preparations. It is also anticipated that the other structural proteins may also contain epitopes which give rise to protective anti-HCV antibodies. Thus, polypeptides containing the epitopes of E, C, and M may also be used, whether singly or in combination, in HCV vaccines. In still another embodiment it has been shown that immunization with NS1 (non-structural protein 1), results in protection against yellow fever. Schlesinger et al. (1986) J. Virol. 60: 115-123. This is true even though the immunization does not give rise to neutralizing antibodies. Thus, particularly because this protein appears to be highly conserved among Falviviruses, it is likely that HCV NS1 will also be protective against HCV infection. Moreover, it also shows that non-structural proteins may provide protection against viral pathogenicity, even if they do not cause the production of neutralizing antibodies.

In still another embodiment multivalent vaccines against HCV may be comprised of one or more epitopes from one or more structural proteins, and/or one or more epitopes from one or more non structural proteins.

In still another embodiment the vaccines may be comprised of, for example, recombinant HCV polypeptides and/or polypeptides isolated from the virions. In particular, vaccines are contemplated comprising one or more of the following HCV proteins, or subunit antigens derived therefrom: E, NS1, C, NS2, NS3, NS4 and NS5. Particularly preferred are vaccines comprising E and/or NS1, or subunits thereof. In addition, it may be possible to use inactivated HCV in vaccines: inactivation may be by the preparation of viral lysates, or by other means known in the art to cause inactivation of Flaviviruses, for example, treatment with organic solvents or detergents, or treatment with formalin. Moreover, vaccines may also be prepared from attenuated HCV strains or from hybrid viruses such as vaccinia vectors known in the art [Brown et al. Nature 319: 549-550].

In still another embodiment the proteins may be formulated into the vaccine as neutral or salt forms. Pharmaceutically acceptable salts include the acid addition salts (formed with free amino groups of the peptide) and which are formed with inorganic acids such as for example hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Generally, it is expected that the HCV genome sequence will be present in serum of infected individuals at relatively low levels i.e., at approximately $10^2$-$10^3$ chimp infectious doses (CID) per ml. This level may require that amplification techniques be used in hybridization assays.

In still another embodiment the Flavivirus model for HCV allows predictions regarding the likely location of diagnostic epitopes for the virion structural proteins. Similarly, domains of the non-structural proteins are expected to contain important diagnostic epitopes, e.g., NS5 encoding a putative polymerase and NS1 encoding a putative complement-binding antigen. Recombinant polypeptides, or viral polypeptides, which include epitopes from these specific domains may be useful for the detection of viral antibodies in infectious blood donors and infected patients. Moreover, these antibodies may be extremely useful in detecting acute-phase donors and patients.

In still another embodiment the antigenic regions of the putative polyprotein can be mapped and identified by screening the antigenicity of bacterial expression products of HCV cDNAs which encode portions of the polyprotein. Other antigenic regions of HCV may be detected by expressing the portions of the HCV cDNAS in other expression systems, including yeast systems and cellular systems derived from insects and vertebrates. In addition, studies giving rise to an antigenicity index and hydrophobicity/hydrophilicity profile give rise to information concerning the probability of a region's antigenicity. Efficient detection systems may include the use of panels of epitopes. The epitopes in the panel may be constructed into one or multiple polypeptides.

In still another embodiment kits suitable for immunodiagnosis and containing the appropriate labeled reagents are constructed by packaging the appropriate materials, including the polypeptides of the invention containing HCV epitopes or antibodies directed against HCV epitopes in suitable containers along with the remaining reagents materials required for the conduct of the assay (e.g., wash buffers, detection means like labeled anti human Ig, labeled anti-HCV, or labeled HCV antigen), as well as a suitable set of assay instructions.

The Indian isolate (AY651061) nucleotide sequence information described herein may be used to gain information about the sequence of the HCV genomes, and for identifying and isolating additional HCV isolates related to this isolate. This information, in turn, can lead to additional polynucleotide probes, polypeptides derived from the HCV genome, and antibodies directed against HCV epitopes which would be useful for the diagnosis and/or treatment of HCV caused NANB Hepatitis.

The current standard-of-care therapy for chronically infected HCV patients is a combination of pegylated IFN and ribavirin, which is costly, lengthy (6-12 months), associated with significant side effects and results in sustained viral respones in only 50% of patients. In patients infected with genotype 1, the most common form, response rates are even lower. With an estimated 170 million HCV carriers worldwide, it is clearly important to develop better therapeutic options. With our increasing knowledge of the virus encoded enzymes and genetic elements vital to the life-cycle of HCV, much attention is now being focused on the development of HCV protease, replicase, helicase, antisense, silencing RNA and other specific inhibitors. However, preliminary data have directly linked responses to IFN-a and ribavirin with pretreatment titers of viral antibodies (presumed to be against the envelope glycoproteins), peripheral $T_H$ cell responses to the HCY core and other antigens, as well as to intrahepatic CDS+ CTL responses to the virus. Total pretreatment CDS+ T-cell counts in the liver have also been correlated with sustained responses to standard-of-care therapy. Therefore, it may be possible to boost such immune responses in patients by appropriate vaccination and thereby improve the response rate to the standard-of-care therapy. Such immunotherapy may also help control the emergence of escape mutants that would be predicted to arise from any future use of HCV protease or replicase inhibitors, for example, given the extreme fluidity and heterogeneity of the HCV genome.

In still another embodiment provides many therapeutic vaccine trials are planned or are already in progress and use diverse delivery methods and formulations but little information is available about their efficacy at present. What is known, however, is that use of an alum-adjuvanted recombinant gpEl antigen was able to boost humoral and cellular immune responses to gpEl in viraemic patients, providing encouragement that vaccination can increase immune responses in pre-existing carriers. It remains to be seen whether boosting viral-neutralizing antibody titres or broad CD4+ $T_H$ responses or broad CDS"I-cell responses will have the greatest impact on reducing viral load and in the response to antiviral therapy. But, as may be the case for optimal prophylaxis, boosting of these immune responses may be ideal for immunotherapy.

In still another embodiment the general techniques used in extracting the genome from a virus preparing and probing a cDNA library, sequencing clones. constructing expression vectors, transforming cells, performing immunological assays such as radioimmunoassays and ELISA assays, for growing cells in culture, and the like are known in the art and laboratory manuals are available describing these techniques. However, as a general guide the following sets forth some sources currently available for such procedures. and for materials useful in carrying them out.

In still another embodiment both prokaryotic and eukaryotic host cells may be used for expression of desired coding sequences when appropriate control sequences which are compatible with the designated host are used. Among prokaryotic hosts, *E. coli* is most frequently used. Transfer vectors compatible with prokaryotic hosts are commonly derived from, for example, pBA322, a plasmid containing operons conferring ampicillin and tetracycline resistance, and the various pUC vectors. which also contain sequences conferring antibiotic resistance markers. These markers may be used to obtain successful transform ants by selection. The foregoing systems are particularly compatible with *E. coli*; if desired, other prokaryotic hosts such as strains of *Bacillus* or *Pseudomonas* may be used, with corresponding control sequences.

In still another embodiment, a vector construction employs techniques which are known in the art. Site-specific DNA cleavage is performed by enzymes under conditions which generally are specified by the manufacturer of these commercially available enzymes. The cleaved fragments may be separated using polyacrylamide or agarose gel electrophoresis techniques, according to the general procedures found in Methods in Enzymology (1980) 65 :499-560. Sticky ended cleavage fragments may be blunt ended using *E. coli* DNA polymerase I (Klenowfln) in the presence of the appropriate deoxynucleotide triphosphates (dNTPS) present in the mixture. Treatment with S1 nuclease may also be used, resulting in the hydrolysis of any single stranded DNA portions.

In still another embodiment, ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and religation of the vector; alternatively, restriction enzyme digestion of unwanted fragments can be used to prevent ligation. Ligation mixtures are transformed into suitable cloning posts. such as *E. coli*, and successful transform ants selected by, for example, antibiotic resistance, and screened for the correct construction.

In still another embodiment the present invention describes the cloning of the Indian isolate (AY651061) nucleotide sequences. Blood sample was used as a source of HCV virions was found to be positive in an anti HCV antibody assay. The HCV isolate from these samples were named Indian isolate (AY651061). The infectivity of the blood sample containing the Indian isolate (AY651061) isolate was confirmed by a prospective study of blood transfusion recipients. Dr. C. M. Habibullah from the Department of Gastroenterology at Owaisi Hospital, Hyderabad, India collected blood from patients who have contracted post-transfusion non-A, non-B hepatitis. He also collected blood samples from the respective blood donors of these patients. Next, these samples were assayed for antibodies to the 3$^{rd}$ EIA and blood from one of the donors was found to be positive.

In still another embodiment, isolation of the RNA from the blood samples began by pelleting virions in the blood sample by ultracentrifugation [Bradley, O W, McCaustland, K. A., Cook E. H. Schable. C A, Ebert. JW. and Maynard, J. E. (1985) Gastroenterology 88, 773-779]. RNA was then extracted from the pellet by the guanidinium/cesium chloride method [Maniatis T., Fritsch, E. F., and Sambrook J. (1982) "Molecular Cloning: A Laboratory Manual", Cold Spring Harbor Laboratory. Cold Spring Harbor] and further purified by 35 phenol/chloroform extraction in the presence of urea, [Berk. A. J. Lee. F. Harrison, T. Williams, J. and Sharp, P. A. (1979) Cell 17, 935 944]. Eleven pairs of Synthetic oligonucleotide primers were designed from the 5'UTR, C, E1. E2, P7, NS2, NS3, and N55 domains of the nucleotide sequence of Indian isolate (AY651061) to isolate fragments from AY051292 and HCV -1 genome. The first set of primers was to isolate the sequence from the 5' UTR and a bit of core, the second set was core, third set envelope domain, fourth set envelope domain, fifth set of primers were to isolate a fragment which overlapped the putative envelope and non-structural one, NS1 domains, sixth set was NS2 domain, seventh set of primers was NS3, eighth set of primers was NS4, ninth set of primers was NS5A, tenth set of primers was a part of NS5B, eleventh set of primers was a part of NS5B and 3'UTR. The sequences for the various primers are shown in FIG. 27.

In still another embodiment about 1 µg of the anti-sense primers, was added to 10 units of reverse transcriptase (Promega) to synthesize cDNA fragments from the isolated RNA as the template. The cDNA fragments were then amplified by a standard polymerase chain reaction [Saiki, R. K., Scharf, S., Faloona, F., Mullis, K. B., Horn G. T., Erlich, H. A., and Arnheim, N. (1985) Science 230, 1350-1354]-after 1 µg of the appropriate sense primers was added. The cDNA fragments amplified by the PCR method were gel isolated and cloned pGMT EASSY vector. Clones which contain the fragments of the viral domains were successfully constructed. From the PCR reaction of the Indian isolate (AY651061), three independent clones from each region, C/E, E, E1NS1, NS3, and NS5, have been sequenced by the dideoxy chain termination method. Sequence from all regions has been isolated from the Indian isolate (AY651061). However, there is heterogeneity between clones containing sequence from the same region. Consequently, a consensus sequence was constructed for each of the domains. These differences may be explained as artifacts which occur randomly during the PCR amplification [Saiki, R. K., Scharf, S., Faloona, F., Mullis, K. B., Horn, G. T., Erlich, H A, and Arnheim, N. (1985) Science 230, 1350-1354]. Another explanation is that more than one virus genome is present in the plasma of a single healthy carrier and that these genomes are heterogeneous at the nucleotide level.

In still another embodiment, it was determined how many of these nucleotide differences would lead to amino acid changes, using the sequence from the NS3 domain of the HCV 1 isolate as an example. Out of the five nucleotide differences, three fall on the third position' of the amino acid codon and do not change the amino acid sequence. Both of the remaining two nucleotide changes fall on the first position of the amino acid codon and generate amino acid changes of threonine to alanine and proline to alanine all of which are small, neutral amino acid residues. Similarly, when analyzing the nucleotide differences in other domains, many silent and conserved mutations are found. These results suggest that nucleotide sequences of the HCV genomes in the plasma of a single healthy donor are heterogeneous at the nucleotide level. In addition, once the consensus sequences for each of the fragments were compiled each sequence was compared to the HCV 1 isolate in FIGS. 11 through 19. The invention is further elaborated with the help of following example(s). However, these example(s) should not be construed to limit the scope of the invention.

EXAMPLE 1

Selection and HCV RNA Isolation from HCV Infected Patient:

A single chronic Hepatitis C virus infected patient was selected for sequence and characterization of complete genome of hepatitis C virus. Twenty ml of intravenous blood was collected and serum was separated and stored at −70° C.

HCV RNA isolation: HCV RNA was isolated from the serum by the guanidinium isothicynate (GITC) acid-phenol method (Chomeczynski and Saachi 1987). 2001 µl of serum was mixed with 500 µl lysis buffer (4M GITC, 0.75 M Sodium acetate, 0.5% Sarkosyl, 0.1M β-meracapto ethanol), 50 µl of 3M sodium acetate (Ph 5.2), 500 µl water saturated phenol and 200 µl cholorofrom: Iso amyl alcohol (24:1v/v).

The tubes were vortexed in each step and finally kept in ice for 15 min. The tubes were centrifuged at 12000 rpm for 30 min in refrigerated centrifuge.

The aqueous phase (approx. 500 µl) was collected very carefully, mixed with equal volume of isopropanol and kept at −70° C. over night.

The over night kept solutions were centrifuged at 12000 rpm for 30 min at 4° C. and pellets were washed with 1 ml of 70% ethanol. The tubes were dried in heat block at 55° C. for 10 min and each pellet was re-suspended in 20 µl DEPC treated water.

Many sets of primers were designed to construct cDNA followed by PCR. (The list of primers is attached (SEQ ID NOS: 19-40)).

EXAMPLE 2 cDNA Synthesis cDNA synthesis was carried out by adding 6 µl of the isolated HCV RNA to a final 20 µl of reaction mix composed of 40 picomoles of reverse primer, 4 µl of 5× reverse transcriptase buffer, 1 µl of 10 mM dNTPs, 7 µl of DEPC-treated water, 100 U of reverse transcriptase (MMLV supplied by promega). The mixture was incubated at 42° C. for 60 min. The reaction was terminated by heating at 70° C. for 15 min, and then chilled the mixture on ice.

Polymerase Chain Reaction

For amplification by PCR, a 50 µl mixture containing 10 µl of the c DNA, 1X PCR buffer, 1 µl 10 mM dNTPs, 1.5 µl MgC12, 2 U Taq polymerase and 1 µl of each forward and reverse was denatured at 95° C. for 3 minutes and amplified for 36 cycles under the following conditions: 94° C. for 1 minutes (denaturation), 54° C. for 1.5 minutes (annealing), and 72° C. for 2 minutes (extension), followed by a final extension at 72° C. for 5 minutes. PCR products were analyzed on 2% agarose gels followed by staining with ethidium bromide and visualized under a UV illuminator. A 100 bp ladder (Promega, Madison, Wis.) was used as a size marker.

EXAMPLE 3

Cloning of the PCR Product

The purified PCR product was ligated with pGEM-T easy vector. The ligation mix included 2× rapid ligation buffer, T4 DNA ligase (3 Weiss units/µl), PCR product and the final reaction volume made upto 10 µl with deionized water. The reaction mixture was incubated at 16° C. overnight.

Competent cells were prepared by picking a single bacterial colony from a plate that has been incubated for 16-20 hours at 37° C. Transfer the colony into 100 ml of LB broth in a 1 liter flask. Incubate the culture for 3hours at 37° C. with vigorous agitation, monitoring the growth of the culture. As a guideline, 1 $OD_{600}$ of a culture of E. coli strain TOP 10 F contains ~$10^9$ bacteria/ml. Transfer the bacterial cells to sterile, disposable, ice-cold 50 ml polypropylene tubes. Cool the cultures to 0° C. by storing the tube on ice for 10 minutes. Recover the cells by centrifugation at 5000 rpm for 10 minutes at 4° C. Decant the medium from the cell pellets. Stand the tubes in an inverted position on a pad of paper towels for 1 minute to allow the last traces of media to drain away. Resuspend each pellet by swirling or gentle vortexing in 30 ml of ice-cold $CaCl_2$ ($CaCl_2$ $2H_2O$ (1M)) solution and kept on ice for one hour. Recover the cells by centrifugation at 5000 rpm for 10 minutes at 4° C. Decant the medium from the cell pellets. Stand the tubes in an inverted position on a pad of paper towels for 1 minute to allow the last traces of media to drain away. Resuspend the pellet by swirling or gentle vortexing in 2 ml of ice-cold 0.1 M $CaCl_2$ for each 50 ml of original culture. At this point, either use the cells directly for transformation or dispense into aliquots contain each 200 µl and freeze at –70° C. To transform the $CaCl_2$— treated cells, thaw cells on for 15 minutes. Add DNA (no more than 50 ng in a volume of 10 µl or less) to each tube. Mix the contents of the tube by swirling gently. Store the tubes on ice for 30 minutes. Transfer the tubes to a rack placed in a preheated 42° C. circulating water bath. Store the tubes in the rack for exactly 90 seconds. Do not shake the tube. Rapidly transfer the tubes to an ice bath. Allow the cells to chill for 1-2 minutes. Add 800 µl LB medium to each tube. Incubate the cultures for 45 minutes in a water bath set at 37° C. to allow the bacteria to recover and to express the antibiotic resistance markers encoded by the plasmid. Recover the cells by centrifugation at 5000 rpm for 5 minutes, resuspend each pellet by swirling or gentle vortexing in 100 µl of LB medium, IM IPTG and X-gal for blue white screening. Transfer the appropriate volume of transformed competent cells on LB agar medium containing the appropriate antibiotic. Store the plates at room temperature until the liquid has been absorbed. Invert the plates and incubate at 37° C. Transformed colonies should appear in 12-16 hours. Remove the plates from the incubator and store them for several hours at 4° C. to develop. Identify colonies carrying recombinant plasmids, colonies that carry wild—type plasmids contain active β-Galactosidase. These colonies are pale blue in the center and dense blue at their periphery. Colonies that carry recombinant plasmids do not contain active β-Galactosidase. These colonies are creamy white or eggshell blue, sometimes with a faint blue spot in the center. Select and culture colonies carrying recombinant plasmids.

Plasmid DNA was prepared by Alkaline Lysis method. Inoculate 5 ml of LB medium containing the appropriate antibiotic with a single colony of transformed bacteria. Incubate the culture overnight at 37° C. with vigorous shaking. Pour 1.5 ml of the culture into a microfuge tube. Centrifuge at maximum speed for 30 seconds at 4° C. in a microfuge. Store the unused portion of the original culture at 4° C. When centrifugation is complete, remove the medium by aspiration, leaving the bacterial pellet as dry as possible. Resuspend the bacterial pellet in 100 µl of ice-cold Alkaline Lysis solution I (50_mM glucose, 25_mM Tris-Cl (pH 8.0), 10_mM EDTA (pH 8.0)) by vigorous vortexing. Add 200 µl of freshly prepared Alkaline Lysis Solution II (0.2N NaOH, 1% (w/v) SDS) to each bacterial suspension. Close the tube tightly, and mix the contents by inverting the tube rapidly five times. Do not vortex! Store the tube on ice. Add 150 µl of ice-cold Alkaline Lysis Solution III. Close the tube and disperse Alkaline Lysis Solution III (5M potassium acetate, glacial acetic acid) through the viscous bacterial lysate by inverting the tube several times. Store the tube on ice for 3-5 minutes. Centrifuge the bacterial lysate at maximum speed for 5 minutes at 4° C. in a microfuge. Transfer the supernatant to a fresh tube. Add an equal volume of phenol: chloroform. Mix organic and aqueous phases by vortexing and then centrifuge the emulsion at maximum speed for 2 minutes at 4° C. in a microfuge. Transfer the aqueous upper layer to a fresh tube. Precipitate nucleic acids from the supernatant by adding 2 volumes of ethanol at room temperature, Mix the solution by vorterxing and then allow the mixture to stand for 2 minutes at room temperature. Collect the precipitated nucleic acids by centrifugation at maximum speed for 5 minutes at 4° C. in a microfuge. Remove the supernatant by gently stand the tube in an inverted position on a paper towel to allow all of the fluid to drain away. Add 1 ml of 70% ethanol to the pellet and invert the closed tube several times. Recover the DNA by centrifugation at maximum speed for 2 minutes at 4° C. in a microfuge. Again remove all of the supernatant by gently and store the open tube at room temperature until the ethanol has evaporated and no fluid is visible in the tube (5-10 minutes). Dissolve the nucleic acids in 50 µl of TE (pH 8.0). Vortex the solution gently for a few seconds. Store the DNA solution at 20° C. All the clones were digested with EcoRI to excise the fragment and were checked for confirmation analysis. The gel picture shows us the results of the clones of all AY651061.

Detection of Antibody to HCV has become the principal method for the diagnosis of HCV infection in individuals with chronic hepatitis and for the screening of blood donors. The original assay based upon the recombinant proteins derived from NS4 showed non-specificity and insensitivity, the more recently developed assays that use recombinant proteins from the core and NS3 regions of the HCV genome (second generation) and the NS5 region of the HCV genome (third generation) have proved to be more effective.

HCV can be classified into at least into six major genotypes, whose nucleotide and inferred amino acid sequences over the whole genome differ by approximately 30%. Significant antigenic differences have been documented and form the basis of thir classification into serotypes. We wanted to measure serological reactivities to the individual component antigens core, NS3, NS4 and NS5. ORF of Hepatitis C virus whole genome (9441 base pairs) is shown in FIG. 1.

The entire genome of Hepatitis C virus genotype predominant in India was cloned, sequenced and submitted to GenBank (Accession Number AY651061). DNA fragments of all the four antigens viz., Core, NS3, NS4 and NS5 used in the 3$^{rd}$ generation diagnostic kits were cloned into pET21 vecors and expressed in E. coli BL21(DE3) strain.

EXAMPLE 4

Core

Cloning and Characterization: The sequencing encoding the core protein is highly conserved among all the Hepatitis C viral subtypes and is localized to nucleotides 342 to 915. The corresponding protein has 191 amino acids and with a molecular weight of about 22 kDa. The coding sequence of core was amplified by Polymerase Chain Reaction (PCR) using gene specific primers. The forward primer contains a BamHl site and the reverse primer contains an EcoRI site. The amplified 567 bp DNA fragment was then inserted between the BamHI and EcoRI sites of the expression vector pET21 (FIG. 2a). This DNA was transferred in to E.coli BL21(DE3) cells and individual clones expressing high levels of core were selected. The core sequence was confirmed by sequencing.

Protein purification: E.coli cells expressing core were induced by isopropyl-thiogalactoside (IPTG) and pelleted by centrifugation. The pellet was resuspended in lysis buffer and the inclusion bodies were isolated as described (Sambrook et al., 2001). Following solubilization of inclusion bodies with detergents, the protein was purified to homogeneity either by preparative electro-elution or ion exchange chromatography. Purity of the protein was assessed by SDS-polyacrylamide gel electrophoresis (PAGE) (FIG. 3) SDS PAGE gel for the core protein, and a western blot picture of Core protein is shown in FIG. 4.

EXAMPLE 5

NS3

Cloning and Characterization: The DNA fragment encoding the 271 amino acid NS3 (amino acids from 1192 to 1463) was amplified by PCR and cloned in to pET21b at the SalI site under the T7 promoter (FIG. 2b). The clone was verified by DNA sequencing and then introduced into expression host E. coli BL21 (DE3).

Protein Purification: The bacterial clone carrying NS3 gene was induced by IPTG, collected cells by centrifugation and inclusion bodies were prepared as described for Core. Following solubilization of inclusion bodies the protein was purified to homogeneity either by preparative gel electro-elution or ion exchange chromatography. Purity of NS3 protein was checked by SDS-PAGE (FIG. 5).

EXAMPLE 6

NS4

Cloning and Characterization: The DNA sequence encoding the NS4 region (nucleotides 5246 to 6015;) SEQ ID NO: 1 was amplified by PCR using the gene specific forward and reverse primers. Thus amplified 765 bp DNA is digested with BamHI and NotI at 5' and 3' ends respectively and inserted into the BamHI and NotI sites in pET21 a (+) vector (FIG. 2c) and transferred into E.coli BL21 (DE3) cells. the clone expressing highest levels of NS4 was selected and the DNA was sequenced. It should be pointed out that in this clone about of 83 amino acids at the COOH-end was missing. Subsequently we cloned this additional sequence also to give to produce full-length protein (~305 amino acids (SEQ ID NO: 16)). It should be pointed out that both truncated and the full-length proteins are equally efficient in detecting positive patients'sera.

Protein purification: Standard purification protocol described above for Core and NS3 was used to purify NS4 to homogeneity which was verified by SDS-PAGE (FIG. 6)

EXAMPLE 7

NS5: Cloning and Characterization

The NS5A region extends from nucleotides 6281 to 7403 (SEQ ID NO: 1 (374 amino acids; SEQ ID NO: 2) and mass of about 45 kDa. The region was amplified by PCR using the gene specific primers containing NdeI and BamHI sites in the forward and reverse primers, respectively. The amplified 1100 bp DNA was digested with NdeI and BamHI and inserted at the NdeI and BamHI sites of pET21a (+) vector (FIG. 2d), which was then transferred into E. coli BL21 (DE3) cells. The bacterial clone carrying the NS5 gene was confirmed by DNA sequencing.

Protein purification: Induction, isolation of inclusion bodies and solubilization were as described for Core and NS3. Purity was checked by SDS-PAGE (FIG. 7) SDS PAGE gel for the NS5 protein, Western blot analysis showing the presence of the NS5 protein is shown in FIG. 8.

Results

A total number of 532 patients were screened for HCV infection. A total of 218 patients were found to be positive by RT-PCR. Among the 218 samples, 211 were positive by 3$^{rd}$ EIA where as all the 218 were positive by the Core, NS3, NS4, NS5 proteins derived from our Indian isolate (AY651061). Further competitive analysis for each antigen showed the following results:

About 98 samples were positive by all the four proteins and 38 samples were reactive with core, NS3, NS4, but were not picked by NS5. Similarly, 29 samples were not detected by NS4 and NS5 and 12 samples were not detected by core protein EIA. 10 samples were not picked by NS5 and Core, 16 samples were not picked by NS4, 8 samples were not picked by NS4 and core.

The interesting observation of the present analysis was that 7 samples were not picked by 3$^{rd}$ EIA but were picked by our purified proteins. A total of 4 samples were picked by core and NS3, 2 samples were picked by core, NS3 and NS4, and 1 sample was picked by core. About 315 samples were negative by all the methods that were used.

| Core | NS3 | NS4 | NS5 | Total No. Samples | RT-PCR | Abbott 3rd EIA |
|------|-----|-----|-----|-------------------|--------|----------------|
| +    | +   | +   | +   | 98                | +      | +              |
| +    | +   | +   | −   | 38                | +      | +              |
| +    | +   | −   | −   | 29                | +      | +              |
| −    | +   | +   | +   | 12                | +      | +              |
| −    | +   | +   | −   | 10                | +      | +              |
| +    | +   | −   | +   | 16                | +      | +              |
| −    | +   | −   | +   | 08                | +      | +              |
| +    | +   | −   | −   | 04                | +      | −              |
| +    | +   | +   | −   | 02                | +      | −              |
| +    | −   | −   | −   | 01                | +      | −              |
| −    | −   | −   | −   | 314               | −      | −              |
|      |     |     |     | 532               |        |                |

The findings of significant antigenic variability of antigens used for serological screening will form the basis for a number of future investigations. It will be possible to carryout screening of our population infected with genotype 1. This may reveal the frequency with which anti-HCV samples are being missed therefore, assays developed from purified proteins from our isolate may be more effective for the detection of antibody elicited by infection with a specific genotype that is more prevalent.

Our recent progress on HCV gave us a lot of new information on the genetic variation of the strains floating in Indian population. This will provide the basis for developing an effective vaccine.

EXAMPLE 8

Transformation

About 10 µl of ligation mixture was added to the competent E.coli; Top10F' cells and incubated on ice for 20 minutes. Following a 90 sec incubation at 42° C., 1000 µl of LB medium was added to the tube and incubated for 45 min at 37° C. Cells were centrifuged at 5000 rpm for 5 min, dissolved the pellet in 100 µl LB medium and plated on a LB plate with appropriate antibiotic and IPTG/X-gal. Plates were incubated overnight at 37° C. Colonies and selected and grown in a 5 ml LB broth overnight at 37° C. with shaking. DNA was isolated from a 1.5 ml culture in 1.5 ml Eppendoff using Quiagen plasmid DNA kit. After plasmid DNA isolation, DNA was digested with EcoRI enzyme to check the insert and the DNA was sent for sequencing.

EXAMPLE 9

DNA Sequencing

The cloned HCV sequences were amplified using M13 primers both forward and reverse. The re-amplified PCR products were sequenced by the direct sequencing method in an automated sequencer (Applied Biosystems, Inc., Foster City, CA, USA). Sequences of all clones of HCV genome were analyzed and checked with NCBI Blast software program. All the sequences from different clones of HCV genome were joined using CHROMAS chromas and CHROMAS-PRO software programs. This complete Indian isolate of the HCV genome was submitted to Genbank.

EXAMPLE 10

Comparative Analysis of New Isolate (Indian Strain: AY 651061) with the Prototype HCV1

The HCV genome organized into several regions which code for various viral proteins-5' untranslated region (UTR), core gene, genes for two enyelope glycoproteins (E1 & E2/NS1) genes for seven nonstructural proteins (NS2, NS3A,NS3B, NS4A, NS4B, NS5A & NS5B) and 3'UTR. The nucleotide comparison of various viral proteins shown in FIG. 11 to FIG. 19, and amino acid comparison with various viral proteins are shown in FIG. 20 to FIG. 26.

The complete genome of new Indian isolate shows 82.9% nucleotide homology with prototype HCV1 strain.

The 5'UTR is highly conserved among all the strains, 99.1% nucleotide homology was observed in new Indian isolate compared HCV1.

The new Indian isolate of HCV Core gene was showing 97.6% nucleotide homology compared with prototype HCV1.

The new Indian isolate of HCV E1 gene was showing 80.8% nucleotide homology compared with prototype HCV1.

The new Indian isolate of HCV E2/NS1 gene was showing 84.7% nucleotide homology compared with prototype HCV1.

The new Indian isolate of HCV NS2 gene was showing 81.9% nucleotide homology compared with prototype HCV1.

The new Indian isolate of HCV NS3 gene was showing 82.4% nucleotide homology compared with prototype HCV1.

The new Indian isolate of HCV NS4 gene was showing 79.3% nucleotide homology compared with prototype HCV1.

The new Indian isolate of HCV NS5 gene was showing 80% nucleotide homology compared with prototype HCV1.

The new Indian isolate of HCV 3'UTR gene was showing 81.5% nucleotide homology compared with prototype HCV.

The complete genome of new Indian isolate shows 86.3% amino acid homology with prototype HCV1 strain.

The new Indian isolate of HCV Core gene was showing 98.4% amino acid homology compared with prototype HCVI.

The new Indian isolate of HCV E1 gene was showing 80.5% amino acid homology compared with prototype HCV1.

The new Indian isolate of HCV E2/NS1 gene was showing 86.2% amino acid homology compared with prototype HCV1.

The new Indian isolate of HCV NS2 gene was showing 80.7% amino acid homology compared with prototype HCV1.

The new Indian isolate of HCV NS3 gene was showing 91.4% amino acid homology compared with prototype HCV1.

The new Indian isolate of HCV NS4 gene was showing 87% amino acid homology compared with prototype HCV1.

The new Indian isolate of HCV NS5 gene was showing 83.1% amino acid homology compared with prototype HCV1.

What we claimed:

1. An isolated hepatitis C virus polypeptide sequence comprising SEQ ID NO:2.

2. An isolated polypeptide sequence comprising SEQ ID NO:6, SEQ ID NO:8, SEQ ID NO:10, SEQ ID NO:12, SEQ ID NO:14, SEQ ID NO:16, or SEQ ID NO:18 corresponding to Core protein, Envelope glycoprotein (E1), Envelop glycoprotein (E2)/Non-structural protein NSI, Non-structural protein NS2, Non-structural protein N53, Non-structural protein N54, and Non-structural protein N55 respectively.

3. A composition for inducing an immune response against hepatitis C virus comprising at least one protein as claimed in claim 2 optionally along with pharmaceutically acceptable adjuvants.

4. The composition as claimed in claim 3, wherein the subject is a mammal including humans.

5. The composition as claimed in claim 3, wherein said adjuvants are selected from the group consisting of: mineral salts, oil emulsions and surfactant based formulations, particulate adjuvants, microbial derivatives, endogenous human immunomodulators and inert vehicles.

6. A kit for identifying hepatitis C virus comprising at least one antigenic peptide selected from the peptides in claim 2 capable of reacting specifically with antibodies directed against said virus.

7. The kit as claimed in claim 6, wherein said kit further comprises control standards and instructions for use of the kit.

8. A method for detecting the presence of hepatitis C virus comprising contacting sera with at least one antigenic polypeptide of claim 2, wherein formation of an immunogenic complex confirms detection of said virus.

9. A method of immunization against hepatitis C virus in a subject in need thereof, wherein said method comprises administering a pharmaceutically effective immunizing dose of the composition as claimed in claim 3.

* * * * *

SEQUENCE LISTING

<160> NUMBER OF SEQ ID NOS: 56

<210> SEQ ID NO 1
<211> LENGTH: 9441
<212> TYPE: DNA
<213> ORGANISM: Hepatitis C virus

<400> SEQUENCE: 1

| | | | | | |
|---|---|---|---|---|---|
| gccagccccc | tgatggggc | gacactccgc | catgaatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gataaaccg | ctcaacgcct | ggagatttgg | gcgtgccccc | 240 |
| gcaagactgc | tagccgagta | gtgttgggtc | gcgaaaggcc | ttgtggtact | gcctgatagg | 300 |
| gtgcttgcga | gtgccccggg | aggtctcgta | gaccgtgcac | catgagcacg | aatcctaaac | 360 |
| ctcaaagaaa | aaccaaacgt | aacaccaacc | gtcgcccaca | ggacgtcaag | ttcccgggtg | 420 |
| gcggacagat | cgttggtgga | gtttacttgt | tgccgcgcag | gggccctaga | ttgggtgtgc | 480 |
| gcgcgacgag | gaagacttcc | gagcggtcgc | aacctcgagg | tagacgtcag | cctatccca | 540 |
| aggcacgtcg | gcccgaggc | aggacctggg | ctcagcccgg | gtaccttgg | ccctctatg | 600 |
| gcaatgaggg | ctgcgggtgg | gcgggatggc | tcctgtctcc | ccgcggctct | cggcctagtt | 660 |
| ggggccccac | agacccccgg | cgtagatcgc | gcaatttggg | taaggtcatc | gatacctta | 720 |
| cgtatggctt | cgccgaccct | atggggtaca | taccgctcgt | cggcgccccc | cttggggcg | 780 |
| ctgccagggc | cctggcgcac | ggcgtccggg | tcctggaaga | cggcgtgaac | tatgcaacag | 840 |
| ggaaccttcc | tggttgctct | ttctctatct | tccttctggc | cctgctctct | tgcttgactg | 900 |
| tgcccgcttc | ggccgtcgga | gtgcgcaact | cttcggggt | gtaccatgtc | accaatgatt | 960 |
| gccccaatgc | gtctgttgtg | tacgagacag | atagcttgat | catacatctg | ccggggtgtg | 1020 |
| tgccctgcgt | acgcgagggc | aacgttcga | ggtgctgggt | ctcccttagt | cctactgttg | 1080 |
| ccgctaagga | tccgggcgtc | ccggtcaacg | agattcggcg | tcacgtcgac | ctgattgccg | 1140 |
| gggccgctgc | attctgttcg | gctatgtatg | tagggcactt | atgcggttcc | atcttcctcg | 1200 |
| ttggccagct | tttcacctc | tcccctaggc | gccactggac | aacacaagac | tgtaattgct | 1260 |
| ccatctaccc | aggacatgtg | acaggccatc | gaatggcttg | ggacatgatg | atgaactggt | 1320 |
| cccctacgac | ggcgctggta | gtagcccagc | tgctccggat | cccacaagcc | atcttggaca | 1380 |
| tgatcgctgg | tgctcactgg | ggagtcctgg | cgggcatagc | gtatttctcc | atggtgggga | 1440 |
| actggacgaa | ggtcctggta | gtgctgctgc | tatttgccgg | cgtcgacgcg | acgaccatcg | 1500 |
| tctccgggg | aagtgccggc | cgcagcacgg | ctggacttgt | gggctcttc | tcaccaggcg | 1560 |
| cccgcagaa | catccagctg | atcaacacca | acggcagttg | gcacatcaac | cgcacggccc | 1620 |
| tgaactgcaa | tgatacccet | caaaccggct | gggtagcagg | cttttctat | accaacaaat | 1680 |
| tcaactcttc | gggttgcccc | gagaggttgg | ccagctgccg | acccttgcc | gactttgacc | 1740 |
| agggctgggg | ccctatcagt | tataccaacg | gaagcggccc | cgaccaacgc | cctactgct | 1800 |
| ggcactaccc | cccaaaacct | tgtggtattg | tgccgcagat | gagcgtgtgt | ggcccagtat | 1860 |
| actgcttcac | tcccagcccc | gtggtggtgg | gaacgaccga | caggtcgggc | gcgcccacct | 1920 |
| acaactgggt | tgaaaatgaa | acggacgttt | tcgtcctcaa | caacaccagg | ccacggctgg | 1980 |
| gcaattggtt | cggtggtacc | tggatgaact | caactggatt | caccaaggtg | tgcggagcgc | 2040 |

-continued

| | |
|---|---|
| cccccttgtgc catcggaggg gtgggcaaca acaccttgta ctgcccccact gattgtttcc | 2100 |
| gcaaacatcc ggaagccacg tactctcggt gcggctccgg tccttggatt acacccaggt | 2160 |
| gcttgatcca ctaccgtat aggctttggc attatccttg taccatcaat tacaccatat | 2220 |
| tcaagatcag gatgtttgtg ggcggggttg agcacaggct cgacgccgcg tgcaactgga | 2280 |
| cgcggggaga gcgctgcgac ttggacgaca gggatcgggc cgagttgagc cctctgttgc | 2340 |
| tgtccactac gcaatggcag gtcctcccct gctcattcac aacactgccc gccctgtcaa | 2400 |
| ctggcctgat acatctccac cagaacatcg tggacgtgca gtacctctat ggggttgagct | 2460 |
| cggcagtcac atcctgggtc ataaagtggg agtacgttgt gctcctcttc ttgctgctag | 2520 |
| cagatgctcg catttgtgcc tgcttgtgga tgatgcttct catatctcag gtagaggcgg | 2580 |
| cgctggagaa cttgatagtt ctcaacgctg cttccctagt cgggacacat ggcatcgtcc | 2640 |
| ccttcttcat cttttttgt gcagcttggt acctaaaagg caagtgggcc cctggactcg | 2700 |
| cctattccgt ctatgggatg tggccactgc tcctgcttct cctggcgttg ccccaacggg | 2760 |
| catacgcctt ggatcaggag ttggccgcgt cgtgtggggc cacggtcttc atctgcctag | 2820 |
| cggtgctcac tctatcgcca tattacaaac agtacatggc ccgcggcatc tggtggctgc | 2880 |
| agtacatgct gaccagagca gaggcgctcc tacaggtttg ggtcccccg ctcaacgccc | 2940 |
| gaggagggcg cgacggagtc gtactgctca cgtgtgtgct ccacccgcac ttgctctttg | 3000 |
| aaatcaccaa gatcatgctg gccattctcg ggcctttgtg gatcttgcag gccagtctgc | 3060 |
| tcaaggtacc gtacttcgtg cgcgttcagg gccttctccg gatctgcgcg ctagcgcgga | 3120 |
| agatggtcgg aggccattac gtgcaaatgg tcaccatcaa gttaggggcg ctcactggca | 3180 |
| cctatattta taaccatctc actcctcttc gggactgggc gcacaacggc ttgcaagacc | 3240 |
| tagccgtagc tgtggagcca gtcgtcttct cccaaatgga gaccaagctc atcacgtggg | 3300 |
| gggcagacac agccgcgtgt ggtgacatca tcaacggctt gcccgtctcc gcccgcaggg | 3360 |
| gccaggagat actgctcgga ccagccgatg gaatggcctc taggggatgg aggttgctgg | 3420 |
| cgcccatcac ggcgtacgct cagcagacaa ggggcctcct agggtgtata atcaccagcc | 3480 |
| tgactggccg ggacaagaac caagtggagg gtgaagtcca gattgtgtca actgctgccc | 3540 |
| aaacgttctt ggcgacgtgc atcaacgggg tatgctggac tgtctaccac ggggccggaa | 3600 |
| ccaggaccat tgcatcatcc aagggtcctg ttattctaat gtataccaat gtagaccaag | 3660 |
| acctcggggg ctggaccgct cctcaagtgc tcggctcact gacaccctgg gctgcggct | 3720 |
| cctcggacct ttacctggtc acgaggcatg ccgatgtcat tcccgtgccg cggcgaggtg | 3780 |
| aaaccagggg cagcctgctt tcgcccccggc ccatttccta tctaaaggga tcctcggag | 3840 |
| gccccctgct ctgtcccatg ggacatgccg tgggcatttt cagggccgcg tgtgcaccc | 3900 |
| gtggggtcgc aaaggcggtc gactttgtgc ccgttgagtc cttagagacc accatgaggt | 3960 |
| ccccagtgtt tactgacaat tccagccctc taacagtgcc ccagagttac caggtggcgc | 4020 |
| atctacatgc acccactggg agtggcaaga gcacgaaggt gccggccgct tacgcagctc | 4080 |
| aggggtacaa ggtacttgtg ctgaacccgt ctgttgctgc caccttaggg ttcggtgctt | 4140 |
| atatgtcaaa ggcccatggg atcgaccaa acatcaggac cggcgtgagg accatcacca | 4200 |
| caggctcccc catcacctac tccacctacg gcaaattttt ggctgatggc ggatgcccag | 4260 |
| gaggtgcgta cgacatcata atatgtgacg aatgtcactc agtggacgcc acctcgattc | 4320 |
| tgggcatagg gaccgtcttg gaccaagcgg agacggcggg ggtcaggctc actgtcctcg | 4380 |

-continued

```
ccaccgctac accacctggt tccgtcaccg tgccacattc caacatcgag gaagttgcac      4440
tgtccgctga cggggaaata ccattttatg gtaaggccat cccctaaac tacatcaagg       4500 ggggaggca cctcattttc tgccactcca agaagaagtg cgacgagctc gctgcaaagc       4560
tggtcggtcc gggcgtcaac gcggtggcct tttaccgtgg cctcgacgta tctgtcattc     4620
caactacagg agacgtcgtt gttgtagcga ccgacgcctt gatgactggc ttcaccggag     4680
atttcgactc tgtgatagac tgcaacacct gtgtcgtcca gacagtcgac ttcagcctag     4740
accctatatt ctctattgag acttccaccg tgccccagga cgccgtgtcc cgctcccaac     4800
ggaggggtag gaccggtcga gggaagcatg gtatttacag atatgtgtca cccggggagc     4860
ggccgtctgg catgttcgac tccgtggtcc tctgtgagtg ctatgacgcg ggttgtgctt     4920
ggtacgagct tacacccgcc gagaccacag tcaggctacg gcataccctc aacaccccag    4980
gattgcccgt gtgccaggac cacttggagt tctgggagag tgtcttcacc ggcctcaccc    5040
acatagatgc ccacttcctg tcccagacga aacagagtgg ggagaacttc ccctacctag    5100
tcgcatacca agccaccgtg tgcgctagag ctagagctcc tcccccgtca tgggaccaaa    5160
tgtggaagtg cctgatacgg ctcaagccca ccctcactgg ggctaccca ttactataca     5220 gactgggtag tgtacagaat gagatcacct taacacaccc aatcacccaa tacatcatgg    5280
cttgcatgtc ggcggacctg gaggtcgtca ctagcacgtg ggtgttggtg ggcggcgtcc    5340
tagccgcttt ggccgcttac tgcctgtcca caggcagcgt ggtcatagtg ggcaggataa    5400
tcctaggtgg gaagccggca gtcatacctg acagggaggt tctctaccga gagtttgatg    5460
agatggagga gtgcgccgcc cacgtcccct acctcgagca ggggatgcat ttggcggagc    5520
agttcaagca gaaagctctt gggttgctcc agacggcatc caaacaaaca gagacgatca    5580
ctcccattgt ccagtctaat tggcagaagc tcgagtcttt ctgggctaaa cacatgtgga    5640
acttcgttag cgggatacaa tatctggcgg gcctatcaac gctgcccggg aaccccgcta    5700
tagcatcgct gatgtcgttt acggccgcag tgacgagtcc actaaccact cagcagaccc    5760
tcctctttaa catcttgggg gggtggctgg ctgcccagct tgccgcccca gccgccgcca    5820
cagccttcgt tggcgcaggc attactggcg ccgttgttgg cagtgtgggc ctaggaaggg    5880
tcctggtgga cattcttgcc ggctacgggg ctggtgtggc cggggccctc gtggctttca    5940
aaatcatgag cggggagacc cccaccacgg aggatctagt caaccttctg cctgccatcc    6000
tatcgccagg agctctcgtt gtcgccgtgg tgtgcgcagc aatactacgc cggcacgtgg    6060
gccttggcga gggcgccgtg cagtggatga accggctgat agcgtttgct tctcggggta    6120
accacgtctc ccctacacac tacgtgccgg agagcgacgc gtcggctcgt gtcacaccaa    6180
ttctcaccag gctcactgtt actcagcttc tgaaagggcc ccacgtgtgg ataagctcga    6240
attgcatcgc cccgtgtgct agttcttggc ttaaagatgt ctggaactgg atatgcgagg    6300
tgctgagcga cttcaagaat tggctgaagg ccaaacttgt accacaactg cccgggatcc    6360
cattcgtatc ctgccaacgc gggtaccgtg gggtctggcg gggcgagggc atcgtgcaca    6420
ctcgttgccc gtgtggggcc aatataactg gacatgtcaa gaacggttcg atgagaatcg    6480
tcgggcctaa gacttgcagc aacacctggc gtgggtcgtt ccccattaac gcttacacta    6540
caggcccgtg cacgccctcc ccggcgccga ctatacgtt cgcgctatgg aggtgtctg      6600 cagaggagta tgtggaggta aggcggctgg gggacttcca ttacgtcacg ggggtgacca    6660
ctgataaact caagtgtcca tgccaggtcc cctcacccga gttctccaca gaggtggacg    6720
gggtgcgcct gcataggtac gcccctcccct gcaaacccct gctacgggat gaggtgacgt    6780
```

```
ttagcgtcgg gttcaatgaa tacctggtgg ggtcccagtt gccctgcgag cccgagccag   6840
acgtagcagc attaacatca atgcttacag acccttccca catcactgca aagacggcgg   6900
cgcgtaggct gaagcggggg tctccccct ccctggccag ttcttctgcc agccagctgt   6960
ccgcgccgtc actgaaagca acatgcacca ctcaccatga ctctccagac gccgacctca   7020
tagaagccaa cctcctgtgg agacgggaga tggggggaa catcaccaga gtggagtcgg   7080
agaacaagat tgttgttctg gattctttcg acccgctcgt ggcagaggag gatgaccggg   7140
agatttctat tccagctgag attctgcgga aatttaagca gtttcccccc gccatgccca   7200
tatgggcacg gccggattat aatcctcccc ttgtggaacc gtggaagcgc ccggactgtg   7260
atccacccttt agtccacggg tgcccctac cacctcccaa gccgactccg gtgccgccac   7320
cccggaaaaa gaggacggtg gtgctggacg agtctacagt atcatctgct ctggctgagc   7380
ttgccactaa gaccttcggc agctctacaa cctcaggcgt gacaagtggt gaagcggccg   7440
aatcgtcccc ggcgctttcc tgcgacggtg agctggactc cgaagctgaa tcttactcct   7500
ccatgccccc tctcgagggg gaaccggggg accccgatct cagcgacggg tcttggtcta   7560
ccgtgagcag tgatggcggt acggaggatg tcgtgtgctg ctcgatgtcc tactcgtgga   7620
cgggcgcctt aattacgccc tgtgccgcag aggaaaccaa actccccatc aacgcactga   7680
gtaactcgct gctgcgccac acaatttggg tgtattccac cacctctcgc agcgctggca   7740
agaggcagaa aaaagtcaca tttgacaggc tgcaggtcct ggacgatcat taccgggacg   7800
tgctcaagga ggctaaggcc aaggcatcca cagtgaaggc taaattgcta tccgtagagg   7860
aggcatgtag cctgacgccc ccgcactccg ccagatcaaa atttggctat gggccgaagg   7920
atgtccgaag ccattccagt aaggctatac gccacatcaa ctccgtgtgg caggaccttc   7980
tggaggacaa tacaacacct atagacacta ccatcatggc caagaatgaa gtcttctgcg   8040
tgaaggccga aaaaggggt cgcaagcccg ctcgccttat cgtgtacccc gacctggggg   8100
tgcgcgtgtg cgagaagaga gctttgtatg acgtagtcaa acagctcccc attgccgtga   8160
tgggaccctc ctacgggttc cagtactcgc cagcgcagcg ggtcgacttc ctgcttaacg   8220
cgtggaaatc aaagaaaaac cctatggggt tttcctatga cacccgttgc tttgactcaa   8280
cagtcactga ggctgatatc cgtacggagg aagacctcta tcaatcttgt gacctggtcc   8340
ctgaggcccg cgcggccata aggtctctca cagagaggct ttacatcggg ggcccactta   8400
ccaattctaa gggacaaaac tgcggctatc ggcgatgccg cgcaagcggc gtgctgacca   8460
ctagctgcgg taacaccata acttgctacc ttaaggctag tgcggcctgt cgagctgcaa   8520
agctccagga ctgcaccatg ctcgtgtgcg gcgacgacct cgtcgttatc tgtgaaagcg   8580
ccggtgtcaa ggaggacgct gcgagcctga gagccttcac cgaggctatg accaggtact   8640
ccggcccccc gggagacccg gctcaaccag aatacgactt ggagcttata acatcctgct   8700
cctccaatgt gtcggtcgcg cgcgacggcg ctggccaaag ggtctattat ctgacccgtg   8760
aacctgagac tccctcgcg cgtgccgctt gggagacagc aagacacact ccagtgaact   8820
cctggctagg caacatcatc atgtttgccc ccactctgtg ggtacggatg gtcctcatga   8880
cccacttatt ctccatactc atagttcagg agcaccttga aaaggctcta gattgtgaaa   8940
tctatggagc cacacactcc gtcccaccgt tggacctacc tgaaatcatt caaagactcc   9000
atggcctcag cgcgttttcg ctccacagtt actctccagg tgaaatcaat agggtggctt   9060
catgcctcag gaaacttggg gttccaccct tgcgagcttg agacaccgg gcccggagcg   9120
```

```
tccgcgccac actcctatcc caggggggga aagccgccat atgcggtaag tacctcttca    9180
actgggcggt gaaaaccaaa ctcaaactca ttccattacc gctcgcgtct catttggact    9240
tgtccaattg gttcacgggc ggctacagcg ggggagacat ttatcacagc gtgtctcatg    9300
cccggccccg ttggtttctc tggtgcctac tcctactctc agtaggggta ggcatctacc    9360
tccttcccaa ccgatagacg gttgggcaac cactccaggc ctttaggccc tatttaaaca    9420
ctccaggcct ttaggcccg t                                               9441
```

<210> SEQ ID NO 2
<211> LENGTH: 3011
<212> TYPE: PRT
<213> ORGANISM: Hepatitis C virus

<400> SEQUENCE: 2

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Tyr
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Gly Val Arg Asn Ser Ser Gly Val Tyr His Val Thr Asn Asp Cys Pro
        195                 200                 205

Asn Ala Ser Val Val Tyr Glu Thr Asp Ser Leu Ile Ile His Leu Pro
    210                 215                 220

Gly Cys Val Pro Cys Val Arg Glu Gly Asn Gly Ser Arg Cys Trp Val
225                 230                 235                 240

Ser Leu Ser Pro Thr Val Ala Ala Lys Asp Pro Gly Val Pro Val Asn
                245                 250                 255

Glu Ile Arg Arg His Val Asp Leu Ile Ala Gly Ala Ala Ala Phe Cys
            260                 265                 270

Ser Ala Met Tyr Val Gly His Leu Cys Gly Ser Ile Phe Leu Val Gly
        275                 280                 285

Gln Leu Phe Thr Leu Ser Pro Arg Arg His Trp Thr Thr Gln Asp Cys
    290                 295                 300

Asn Cys Ser Ile Tyr Pro Gly His Val Thr Gly His Arg Met Ala Trp
305                 310                 315                 320
```

```
Asp Met Met Met Asn Trp Ser Pro Thr Thr Ala Leu Val Ala Gln
            325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
            355                 360                 365

Thr Lys Val Leu Val Leu Leu Phe Ala Gly Val Asp Ala Thr
            370                 375                 380

Thr Ile Val Ser Gly Gly Ser Ala Gly Arg Ser Thr Ala Gly Leu Val
385                 390                 395                 400

Gly Leu Phe Ser Pro Gly Ala Arg Gln Asn Ile Gln Leu Ile Asn Thr
            405                 410                 415

Asn Gly Ser Trp His Ile Asn Arg Thr Ala Leu Asn Cys Asn Asp Thr
            420                 425                 430

Leu Gln Thr Gly Trp Val Ala Gly Leu Phe Tyr Thr Asn Lys Phe Asn
            435                 440                 445

Ser Ser Gly Cys Pro Glu Arg Leu Ala Ser Cys Arg Pro Leu Ala Asp
    450                 455                 460

Phe Asp Gln Gly Trp Gly Pro Ile Ser Tyr Thr Asn Gly Ser Gly Pro
465                 470                 475                 480

Asp Gln Arg Pro Tyr Cys Trp His Tyr Pro Pro Lys Pro Cys Gly Ile
            485                 490                 495

Val Pro Ala Glu Ser Val Cys Gly Pro Val Tyr Cys Phe Thr Pro Ser
            500                 505                 510

Pro Val Val Val Gly Thr Thr Asp Arg Ser Gly Ala Pro Thr Tyr Asn
            515                 520                 525

Trp Gly Glu Asn Glu Thr Asp Val Phe Val Leu Asn Asn Thr Arg Pro
            530                 535                 540

Arg Leu Gly Asn Trp Phe Gly Gly Thr Trp Met Asn Ser Thr Gly Phe
545                 550                 555                 560

Thr Lys Val Cys Gly Ala Pro Pro Cys Ala Ile Gly Gly Val Gly Asn
            565                 570                 575

Asn Thr Leu Tyr Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
            595                 600                 605

Ile His Tyr Pro Tyr Arg Leu Trp His Tyr Pro Cys Thr Ile Asn Tyr
            610                 615                 620

Thr Ile Phe Lys Ile Arg Met Phe Val Gly Gly Val Glu His Arg Leu
625                 630                 635                 640

Asp Ala Ala Cys Asn Trp Thr Arg Gly Glu Arg Cys Asp Leu Asp Asp
            645                 650                 655

Arg Asp Arg Ala Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Leu Ser Ser Ala Val Thr Ser Trp Val Ile Lys Trp Glu Tyr Val Val
705                 710                 715                 720

Leu Leu Phe Leu Leu Leu Ala Asp Ala Arg Ile Cys Ala Cys Leu Trp
            725                 730                 735
```

```
Met Met Leu Leu Ile Ser Gln Val Glu Ala Ala Leu Glu Asn Leu Ile
            740                 745                 750

Val Leu Asn Ala Ala Ser Leu Val Gly Thr His Gly Ile Val Pro Phe
            755                 760                 765

Phe Ile Phe Phe Cys Ala Ala Trp Tyr Leu Lys Gly Lys Trp Ala Pro
            770                 775                 780

Gly Leu Ala Tyr Ser Val Tyr Gly Met Trp Pro Leu Leu Leu Leu
785                 790                 795                 800

Leu Ala Leu Pro Gln Arg Ala Tyr Ala Leu Asp Gln Glu Leu Ala Ala
                805                 810                 815

Ser Cys Gly Ala Thr Val Phe Ile Cys Leu Ala Val Leu Thr Leu Ser
            820                 825                 830

Pro Tyr Tyr Lys Gln Tyr Met Ala Arg Gly Ile Trp Trp Leu Gln Tyr
            835                 840                 845

Met Leu Thr Arg Ala Glu Ala Leu Leu Gln Val Trp Val Pro Pro Leu
            850                 855                 860

Asn Ala Arg Gly Gly Arg Asp Gly Val Val Leu Leu Thr Cys Val Leu
865                 870                 875                 880

His Pro His Leu Leu Phe Glu Ile Thr Lys Ile Met Leu Ala Ile Leu
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Met
            915                 920                 925

Val Gly Gly His Tyr Val Gln Met Val Thr Ile Lys Leu Gly Ala Leu
            930                 935                 940

Thr Gly Thr Tyr Ile Tyr Asn His Leu Thr Pro Leu Arg Asp Trp Ala
945                 950                 955                 960

His Asn Gly Leu Gln Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
            995                 1000                1005

Glu Ile Leu Leu Gly Pro Ala Asp Gly Met Ala Ser Arg Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Ala Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Ser Lys Gly Pro Val Ile
    1085                1090                1095

Leu Met Tyr Thr Asn Val Asp Gln Asp Leu Gly Gly Trp Thr Ala
    1100                1105                1110

Pro Gln Val Leu Gly Ser Leu Thr Pro Trp Ser Cys Gly Ser Ser
    1115                1120                1125

Asp Leu Tyr Leu Val Thr Arg His Ala Asp Val Ile Pro Val Pro
    1130                1135                1140

Arg Arg Gly Glu Thr Arg Gly Ser Leu Leu Ser Pro Arg Pro Ile
```

-continued

```
            1145                1150                1155
Ser Tyr Leu Lys Gly Ser Ser Gly Gly Pro Leu Leu Cys Pro Met
    1160                1165                1170

Gly His Ala Val Gly Ile Phe Arg Ala Ala Val Cys Thr Arg Gly
    1175                1180                1185

Val Ala Lys Ala Val Asp Phe Val Pro Val Glu Ser Leu Glu Thr
    1190                1195                1200

Thr Met Arg Ser Pro Val Phe Thr Asp Asn Ser Ser Pro Leu Thr
    1205                1210                1215

Val Pro Gln Ser Tyr Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Ile Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Pro Gly Gly
    1295                1300                1305

Ala Tyr Asp Ile Ile Ile Cys Asp Glu Cys His Ser Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Val Pro His Ser Asn Ile Glu Glu Val Ala Leu Ser
    1355                1360                1365

Ala Asp Gly Glu Ile Pro Phe Tyr Gly Lys Ala Ile Pro Leu Asn
    1370                1375                1380

Tyr Ile Lys Gly Gly Arg His Leu Ile Phe Cys His Ser Lys Lys
    1385                1390                1395

Lys Cys Asp Glu Leu Ala Ala Lys Leu Val Gly Pro Gly Val Asn
    1400                1405                1410

Ala Val Ala Phe Tyr Arg Gly Leu Asp Val Ser Val Ile Pro Thr
    1415                1420                1425

Thr Gly Asp Val Val Val Ala Thr Asp Ala Leu Met Thr Gly
    1430                1435                1440

Phe Thr Gly Asp Phe Asp Ser Val Ile Asp Cys Asn Thr Cys Val
    1445                1450                1455

Val Gln Thr Val Asp Phe Ser Leu Asp Pro Ile Phe Ser Ile Glu
    1460                1465                1470

Thr Ser Thr Val Pro Gln Asp Ala Val Ser Arg Ser Gln Arg Arg
    1475                1480                1485

Gly Arg Thr Gly Arg Gly Lys His Gly Ile Tyr Arg Tyr Val Ser
    1490                1495                1500

Pro Gly Glu Arg Pro Ser Gly Met Phe Asp Ser Val Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Leu Asn Thr Pro Gly Leu
    1535                1540                1545
```

-continued

```
Pro Val Cys Gln Asp His Leu Glu Phe Trp Glu Ser Val Phe Thr
1550                1555                1560
Gly Leu Thr His Ile Asp Ala His Phe Leu Ser Gln Thr Lys Gln
1565                1570                1575
Ser Gly Glu Asn Phe Pro Tyr Leu Val Ala Tyr Gln Ala Thr Val
1580                1585                1590
Cys Ala Arg Ala Arg Ala Pro Pro Ser Trp Asp Gln Met Trp
1595                1600                1605
Lys Cys Leu Ile Arg Leu Lys Pro Thr Leu Thr Gly Ala Thr Pro
1610                1615                1620
Leu Leu Tyr Arg Leu Gly Ser Val Gln Asn Glu Ile Thr Leu Thr
1625                1630                1635
His Pro Ile Thr Gln Tyr Ile Met Ala Cys Met Ser Ala Asp Leu
1640                1645                1650
Glu Val Val Thr Ser Thr Trp Val Leu Val Gly Val Leu Ala
1655                1660                1665
Ala Leu Ala Ala Tyr Cys Leu Ser Thr Gly Ser Val Val Ile Val
1670                1675                1680
Gly Arg Ile Ile Leu Gly Gly Lys Pro Ala Val Ile Pro Asp Arg
1685                1690                1695
Glu Val Leu Tyr Arg Glu Phe Asp Glu Met Glu Glu Cys Ala Ala
1700                1705                1710
His Val Pro Tyr Leu Glu Gln Gly Met His Leu Ala Glu Gln Phe
1715                1720                1725
Lys Gln Lys Ala Leu Gly Leu Leu Gln Thr Ala Ser Lys Gln Thr
1730                1735                1740
Glu Thr Ile Thr Pro Ile Val Gln Ser Asn Trp Gln Lys Leu Glu
1745                1750                1755
Ser Phe Trp Ala Lys His Met Trp Asn Phe Val Ser Gly Ile Gln
1760                1765                1770
Tyr Leu Ala Gly Leu Ser Thr Leu Pro Gly Asn Pro Ala Ile Ala
1775                1780                1785
Ser Leu Met Ser Phe Thr Ala Ala Val Thr Ser Pro Leu Thr Thr
1790                1795                1800
Gln Gln Thr Leu Leu Phe Asn Ile Leu Gly Gly Trp Leu Ala Ala
1805                1810                1815
Gln Leu Ala Ala Pro Ala Ala Thr Ala Phe Val Gly Ala Gly
1820                1825                1830
Ile Thr Gly Ala Val Val Gly Ser Val Gly Leu Gly Lys Val Leu
1835                1840                1845
Val Asp Ile Leu Ala Gly Tyr Gly Ala Gly Val Ala Gly Ala Leu
1850                1855                1860
Val Ala Phe Lys Ile Met Ser Gly Glu Thr Pro Thr Thr Glu Asp
1865                1870                1875
Leu Val Asn Leu Leu Pro Ala Ile Leu Ser Pro Gly Ala Leu Val
1880                1885                1890
Val Ala Val Val Cys Ala Ala Ile Leu Arg Arg His Val Gly Leu
1895                1900                1905
Gly Glu Gly Ala Val Gln Trp Met Asn Arg Leu Ile Ala Phe Ala
1910                1915                1920
Ser Arg Gly Asn His Val Ser Pro Thr His Tyr Val Pro Glu Ser
1925                1930                1935
```

-continued

Asp Ala Ser Ala Arg Val Thr Pro Ile Leu Thr Arg Leu Thr Val
1940                1945                1950

Thr Gln Leu Leu Lys Gly Leu His Val Trp Ile Ser Ser Asn Cys
1955                1960                1965

Ile Ala Pro Cys Ala Ser Ser Trp Leu Lys Asp Val Trp Asn Trp
1970                1975                1980

Ile Cys Glu Val Leu Ser Asp Phe Lys Asn Trp Leu Lys Ala Lys
1985                1990                1995

Leu Val Pro Gln Leu Pro Gly Ile Pro Phe Val Ser Cys Gln Arg
2000                2005                2010

Gly Tyr Arg Gly Val Trp Arg Gly Glu Gly Ile Val His Thr Arg
2015                2020                2025

Cys Pro Cys Gly Ala Asn Ile Thr Gly His Val Lys Asn Gly Ser
2030                2035                2040

Met Arg Ile Val Gly Pro Lys Thr Cys Ser Asn Thr Trp Arg Gly
2045                2050                2055

Ser Phe Pro Ile Asn Ala Tyr Thr Thr Gly Pro Cys Thr Pro Ser
2060                2065                2070

Pro Ala Pro Asn Tyr Thr Phe Ala Leu Trp Arg Val Ser Ala Glu
2075                2080                2085

Glu Tyr Val Glu Val Arg Arg Leu Gly Asp Phe His Tyr Val Thr
2090                2095                2100

Gly Val Thr Thr Asp Lys Leu Lys Cys Pro Cys Gln Val Pro Ser
2105                2110                2115

Pro Glu Phe Ser Thr Glu Val Asp Gly Val Arg Leu His Arg Tyr
2120                2125                2130

Ala Pro Pro Cys Lys Pro Leu Leu Arg Asp Glu Val Thr Phe Ser
2135                2140                2145

Val Gly Phe Asn Glu Tyr Leu Val Gly Ser Gln Leu Pro Cys Glu
2150                2155                2160

Pro Glu Pro Asp Val Ala Ala Leu Thr Ser Met Leu Thr Asp Pro
2165                2170                2175

Ser His Ile Thr Ala Lys Thr Ala Ala Arg Arg Leu Lys Arg Gly
2180                2185                2190

Ser Pro Pro Ser Leu Ala Ser Ser Ser Ala Ser Gln Leu Ser Ala
2195                2200                2205

Pro Ser Leu Lys Ala Thr Cys Thr Thr His His Asp Ser Pro Asp
2210                2215                2220

Ala Asp Leu Ile Glu Ala Asn Leu Leu Trp Arg Arg Glu Met Gly
2225                2230                2235

Gly Asn Ile Thr Arg Val Glu Ser Glu Asn Lys Ile Val Val Leu
2240                2245                2250

Asp Ser Phe Asp Pro Leu Val Ala Glu Glu Asp Arg Glu Ile
2255                2260                2265

Ser Ile Pro Ala Glu Ile Leu Arg Lys Phe Lys Gln Phe Pro Pro
2270                2275                2280

Ala Met Pro Ile Trp Ala Arg Pro Asp Tyr Asn Pro Pro Leu Val
2285                2290                2295

Glu Pro Trp Lys Arg Pro Asp Cys Asp Pro Pro Leu Val His Gly
2300                2305                2310

Cys Pro Leu Pro Pro Pro Lys Pro Thr Pro Val Pro Pro Pro Arg
2315                2320                2325

Lys Lys Arg Thr Val Val Leu Asp Glu Ser Thr Val Ser Ser Ala

-continued

```
              2330                2335                2340
Leu Ala Glu Leu Ala Thr Lys Thr Phe Gly Ser Ser Thr Thr Ser
        2345                2350                2355
Gly Val Thr Ser Gly Glu Ala Ala Glu Ser Ser Pro Ala Leu Ser
        2360                2365                2370
Cys Asp Gly Glu Leu Asp Ser Glu Ala Glu Ser Tyr Ser Ser Met
        2375                2380                2385
Pro Pro Leu Glu Gly Glu Pro Gly Asp Pro Asp Leu Ser Asp Gly
        2390                2395                2400
Ser Trp Ser Thr Val Ser Ser Asp Gly Gly Thr Glu Asp Val Val
        2405                2410                2415
Cys Cys Ser Met Ser Tyr Ser Trp Thr Gly Ala Leu Ile Thr Pro
        2420                2425                2430
Cys Ala Ala Glu Glu Thr Lys Leu Pro Ile Asn Ala Leu Ser Asn
        2435                2440                2445
Ser Leu Leu Arg His His Asn Leu Val Tyr Ser Thr Thr Ser Arg
        2450                2455                2460
Ser Ala Gly Lys Arg Gln Lys Lys Val Thr Phe Asp Arg Leu Gln
        2465                2470                2475
Val Leu Asp Asp His Tyr Arg Asp Val Leu Lys Glu Ala Lys Ala
        2480                2485                2490
Lys Ala Ser Thr Val Lys Ala Lys Leu Leu Ser Val Glu Glu Ala
        2495                2500                2505
Cys Ser Leu Thr Pro Pro His Ser Ala Arg Ser Lys Phe Gly Tyr
        2510                2515                2520
Gly Pro Lys Asp Val Arg Ser His Ser Ser Lys Ala Ile Arg His
        2525                2530                2535
Ile Asn Ser Val Trp Gln Asp Leu Leu Glu Asp Asn Thr Thr Pro
        2540                2545                2550
Ile Asp Thr Thr Ile Met Ala Lys Asn Glu Val Phe Cys Val Lys
        2555                2560                2565
Ala Glu Lys Gly Gly Arg Lys Pro Ala Arg Leu Ile Val Tyr Pro
        2570                2575                2580
Asp Leu Gly Val Arg Val Cys Glu Lys Arg Ala Leu Tyr Asp Val
        2585                2590                2595
Val Lys Gln Leu Pro Ile Ala Val Met Gly Pro Ser Tyr Gly Phe
        2600                2605                2610
Gln Tyr Ser Pro Ala Gln Arg Val Asp Phe Leu Leu Asn Ala Trp
        2615                2620                2625
Lys Ser Lys Lys Asn Pro Met Gly Phe Ser Tyr Asp Thr Arg Cys
        2630                2635                2640
Phe Asp Ser Thr Val Thr Glu Ala Asp Ile Arg Thr Glu Glu Asp
        2645                2650                2655
Leu Tyr Gln Ser Cys Asp Leu Val Pro Glu Ala Arg Ala Ala Ile
        2660                2665                2670
Arg Ser Leu Thr Glu Arg Leu Tyr Ile Gly Gly Pro Leu Thr Asn
        2675                2680                2685
Ser Lys Gly Gln Asn Cys Gly Tyr Arg Arg Cys Arg Ala Ser Gly
        2690                2695                2700
Val Leu Thr Thr Ser Cys Gly Asn Thr Ile Thr Cys Tyr Leu Lys
        2705                2710                2715
Ala Ser Ala Ala Cys Arg Ala Ala Lys Leu Gln Asp Cys Thr Met
        2720                2725                2730
```

```
Leu Val Cys Gly Asp Asp Leu Val Val Ile Cys Glu Ser Ala Gly
    2735                2740                2745

Val Lys Glu Asp Ala Ala Ser Leu Arg Ala Phe Thr Glu Ala Met
    2750                2755                2760

Thr Arg Tyr Ser Gly Pro Pro Gly Asp Pro Ala Gln Pro Glu Tyr
    2765                2770                2775

Asp Leu Glu Leu Ile Thr Ser Cys Ser Ser Asn Val Ser Val Ala
    2780                2785                2790

Arg Asp Gly Ala Gly Gln Arg Val Tyr Tyr Leu Thr Arg Glu Pro
    2795                2800                2805

Glu Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Val Arg Met Val Leu Met Thr His Leu Phe Ser Ile Leu
    2840                2845                2850

Ile Val Gln Glu His Leu Glu Lys Ala Leu Asp Cys Glu Ile Tyr
    2855                2860                2865

Gly Ala Thr His Ser Val Pro Pro Leu Asp Leu Pro Glu Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ser Cys Leu Arg Lys Leu Gly
    2900                2905                2910

Val Pro Pro Leu Arg Ala Trp Arg His Arg Ala Arg Ser Val Arg
    2915                2920                2925

Ala Thr Leu Leu Ser Gln Gly Gly Lys Ala Ala Ile Cys Gly Lys
    2930                2935                2940

Tyr Leu Phe Asn Trp Ala Val Lys Thr Lys Leu Lys Leu Ile Pro
    2945                2950                2955

Leu Pro Leu Ala Ser His Leu Asp Leu Ser Asn Trp Phe Thr Gly
    2960                2965                2970

Gly Tyr Ser Gly Gly Asp Ile Tyr His Ser Val Ser His Ala Arg
    2975                2980                2985

Pro Arg Trp Phe Leu Trp Cys Leu Leu Leu Leu Ser Val Gly Val
    2990                2995                3000

Gly Ile Tyr Leu Leu Pro Asn Arg
    3005                3010

<210> SEQ ID NO 3
<211> LENGTH: 341
<212> TYPE: DNA
<213> ORGANISM: Hepatitis C virus

<400> SEQUENCE: 3
gccagccccc tgatggggc gacactccgc catgaatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gataaacccg ctcaacgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac c                         341
```

```
<210> SEQ ID NO 4
<211> LENGTH: 67
<212> TYPE: DNA
<213> ORGANISM: Hepatitis C virus

<400> SEQUENCE: 4
tagacggttg ggcaaccact ccaggccttt aggccctatt taaacactcc aggcctttag    60
gccccgt                                                              67

<210> SEQ ID NO 5
<211> LENGTH: 573
<212> TYPE: DNA
<213> ORGANISM: Hepatitis C virus

<400> SEQUENCE: 5
atgagcacga atcctaaacc tcaaagaaaa accaaacgta acaccaaccg tcgcccacag    60
gacgtcaagt tcccgggtgg cggacagatc gttggtggag tttacttgtt gccgcgcagg   120
ggccctagat tgggtgtgcg cgcgacgagg aagacttccg agcggtcgca acctcgaggt   180
agacgtcagc ctatcccccaa ggcacgtcgg cccgagggca ggacctgggc tcagcccggg   240
taccctcggc ccctctatgg caatgagggc tgcgggtggg cgggatggct cctgtctccc   300
cgcggctctc ggcctagttg gggccccaca ccccccggc gtagatcgcg caatttgggt    360
aaggtcatcg ataccttac gtatggcttc gccgacctca tggggtacat accgctcgtc   420 ggcgccccc ttggggggcgc tgccagggcc ctggcgcacg gcgtccgggt cctggaagac    480
ggcgtgaact atgcaacagg gaaccttcct ggttgctctt tctctatctt ccttctggcc   540
ctgctctctt gcttgactgt gcccgcttcg gcc                                 573

<210> SEQ ID NO 6
<211> LENGTH: 191
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Tyr
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

Phe Leu Leu Ala Leu Leu Ser Cys Leu Thr Val Pro Ala Ser Ala
            180                 185                 190

<210> SEQ ID NO 7
<211> LENGTH: 576
<212> TYPE: DNA
<213> ORGANISM: Hepatitis C virus

<400> SEQUENCE: 7

| | |
|---|---:|
| gtcggagtgc gcaactcttc gggggtgtac catgtcacca atgattgccc caatgcgtct | 60 |
| gttgtgtacg agacagatag cttgatcata catctgccgg ggtgtgtgcc ctgcgtacgc | 120 |
| gagggcaacg gttcgaggtg ctgggtctcc cttagtccta ctgttgccgc taaggatccg | 180 |
| ggcgtcccgg tcaacgagat tcggcgtcac gtcgacctga ttgccggggc cgctgcattc | 240 |
| tgttcggcta tgtatgtagg gcacttatgc ggttccatct tcctcgttgg ccagcttttc | 300 |
| accctctccc ctaggcgcca ctggacaaca caagactgta attgctccat ctacccagga | 360 |
| catgtgacag ccatcgaatg gcttgggac atgatgatga actggtcccc tacgacggcg | 420 |
| ctggtagtag cccagctgct ccggatccca caagccatct tggacatgat cgctggtgct | 480 |
| cactggggag tcctggcggg catagcgtat ttctccatgg tggggaactg gacgaaggtc | 540 |
| ctggtagtgc tgctgctatt tgccggcgtc gacgcg | 576 |

<210> SEQ ID NO 8
<211> LENGTH: 192
<212> TYPE: PRT
<213> ORGANISM: Hepatitis C virus

<400> SEQUENCE: 8

Val Gly Val Arg Asn Ser Ser Gly Val Tyr His Val Thr Asn Asp Cys
1               5                   10                  15

Pro Asn Ala Ser Val Val Tyr Glu Thr Asp Ser Leu Ile Ile His Leu
            20                  25                  30

Pro Gly Cys Val Pro Cys Val Arg Glu Gly Asn Gly Ser Arg Cys Trp
        35                  40                  45

Val Ser Leu Ser Pro Thr Val Ala Ala Lys Asp Pro Gly Val Pro Val
    50                  55                  60

Asn Glu Ile Arg Arg His Val Asp Leu Ile Ala Gly Ala Ala Ala Phe
65                  70                  75                  80

Cys Ser Ala Met Tyr Val Gly His Leu Cys Gly Ser Ile Phe Leu Val
                85                  90                  95

Gly Gln Leu Phe Thr Leu Ser Pro Arg Arg His Trp Thr Thr Gln Asp
            100                 105                 110

Cys Asn Cys Ser Ile Tyr Pro Gly His Val Thr Gly His Arg Met Ala
        115                 120                 125

Trp Asp Met Met Asn Trp Ser Pro Thr Thr Ala Leu Val Val Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Thr Lys Val Leu Val Val Leu Leu Leu Phe Ala Gly Val Asp Ala
            180                 185                 190

<210> SEQ ID NO 9
<211> LENGTH: 1278

<212> TYPE: DNA
<213> ORGANISM: Hepatitis C virus

<400> SEQUENCE: 9

```
acgaccatcg tctccggggg aagtgccggc cgcagcacgg ctggacttgt tgggctcttc      60
tcaccaggcg cccggcagaa catccagctg atcaacacca acggcagttg cacatcaac     120
cgcacggccc tgaactgcaa tgataccctt caaaccggct gggtagcagg gcttttctat     180
accaacaaat tcaactcttc ggggttgccccc gagaggttgg ccagctgccg acccccttgcc    240
gactttgacc agggctgggg ccctatcagt tataccaacg gaagcggccc cgaccaacgc     300
ccctactgct ggcactaccc cccaaaacct tgtggtattg tgcccgcaga gagcgtgtgt     360
ggcccagtat actgcttcac tcccagcccc gtggtggtgg aacgaccga caggtcgggc      420
gcgcccacct acaactgggg tgaaaatgaa acggacgttt cgtcctcaa caacaccagg      480
ccacggctgg caattggtt cggtggtacc tggatgaact caactggatt caccaaggtg      540
tgcggagcgc cccttgtgc catcggaggg gtgggcaaca cacccttgta ctgccccact      600
gattgtttcc gcaaacatcc ggaagccacg tactctcggt gcggctccgg tccttggatt      660
acacccaggt gcttgatcca ctacccgtat aggctttggc attatccttg taccatcaat      720
tacaccatat tcaagatcag gatgtttgtg ggcggggttg agcacaggct cgacgccgcg      780
tgcaactgga cgcggggaga gcgctgcgac ttggacgaca gggatcgggc cgagttgagc      840
cctctgttgc tgtccactac gcaatggcag gtcctcccct gctcattcac aacactgccc      900
gccctgtcaa ctggcctgat acatctccac cagaacatcg tggacgtgca gtacctctat      960
gggttgagct cggcagtcac atcctgggtc ataaagtggg agtacgttgt gctcctcttc     1020
ttgctgctag cagatgctcg catttgtgcc tgcttgtgga tgatgcttct catatctcag     1080
gtagaggcgg cgctggagaa cttgatagtt ctcaacgctg cttccctagt cgggacacat     1140
ggcatcgtcc cttcttcat cttttttgt gcagcttggt acctaaaagg caagtgggcc     1200
cctggactcg cctattccgt ctatgggatg tggccactgc tcctgcttct cctggcgttg     1260
ccccaacggg catacgcc                                                  1278
```

<210> SEQ ID NO 10
<211> LENGTH: 426
<212> TYPE: PRT
<213> ORGANISM: Hepatitis C virus

<400> SEQUENCE: 10

```
Thr Thr Ile Val Ser Gly Gly Ser Ala Gly Arg Ser Thr Ala Gly Leu
  1               5                  10                  15

Val Gly Leu Phe Ser Pro Gly Ala Arg Gln Asn Ile Gln Leu Ile Asn
             20                  25                  30

Thr Asn Gly Ser Trp His Ile Asn Arg Thr Ala Leu Asn Cys Asn Asp
         35                  40                  45

Thr Leu Gln Thr Gly Trp Val Ala Gly Leu Phe Tyr Thr Asn Lys Phe
     50                  55                  60

Asn Ser Ser Gly Cys Pro Glu Arg Leu Ala Ser Cys Arg Pro Leu Ala
 65                  70                  75                  80

Asp Phe Asp Gln Gly Trp Gly Pro Ile Ser Tyr Thr Asn Gly Ser Gly
                 85                  90                  95

Pro Asp Gln Arg Pro Tyr Cys Trp His Tyr Pro Pro Lys Pro Cys Gly
            100                 105                 110

Ile Val Pro Ala Glu Ser Val Cys Gly Pro Val Tyr Cys Phe Thr Pro
```

```
                    115                 120                 125
Ser Pro Val Val Gly Thr Thr Asp Arg Ser Gly Ala Pro Thr Tyr
    130                 135                 140

Asn Trp Gly Glu Asn Glu Thr Asp Val Phe Val Leu Asn Asn Thr Arg
145                 150                 155                 160

Pro Arg Leu Gly Asn Trp Phe Gly Thr Trp Met Asn Ser Thr Gly
                165                 170                 175

Phe Thr Lys Val Cys Gly Ala Pro Cys Ala Ile Gly Gly Val Gly
                180                 185                 190

Asn Asn Thr Leu Tyr Cys Pro Thr Asp Cys Phe Arg Lys His Pro Glu
                195                 200                 205

Ala Thr Tyr Ser Arg Cys Gly Ser Gly Pro Trp Ile Thr Pro Arg Cys
    210                 215                 220

Leu Ile His Tyr Pro Tyr Arg Leu Trp His Tyr Pro Cys Thr Ile Asn
225                 230                 235                 240

Tyr Thr Ile Phe Lys Ile Arg Met Phe Val Gly Gly Val Glu His Arg
                245                 250                 255

Leu Asp Ala Ala Cys Asn Trp Thr Arg Gly Glu Arg Cys Asp Leu Asp
                260                 265                 270

Asp Arg Asp Arg Ala Glu Leu Ser Pro Leu Leu Leu Ser Thr Thr Gln
                275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Leu Ser Ser Ala Val Thr Ser Trp Val Ile Lys Trp Glu Tyr Val
                325                 330                 335

Val Leu Leu Phe Leu Leu Leu Ala Asp Ala Arg Ile Cys Ala Cys Leu
                340                 345                 350

Trp Met Met Leu Leu Ile Ser Gln Val Glu Ala Ala Leu Glu Asn Leu
        355                 360                 365

Ile Val Leu Asn Ala Ala Ser Leu Val Gly Thr His Gly Ile Val Pro
    370                 375                 380

Phe Phe Ile Phe Phe Cys Ala Ala Trp Tyr Leu Lys Gly Lys Trp Ala
385                 390                 395                 400

Pro Gly Leu Ala Tyr Ser Val Tyr Gly Met Trp Pro Leu Leu Leu Leu
                405                 410                 415

Leu Leu Ala Leu Pro Gln Arg Ala Tyr Ala
                420                 425

<210> SEQ ID NO 11
<211> LENGTH: 591
<212> TYPE: DNA
<213> ORGANISM: Hepatitis C virus

<400> SEQUENCE: 11
ttggatcagg agttggccgc gtcgtgtggg gccacggtct tcatctgcct agcggtgctc      60
actctatcgc catattacaa acagtacatg gcccgcggca tctggtggct gcagtacatg     120
ctgaccagag cagaggcgct cctacaggtt tgggtccccc cgctcaacgc ccgaggaggg     180
cgcgacggag tcgtactgct cacgtgtgtg ctccacccgc acttgctctt tgaaatcacc     240
aagatcatgc tggccattct cgggcctttg tggatcttgc aggccagtct gctcaaggta     300
ccgtacttcg tgcgcgttca gggccttctc cggatctgcg cgctagcgcg gaagatggtc     360
```

```
ggaggccatt acgtgcaaat ggtcaccatc aagttagggg cgctcactgg cacctatatt    420
tataaccatc tcactcctct tcgggactgg gcgcacaacg gcttgcaaga cctagccgta    480
gctgtggagc cagtcgtctt ctcccaaatg gagaccaagc tcatcacgtg ggggcagac    540 acagccgcgt gtggtgacat catcaacggc ttgcccgtct ccgcccgcag g             591
```

<210> SEQ ID NO 12
<211> LENGTH: 197
<212> TYPE: PRT
<213> ORGANISM: Hepatitis C virus

<400> SEQUENCE: 12

```
Leu Asp Gln Glu Leu Ala Ala Ser Cys Gly Ala Thr Val Phe Ile Cys
1               5                   10                  15

Leu Ala Val Leu Thr Leu Ser Pro Tyr Tyr Lys Gln Tyr Met Ala Arg
            20                  25                  30

Gly Ile Trp Trp Leu Gln Tyr Met Leu Thr Arg Ala Glu Ala Leu Leu
        35                  40                  45

Gln Val Trp Val Pro Pro Leu Asn Ala Arg Gly Gly Arg Asp Gly Val
    50                  55                  60

Val Leu Leu Thr Cys Val Leu His Pro His Leu Phe Glu Ile Thr
65                  70                  75                  80

Lys Ile Met Leu Ala Ile Leu Gly Pro Leu Trp Ile Leu Gln Ala Ser
                85                  90                  95

Leu Leu Lys Val Pro Tyr Phe Val Arg Val Gln Gly Leu Leu Arg Ile
            100                 105                 110

Cys Ala Leu Ala Arg Lys Met Val Gly Gly His Tyr Val Gln Met Val
        115                 120                 125

Thr Ile Lys Leu Gly Ala Leu Thr Gly Thr Tyr Ile Tyr Asn His Leu
    130                 135                 140

Thr Pro Leu Arg Asp Trp Ala His Asn Gly Leu Gln Asp Leu Ala Val
145                 150                 155                 160

Ala Val Glu Pro Val Val Phe Ser Gln Met Glu Thr Lys Leu Ile Thr
                165                 170                 175

Trp Gly Ala Asp Thr Ala Ala Cys Gly Asp Ile Ile Asn Gly Leu Pro
            180                 185                 190

Val Ser Ala Arg Arg
        195
```

<210> SEQ ID NO 13
<211> LENGTH: 1953
<212> TYPE: DNA
<213> ORGANISM: Hepatitis C virus

<400> SEQUENCE: 13

```
ggccaggaga tactgctcgg accagccgat ggaatggcct ctaggggatg gaggttgctg    60
gcgcccatca cggcgtacgc tcagcagaca aggggcctcc tagggtgtat aatcaccagc    120
ctgactggcc gggacaagaa ccaagtggag ggtgaagtcc agattgtgtc aactgctgcc    180
caaacgttct tggcgacgtg catcaacggg gtatgctgga ctgtctacca cggggccgga    240
accaggacca ttgcatcatc caagggtcct gttattctaa tgtataccaa tgtagaccaa    300
gacctcgggg gctggaccgc tcctcaagtg ctcggctcac tgacaccctg agctgcggc    360 tcctcggacc tttacctggt cacgaggcat gccgatgtca ttcccgtgcc gcggcgaggt    420
gaaaccaggg gcagcctgct ttcgccccgg cccatttcct atctaaaggg atcctcggga    480
```

```
ggcccctgc tctgtcccat gggacatgcc gtgggcattt tcagggccgc ggtgtgcacc      540
cgtggggtcg caaaggcggt cgactttgtg cccgttgagt ccttagagac caccatgagg      600
tccccagtgt ttactgacaa ttccagccct ctaacagtgc cccagagtta ccaggtggcg      660
catctacatg cacccactgg gagtggcaag agcacgaagg tgccggccgc ttacgcagct      720
caggggtaca aggtacttgt gctgaacccg tctgttgctg ccaccttagg gttcggtgct      780
tatatgtcaa aggcccatgg gatcgaccca aacatcagga ccggcgtgag gaccatcacc      840
acaggctccc ccatcaccta ctccacctac ggcaaatttt tggctgatgg cggatgccca      900
ggaggtgcgt acgacatcat aatatgtgac gaatgtcact cagtggacgc cacctcgatt      960
ctgggcatag gaccgtcttg gaccaagcg gagacggcgg gggtcaggct cactgtcctc     1020
gccaccgcta caccacctgg ttccgtcacc gtgccacatt ccaacatcga ggaagttgca     1080
ctgtccgctg acgggaaat accattttat ggtaaggcca tccccctaaa ctacatcaag     1140
gggggaggc acctcatttt ctgccactcc aagaagaagt cgacgagct cgctgcaaag     1200
ctggtcggtc cgggcgtcaa cgcggtggcc ttttaccgtg gcctcgacgt atctgtcatt     1260
ccaactacag agacgtcgt tgttgtagcg accgacgcct tgatgactgg cttcaccgga     1320
gatttcgact ctgtgataga ctgcaacacc tgtgtcgtcc agacagtcga cttcagccta     1380
gaccctatat tctctattga acttccacc gtgcccagg acgccgtgtc ccgctcccaa     1440
cggagggta ggaccggtcg agggaagcat ggtatttaca gatatgtgtc acccggggag     1500
cggccgtctg gcatgttcga ctccgtggtc tctgtgagt gctatgacgc gggttgtgct     1560
tggtacgagc ttacacccgc cgagaccaca gtcaggctac gggcatacct caacaccca     1620
ggattgcccg tgtgccagga ccacttggag ttctgggaga gtgtcttcac ggcctcacc     1680
cacatagatg cccacttcct gtcccagacg aaacagagtg gggagaactt ccctaccta     1740
gtcgcatacc aagccaccgt gtgcgctaga gctagagctc ctccccccgtc atgggaccaa     1800
atgtggaagt gcctgatacg gctcaagccc accctcactg gggctacccc attactatac     1860
agactgggta gtgtacagaa tgagatcacc ttaacacacc caatcaccca atacatcatg     1920
gcttgcatgt cggcggacct ggaggtcgtc act                                  1953
```

<210> SEQ ID NO 14
<211> LENGTH: 651
<212> TYPE: PRT
<213> ORGANISM: Hepatitis C virus

<400> SEQUENCE: 14

```
Gly Gln Glu Ile Leu Leu Gly Pro Ala Asp Gly Met Ala Ser Arg Gly
1               5                   10                  15

Trp Arg Leu Leu Ala Pro Ile Thr Ala Tyr Ala Gln Gln Thr Arg Gly
            20                  25                  30

Leu Leu Gly Cys Ile Ile Thr Ser Leu Thr Gly Arg Asp Lys Asn Gln
        35                  40                  45

Val Glu Gly Glu Val Gln Ile Val Ser Thr Ala Ala Gln Thr Phe Leu
    50                  55                  60

Ala Thr Cys Ile Asn Gly Val Cys Trp Thr Val Tyr His Gly Ala Gly
65                  70                  75                  80

Thr Arg Thr Ile Ala Ser Ser Lys Gly Pro Val Ile Leu Met Tyr Thr
                85                  90                  95

Asn Val Asp Gln Asp Leu Gly Gly Trp Thr Ala Pro Gln Val Leu Gly
            100                 105                 110
```

```
Ser Leu Thr Pro Trp Ser Cys Gly Ser Ser Asp Leu Tyr Leu Val Thr
        115                 120                 125

Arg His Ala Asp Val Ile Pro Val Pro Arg Arg Gly Glu Thr Arg Gly
    130                 135                 140

Ser Leu Leu Ser Pro Arg Pro Ile Ser Tyr Leu Lys Gly Ser Ser Gly
145                 150                 155                 160

Gly Pro Leu Leu Cys Pro Met Gly His Ala Val Gly Ile Phe Arg Ala
                165                 170                 175

Ala Val Cys Thr Arg Gly Val Ala Lys Ala Val Asp Phe Val Pro Val
            180                 185                 190

Glu Ser Leu Glu Thr Thr Met Arg Ser Pro Val Phe Thr Asp Asn Ser
        195                 200                 205

Ser Pro Leu Thr Val Pro Gln Ser Tyr Gln Val Ala His Leu His Ala
    210                 215                 220

Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255

Gly Phe Gly Ala Tyr Met Ser Lys Ala His Gly Ile Asp Pro Asn Ile
            260                 265                 270

Arg Thr Gly Val Arg Thr Ile Thr Thr Gly Ser Pro Ile Thr Tyr Ser
        275                 280                 285

Thr Tyr Gly Lys Phe Leu Ala Asp Gly Gly Cys Pro Gly Gly Ala Tyr
    290                 295                 300

Asp Ile Ile Ile Cys Asp Glu Cys His Ser Val Asp Ala Thr Ser Ile
305                 310                 315                 320

Leu Gly Ile Gly Thr Val Leu Asp Gln Ala Glu Thr Ala Gly Val Arg
                325                 330                 335

Leu Thr Val Leu Ala Thr Ala Thr Pro Pro Gly Ser Val Thr Val Pro
            340                 345                 350

His Ser Asn Ile Glu Glu Val Ala Leu Ser Ala Asp Gly Glu Ile Pro
        355                 360                 365

Phe Tyr Gly Lys Ala Ile Pro Leu Asn Tyr Ile Lys Gly Gly Arg His
    370                 375                 380

Leu Ile Phe Cys His Ser Lys Lys Lys Cys Asp Glu Leu Ala Ala Lys
385                 390                 395                 400

Leu Val Gly Pro Gly Val Asn Ala Val Ala Phe Tyr Arg Gly Leu Asp
                405                 410                 415

Val Ser Val Ile Pro Thr Thr Gly Asp Val Val Val Ala Thr Asp
            420                 425                 430

Ala Leu Met Thr Gly Phe Thr Gly Asp Phe Asp Ser Val Ile Asp Cys
        435                 440                 445

Asn Thr Cys Val Val Gln Thr Val Asp Phe Ser Leu Asp Pro Ile Phe
    450                 455                 460

Ser Ile Glu Thr Ser Thr Val Pro Gln Asp Ala Val Ser Arg Ser Gln
465                 470                 475                 480

Arg Arg Gly Arg Thr Gly Arg Gly Lys His Gly Ile Tyr Arg Tyr Val
                485                 490                 495

Ser Pro Gly Glu Arg Pro Ser Gly Met Phe Asp Ser Val Val Leu Cys
            500                 505                 510

Glu Cys Tyr Asp Ala Gly Cys Ala Trp Tyr Glu Leu Thr Pro Ala Glu
        515                 520                 525

Thr Thr Val Arg Leu Arg Ala Tyr Leu Asn Thr Pro Gly Leu Pro Val
```

```
            530             535             540
Cys Gln Asp His Leu Glu Phe Trp Glu Ser Val Phe Thr Gly Leu Thr
545                 550                 555                 560

His Ile Asp Ala His Phe Leu Ser Gln Thr Lys Gln Ser Gly Glu Asn
                565                 570                 575

Phe Pro Tyr Leu Val Ala Tyr Gln Ala Thr Val Cys Ala Arg Ala Arg
            580                 585                 590

Ala Pro Pro Ser Trp Asp Gln Met Trp Lys Cys Leu Ile Arg Leu
        595                 600                 605

Lys Pro Thr Leu Thr Gly Ala Thr Pro Leu Leu Tyr Arg Leu Gly Ser
    610                 615                 620

Val Gln Asn Glu Ile Thr Leu Thr His Pro Ile Thr Gln Tyr Ile Met
625                 630                 635                 640

Ala Cys Met Ser Ala Asp Leu Glu Val Val Thr
                645                 650
```

<210> SEQ ID NO 15
<211> LENGTH: 945
<212> TYPE: DNA
<213> ORGANISM: Hepatitis C virus

<400> SEQUENCE: 15

```
agcacgtggg tgttggtggg cggcgtccta gccgctttgg ccgcttactg cctgtccaca    60
ggcagcgtgg tcatagtggg caggataatc ctaggtggga agccggcagt catacctgac   120
agggaggttc tctaccgaga gtttgatgag atggaggagt cgccgcccca cgtcccctac   180
ctcgagcagg ggatgcattt ggcggagcag ttcaagcaga agctcttggg gttgctccag   240
acggcatcca aacaaacaga gacgatcact cccattgtcc agtctaattg cagaagctc    300
gagtctttct gggctaaaca catgtggaac ttcgttagcg ggatacaata tctggcgggc   360
ctatcaacgc tgcccgggaa ccccgctata gcatcgctga tgtcgtttac ggccgcagtg   420
acgagtccac taaccactca gcagaccctc ctctttaaca tcttgggggg gtggctggct   480
gcccagcttg ccgccccagc cgccgccaca gccttcgttg cgcaggcat  tactggcgcc    540
gttgttggca gtgtgggcct agggaaggtc ctggtggaca ttcttgccgg ctacggggct   600
ggtgtggccg ggcctctcgt ggctttcaaa atcatgagcg gggagacccc caccacggag   660
gatctagtca accttctgcc tgccatccta tcgccaggag ctctcgttgt cgccgtggtg   720
tgcgcagcaa tactacgccg gcacgtgggc cttggcgagg cgccgtgca gtggatgaac   780
cggctgatag cgtttgcttc tcggggtaac cacgtctccc ctacacacta cgtgccggag   840
agcgacgcgt cggctcgtgt cacaccaatt ctcaccaggc tcactgttac tcagcttctg   900
aaagggctcc acgtgtggat aagctcgaat tgcatcgccc cgtgt              945
```

<210> SEQ ID NO 16
<211> LENGTH: 315
<212> TYPE: PRT
<213> ORGANISM: Hepatitis C virus

<400> SEQUENCE: 16

```
Ser Thr Trp Val Leu Val Gly Gly Val Leu Ala Ala Leu Ala Ala Tyr
1               5                   10                  15

Cys Leu Ser Thr Gly Ser Val Val Ile Val Gly Arg Ile Ile Leu Gly
                20                  25                  30

Gly Lys Pro Ala Val Ile Pro Asp Arg Glu Val Leu Tyr Arg Glu Phe
            35                  40                  45
```

Asp Glu Met Glu Glu Cys Ala Ala His Val Pro Tyr Leu Glu Gln Gly
 50                  55                  60

Met His Leu Ala Glu Gln Phe Lys Gln Lys Ala Leu Gly Leu Leu Gln
 65                  70                  75                  80

Thr Ala Ser Lys Gln Thr Glu Thr Ile Thr Pro Ile Val Gln Ser Asn
             85                  90                  95

Trp Gln Lys Leu Glu Ser Phe Trp Ala Lys His Met Trp Asn Phe Val
            100                 105                 110

Ser Gly Ile Gln Tyr Leu Ala Gly Leu Ser Thr Leu Pro Gly Asn Pro
        115                 120                 125

Ala Ile Ala Ser Leu Met Ser Phe Thr Ala Ala Val Thr Ser Pro Leu
    130                 135                 140

Thr Thr Gln Gln Thr Leu Leu Phe Asn Ile Leu Gly Gly Trp Leu Ala
145                 150                 155                 160

Ala Gln Leu Ala Ala Pro Ala Ala Ala Thr Ala Phe Val Gly Ala Gly
                165                 170                 175

Ile Thr Gly Ala Val Val Gly Ser Val Gly Leu Gly Lys Val Leu Val
            180                 185                 190

Asp Ile Leu Ala Gly Tyr Gly Ala Gly Val Ala Gly Ala Leu Val Ala
        195                 200                 205

Phe Lys Ile Met Ser Gly Glu Thr Pro Thr Thr Glu Asp Leu Val Asn
    210                 215                 220

Leu Leu Pro Ala Ile Leu Ser Pro Gly Ala Leu Val Val Ala Val Val
225                 230                 235                 240

Cys Ala Ala Ile Leu Arg Arg His Val Gly Leu Gly Glu Gly Ala Val
                245                 250                 255

Gln Trp Met Asn Arg Leu Ile Ala Phe Ala Ser Arg Gly Asn His Val
            260                 265                 270

Ser Pro Thr His Tyr Val Pro Glu Ser Asp Ala Ser Ala Arg Val Thr
        275                 280                 285

Pro Ile Leu Thr Arg Leu Thr Val Thr Gln Leu Leu Lys Gly Leu His
    290                 295                 300

Val Trp Ile Ser Ser Asn Cys Ile Ala Pro Cys
305                 310                 315

<210> SEQ ID NO 17
<211> LENGTH: 3117
<212> TYPE: DNA
<213> ORGANISM: Hepatitis C virus

<400> SEQUENCE: 17
gctagttctt ggcttaaaga tgtctggaac tggatatgcg aggtgctgag cgacttcaag      60
aattggctga aggccaaact tgtaccacaa ctgcccggga tcccattcgt atcctgccaa     120
cgcgggtacc gtggggtctg gcggggcgag ggcatcgtgc acactcgttg cccgtgtggg     180
gccaatataa ctggacatgt caagaacggt tcgatgagaa tcgtcgggcc taagacttgc     240
agcaacacct ggcgtgggtc gttccccatt aacgcttaca ctacaggccc gtgcacgccc     300
tccccggcgc cgaactatac gttcgcgcta tgagggtgt ctgcagagga gtatgtggag     360
gtaaggcggc tggggacttt ccattacgtc acggggtga ccactgataa actcaagtgt     420
ccatgccagg tccctcacc cgagttctcc acagaggtgg acgggtgcg cctgcatagg     480 tacgcccctc cctgcaaacc cctgctacgg gatgaggtga cgtttagcgt cgggttcaat     540
gaatacctgg tggggtccca gttgccctgc gagcccgagc cagacgtagc agcattaaca     600

-continued

```
tcaatgctta cagacccttc ccacatcact gcaaagacgg cggcgcgtag gctgaagcgg    660
gggtctcccc cctccctggc cagttcttct gccagccagc tgtccgcgcc gtcactgaaa    720
gcaacatgca ccactcacca tgactctcca gacgccgacc tcatagaagc caacctcctg    780
tggagacggg agatggggggg aacatcacc agagtggagt cggagaacaa gattgttgtt    840
ctggattctt tcgacccgct cgtggcagag gaggatgacc gggagatttc tattccagct    900
gagattctgc ggaaatttaa gcagtttccc cccgccatgc ccatatgggc acggccggat    960
tataatcctc cccttgtgga accgtggaag cgcccggact gtgatccacc cttagtccac   1020
gggtgccccc taccacctcc caagccgact ccggtgccgc caccccggaa aaagaggacg   1080
gtggtgctgg acgagtctac agtatcatct gctctggctg agcttgccac taagaccttc   1140
ggcagctcta caacctcagg cgtgacaagt ggtgaagcgg ccgaatcgtc cccggcgctt   1200
tcctgcgacg gtgagctgga ctccgaagct gaatcttact cctccatgcc ccctctcgag   1260
ggggaaccgg gggaccccga tctcagcgac gggtcttggt ctaccgtgag cagtgatggc   1320
ggtacggagg atgtcgtgtg ctgctcgatg tcctactcgt ggacgggcgc cttaattacg   1380
ccctgtgccg cagaggaaac caaactcccc atcaacgcac tgagtaactc gctgctgcgc   1440
caccacaatt tggtgtattc caccacctct cgcagcgctg gcaagaggca gaaaaaagtc   1500
acatttgaca ggctgcaggt cctggacgat cattaccggg acgtgctcaa ggaggctaag   1560
gccaaggcat ccacagtgaa ggctaaattg ctatccgtag aggaggcatg tagcctgacg   1620
cccccgcact ccgccagatc aaaatttggc tatgggccga aggatgtccg aagccattcc   1680
agtaaggcta tacgccacat caactccgtg tggcaggacc ttctggagga caatacaaca   1740
cctatagaca ctaccatcat ggccaagaat gaagtcttct gcgtgaaggc cgaaaaaggg   1800
ggtcgcaagc ccgctcgcct tatcgtgtac cccgacctgg gggtgcgcgt gtgcgagaag   1860
agagctttgt atgacgtagt caaacagctc cccattgccg tgatgggacc ctcctacggg   1920
ttccagtact cgccagcgca gcgggtcgac ttcctgctta acgcgtggaa atcaaagaaa   1980
aaccctatgg ggttttccta tgacacccgt tgctttgact caacagtcac tgaggctgat   2040
atccgtacgg aggaagacct ctatcaatct tgtgacctgg tccctgaggc ccgcgcggcc   2100
ataaggtctc tcacagagag gctttacatc ggggcccac ttaccaattc taagggacaa   2160
aactgcggct atcggcgatg ccgcgcaagc ggcgtgctga ccactagctg cggtaacacc   2220
ataacttgct accttaaggc tagtgcggcc tgtcgagctg caaagctcca ggactgcacc   2280
atgctcgtgt gcggcgacga cctcgtcgtt atctgtgaaa gcgccggtgt caaggaggac   2340
gctgcgagcc tgagagcctt caccgaggct atgaccaggt actccggccc ccgggagac   2400 ccggctcaac cagaatacga cttggagctt ataacatcct gctcctccaa tgtgtcggtc   2460
gcgcgcgacg cgctggcca aagggtctat tatctgaccc gtgaacctga gactcccctc   2520
gcgcgtgccg cttgggagac agcaagacac actccagtga actcctggct aggcaacatc   2580
atcatgtttg cccccactct gtgggtacgg atggtcctca tgacccactt attctccata   2640
ctcatagttc aggagcacct tgaaaaggct ctagattgtg aaatctatgg agccacacac   2700
tccgtcccac cgttggacct acctgaaatc attcaaagac tccatggcct cagcgcgttt   2760
tcgctccaca gttactctcc aggtgaaatc aatagggtgg cttcatgcct caggaaactt   2820
ggggttccac ccttgcgagc ttggagacac cgggccccgga gcgtccgcgc cacactccta   2880 tcccagggg ggaaagccgc catatgcggt aagtacctct caactgggc ggtgaaaacc   2940
```

```
aaactcaaac tcattccatt accgctcgcg tctcatttgg acttgtccaa ttggttcacg    3000
ggcggctaca gcgggggaga catttatcac agcgtgtctc atgcccggcc ccgttggttt    3060
ctctggtgcc tactcctact ctcagtaggg gtaggcatct acctccttcc caaccga      3117
```

<210> SEQ ID NO 18
<211> LENGTH: 1039
<212> TYPE: PRT
<213> ORGANISM: Hepatitis C virus

<400> SEQUENCE: 18

```
Ala Ser Ser Trp Leu Lys Asp Val Trp Asn Trp Ile Cys Glu Val Leu
1               5                   10                  15

Ser Asp Phe Lys Asn Trp Leu Lys Ala Lys Leu Val Pro Gln Leu Pro
            20                  25                  30

Gly Ile Pro Phe Val Ser Cys Gln Arg Gly Tyr Arg Gly Val Trp Arg
        35                  40                  45

Gly Glu Gly Ile Val His Thr Arg Cys Pro Cys Gly Ala Asn Ile Thr
    50                  55                  60

Gly His Val Lys Asn Gly Ser Met Arg Ile Val Gly Pro Lys Thr Cys
65                  70                  75                  80

Ser Asn Thr Trp Arg Gly Ser Phe Pro Ile Asn Ala Tyr Thr Thr Gly
                85                  90                  95

Pro Cys Thr Pro Ser Pro Ala Pro Asn Tyr Thr Phe Ala Leu Trp Arg
            100                 105                 110

Val Ser Ala Glu Glu Tyr Val Glu Val Arg Arg Leu Gly Asp Phe His
        115                 120                 125

Tyr Val Thr Gly Val Thr Thr Asp Lys Leu Lys Cys Pro Cys Gln Val
    130                 135                 140

Pro Ser Pro Glu Phe Ser Thr Glu Val Asp Gly Val Arg Leu His Arg
145                 150                 155                 160

Tyr Ala Pro Pro Cys Lys Pro Leu Leu Arg Asp Glu Val Thr Phe Ser
                165                 170                 175

Val Gly Phe Asn Glu Tyr Leu Val Gly Ser Gln Leu Pro Cys Glu Pro
            180                 185                 190

Glu Pro Asp Val Ala Ala Leu Thr Ser Met Leu Thr Asp Pro Ser His
        195                 200                 205

Ile Thr Ala Lys Thr Ala Ala Arg Arg Leu Lys Arg Gly Ser Pro Pro
    210                 215                 220

Ser Leu Ala Ser Ser Ala Ser Gln Leu Ser Ala Pro Ser Leu Lys
225                 230                 235                 240

Ala Thr Cys Thr Thr His His Asp Ser Pro Asp Ala Asp Leu Ile Glu
                245                 250                 255

Ala Asn Leu Leu Trp Arg Arg Glu Met Gly Gly Asn Ile Thr Arg Val
            260                 265                 270

Glu Ser Glu Asn Lys Ile Val Val Leu Asp Ser Phe Asp Pro Leu Val
        275                 280                 285

Ala Glu Glu Asp Asp Arg Glu Ile Ser Ile Pro Ala Glu Ile Leu Arg
    290                 295                 300

Lys Phe Lys Gln Phe Pro Pro Ala Met Pro Ile Trp Ala Arg Pro Asp
305                 310                 315                 320

Tyr Asn Pro Pro Leu Val Glu Pro Trp Lys Arg Pro Asp Cys Asp Pro
                325                 330                 335

Pro Leu Val His Gly Cys Pro Leu Pro Pro Pro Lys Thr Pro Val
            340                 345                 350
```

-continued

```
Pro Pro Pro Arg Lys Lys Arg Thr Val Val Leu Asp Glu Ser Thr Val
        355                 360                 365

Ser Ser Ala Leu Ala Glu Leu Ala Thr Lys Thr Phe Gly Ser Ser Thr
    370                 375                 380

Thr Ser Gly Val Thr Ser Gly Glu Ala Ala Glu Ser Ser Pro Ala Leu
385                 390                 395                 400

Ser Cys Asp Gly Glu Leu Asp Ser Glu Ala Glu Ser Tyr Ser Ser Met
            405                 410                 415

Pro Pro Leu Glu Gly Glu Pro Gly Asp Pro Asp Leu Ser Asp Gly Ser
        420                 425                 430

Trp Ser Thr Val Ser Ser Asp Gly Gly Thr Glu Asp Val Val Cys Cys
        435                 440                 445

Ser Met Ser Tyr Ser Trp Thr Gly Ala Leu Ile Thr Pro Cys Ala Ala
    450                 455                 460

Glu Glu Thr Lys Leu Pro Ile Asn Ala Leu Ser Asn Ser Leu Leu Arg
465                 470                 475                 480

His His Asn Leu Val Tyr Ser Thr Thr Ser Arg Ser Ala Gly Lys Arg
                485                 490                 495

Gln Lys Lys Val Thr Phe Asp Arg Leu Gln Val Leu Asp Asp His Tyr
            500                 505                 510

Arg Asp Val Leu Lys Glu Ala Lys Ala Lys Ala Ser Thr Val Lys Ala
        515                 520                 525

Lys Leu Leu Ser Val Glu Glu Ala Cys Ser Leu Thr Pro Pro His Ser
    530                 535                 540

Ala Arg Ser Lys Phe Gly Tyr Gly Pro Lys Asp Val Arg Ser His Ser
545                 550                 555                 560

Ser Lys Ala Ile Arg His Ile Asn Ser Val Trp Gln Asp Leu Leu Glu
                565                 570                 575

Asp Asn Thr Thr Pro Ile Asp Thr Thr Ile Met Ala Lys Asn Glu Val
            580                 585                 590

Phe Cys Val Lys Ala Glu Lys Gly Gly Arg Lys Pro Ala Arg Leu Ile
        595                 600                 605

Val Tyr Pro Asp Leu Gly Val Arg Val Cys Glu Lys Arg Ala Leu Tyr
    610                 615                 620

Asp Val Val Lys Gln Leu Pro Ile Ala Val Met Gly Pro Ser Tyr Gly
625                 630                 635                 640

Phe Gln Tyr Ser Pro Ala Gln Arg Val Asp Phe Leu Leu Asn Ala Trp
                645                 650                 655

Lys Ser Lys Lys Asn Pro Met Gly Phe Ser Tyr Asp Thr Arg Cys Phe
            660                 665                 670

Asp Ser Thr Val Thr Glu Ala Asp Ile Arg Thr Glu Glu Asp Leu Tyr
        675                 680                 685

Gln Ser Cys Asp Leu Val Pro Glu Ala Arg Ala Ala Ile Arg Ser Leu
    690                 695                 700

Thr Glu Arg Leu Tyr Ile Gly Gly Pro Leu Thr Asn Ser Lys Gly Gln
705                 710                 715                 720

Asn Cys Gly Tyr Arg Arg Cys Arg Ala Ser Gly Val Leu Thr Thr Ser
                725                 730                 735

Cys Gly Asn Thr Ile Thr Cys Tyr Leu Lys Ala Ser Ala Ala Cys Arg
            740                 745                 750

Ala Ala Lys Leu Gln Asp Cys Thr Met Leu Val Cys Gly Asp Asp Leu
        755                 760                 765
```

Val Val Ile Cys Glu Ser Ala Gly Val Lys Glu Asp Ala Ala Ser Leu
    770                 775                 780

Arg Ala Phe Thr Glu Ala Met Thr Arg Tyr Ser Gly Pro Pro Gly Asp
785                 790                 795                 800

Pro Ala Gln Pro Glu Tyr Asp Leu Glu Leu Ile Thr Ser Cys Ser Ser
                805                 810                 815

Asn Val Ser Val Ala Arg Asp Gly Ala Gly Gln Arg Val Tyr Tyr Leu
            820                 825                 830

Thr Arg Glu Pro Glu Thr Pro Leu Ala Arg Ala Ala Trp Glu Thr Ala
        835                 840                 845

Arg His Thr Pro Val Asn Ser Trp Leu Gly Asn Ile Ile Met Phe Ala
    850                 855                 860

Pro Thr Leu Trp Val Arg Met Val Leu Met Thr His Leu Phe Ser Ile
865                 870                 875                 880

Leu Ile Val Gln Glu His Leu Glu Lys Ala Leu Asp Cys Glu Ile Tyr
                885                 890                 895

Gly Ala Thr His Ser Val Pro Pro Leu Asp Leu Pro Glu Ile Ile Gln
            900                 905                 910

Arg Leu His Gly Leu Ser Ala Phe Ser Leu His Ser Tyr Ser Pro Gly
        915                 920                 925

Glu Ile Asn Arg Val Ala Ser Cys Leu Arg Lys Leu Gly Val Pro Pro
    930                 935                 940

Leu Arg Ala Trp Arg His Arg Ala Arg Ser Val Arg Ala Thr Leu Leu
945                 950                 955                 960

Ser Gln Gly Gly Lys Ala Ala Ile Cys Gly Lys Tyr Leu Phe Asn Trp
                965                 970                 975

Ala Val Lys Thr Lys Leu Lys Leu Ile Pro Leu Pro Leu Ala Ser His
            980                 985                 990

Leu Asp Leu Ser Asn Trp Phe Thr Gly Gly Tyr Ser Gly Gly Asp Ile
        995                 1000                1005

Tyr His Ser Val Ser His Ala Arg Pro Arg Trp Phe Leu Trp Cys
    1010                1015                1020

Leu Leu Leu Leu Ser Val Gly Val Gly Ile Tyr Leu Leu Pro Asn
    1025                1030                1035

Arg

<210> SEQ ID NO 19
<211> LENGTH: 18
<212> TYPE: DNA
<213> ORGANISM: Artificial Sequence
<220> FEATURE:
<223> OTHER INFORMATION: Synthetic HCV Primer

<400> SEQUENCE: 19
gccagccccc tatggggg                                                  18

<210> SEQ ID NO 20
<211> LENGTH: 24
<212> TYPE: DNA
<213> ORGANISM: Artificial Sequence
<220> FEATURE:
<223> OTHER INFORMATION: Synthetic HCV Primer

<400> SEQUENCE: 20
gtttaggatt cgtgctcatg gtgc                                           24

<210> SEQ ID NO 21

```
<211> LENGTH: 25
<212> TYPE: DNA
<213> ORGANISM: Artificial Sequence
<220> FEATURE:
<223> OTHER INFORMATION: Synthetic HCV Primer

<400> SEQUENCE: 21
gaccgtgcac catgagcacg aatcc                                             25

<210> SEQ ID NO 22
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 22
tccgacggcc gaagcgggca                                                   20

<210> SEQ ID NO 23
<211> LENGTH: 24
<212> TYPE: DNA
<213> ORGANISM: Artificial Sequence
<220> FEATURE:
<223> OTHER INFORMATION: Synthetic HCV Primer

<400> SEQUENCE: 23
cccggttgct ctttctctat cttc                                              24

<210> SEQ ID NO 24
<211> LENGTH: 26
<212> TYPE: DNA
<213> ORGANISM: Artificial Sequence
<220> FEATURE:
<223> OTHER INFORMATION: Synthetic HCV Primer

<400> SEQUENCE: 24
ggatagatgg agcaattgca gtcttg                                            26

<210> SEQ ID NO 25
<211> LENGTH: 25
<212> TYPE: DNA
<213> ORGANISM: Artificial Sequence
<220> FEATURE:
<223> OTHER INFORMATION: Synthetic HCV Primer

<400> SEQUENCE: 25
caagactgca attgctccat ctatc                                             25

<210> SEQ ID NO 26
<211> LENGTH: 32
<212> TYPE: DNA
<213> ORGANISM: Artificial Sequence
<220> FEATURE:
<223> OTHER INFORMATION: Synthetic HCV Primer

<400> SEQUENCE: 26
agcctgtgct cgaccccccc cacatacatc ct                                     32

<210> SEQ ID NO 27
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 27
```
caactggatt caccaaggtg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 28
gcagactggc ctgcaagatc                                              20

<210> SEQ ID NO 29
<211> LENGTH: 19
<212> TYPE: DNA
<213> ORGANISM: Artificial Sequence
<220> FEATURE:
<223> OTHER INFORMATION: Synthetic HCV Primer

<400> SEQUENCE: 29
acatcaccaa aatcatgct                                               19

<210> SEQ ID NO 30
<211> LENGTH: 18
<212> TYPE: DNA
<213> ORGANISM: Artificial Sequence
<220> FEATURE:
<223> OTHER INFORMATION: Synthetic HCV Primer

<400> SEQUENCE: 30
cccagtgggt gcgtaatg                                                18

<210> SEQ ID NO 31
<211> LENGTH: 33
<212> TYPE: DNA
<213> ORGANISM: Artificial Sequence
<220> FEATURE:
<223> OTHER INFORMATION: Synthetic HCV Primer

<400> SEQUENCE: 31
cgcggatccg tgtgcacccg tggggttgca aag                               33

<210> SEQ ID NO 32
<211> LENGTH: 35
<212> TYPE: DNA
<213> ORGANISM: Artificial Sequence
<220> FEATURE:
<223> OTHER INFORMATION: Synthetic HCV Primer

<400> SEQUENCE: 32
cgaggcttct agctagtgac gacctccagg tccgc                             35

<210> SEQ ID NO 33
<211> LENGTH: 33
<212> TYPE: DNA
<213> ORGANISM: Artificial Sequence
<220> FEATURE:
<223> OTHER INFORMATION: Synthetic HCV Primer

<400> SEQUENCE: 33
cgcggatccg cccactgccc ctacctcgag cag                               33

<210> SEQ ID NO 34
<211> LENGTH: 35
<212> TYPE: DNA

<213> ORGANISM: Artificial Sequence
<220> FEATURE:
<223> OTHER INFORMATION: Synthetic HCV Primer

<400> SEQUENCE: 34
cgaagcttct aagcacacgg ggcgatgcaa tccga                          35

<210> SEQ ID NO 35
<211> LENGTH: 29
<212> TYPE: DNA
<213> ORGANISM: Artificial Sequence
<220> FEATURE:
<223> OTHER INFORMATION: Synthetic HCV Primer

<400> SEQUENCE: 35
ctgggactgg atatgcgagg tgctgagcg                                 29

<210> SEQ ID NO 36
<211> LENGTH: 28
<212> TYPE: DNA
<213> ORGANISM: Artificial Sequence
<220> FEATURE:
<223> OTHER INFORMATION: Synthetic HCV Primer

<400> SEQUENCE: 36
gagctgccaa ggtcttagtg gcaagctc                                  28

<210> SEQ ID NO 37
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 37
tatgggcacg gccggattat                                           20

<210> SEQ ID NO 38
<211> LENGTH: 22
<212> TYPE: DNA
<213> ORGANISM: Artificial Sequence
<220> FEATURE:
<223> OTHER INFORMATION: Synthetic HCV Primer

<400> SEQUENCE: 38
ttcattcttg gccatgatgg ta                                        22

<210> SEQ ID NO 39
<211> LENGTH: 22
<212> TYPE: DNA
<213> ORGANISM: Artificial Sequence
<220> FEATURE:
<223> OTHER INFORMATION: Synthetic HCV Primer

<400> SEQUENCE: 39
atagacacta ccatcatggc ca                                        22

<210> SEQ ID NO 40
<211> LENGTH: 21
<212> TYPE: DNA
<213> ORGANISM: Artificial Sequence
<220> FEATURE:
<223> OTHER INFORMATION: Synthetic HCV Primer

<400> SEQUENCE: 40
acggggccta aaggcctgga g                                         21

<210> SEQ ID NO 41
<211> LENGTH: 341
<212> TYPE: DNA
<213> ORGANISM: Hepatitis C Virus Isolate 1

<400> SEQUENCE: 41

```
gccagccccc tgatggggc gacactccac catgaatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c                        341
```

<210> SEQ ID NO 42
<211> LENGTH: 573
<212> TYPE: DNA
<213> ORGANISM: Hepatitis C Virus Isolate 1

<400> SEQUENCE: 42

```
atgagcacga atcctaaac

<211> LENGTH: 1274
<212> TYPE: DNA
<213> ORGANISM: Hepatitis C Virus Isolate 1

<400> SEQUENCE: 44

| |

<210> SEQ ID NO 46
<211> LENGTH: 1952
<212> TYPE: DNA
<213> ORGANISM: Hepatitis C virus

<400> SEQUENCE: 46

```
ggcc

<400> SEQUENCE: 47

```
agcacctggg tgctcgttgg cggcgtcctg gctgctttgg ccgcgtattg cctgtcaaca      60
ggctgcgtgg tcatagtggg cagggtcgtc ttgtccggga agccggcaat catacctgac     120
agggaagtcc tctaccgaga gttcgatgag atggaagagt gctctcagca cttaccgtac     180
atcgagcaag ggatgatgct cgccgagcag ttcaagcaga aggccctcgg cctcctgcag     240
accgcgtccc gtcaggcaga ggttatcgcc cctgctgtcc agaccaactg gcaaaaactc     300
gagaccttct gggcgaagca tatgtggaac ttcatcagtg ggatacaata cttggcgggc     360
ttgtcaacgc tgcctggtaa ccccgccatt gcttcattga tggcttttac agctgctgtc     420
accagcccac taaccactag ccaaaccctc ctcttcaaca tattgggggg gtgggtggct     480
gcccagctcg ccgcccccgg tgccgctact gcctttgtgg gcgctggctt agctggcgcc     540
gccatcggca gtgttggact ggggaaggtc ctcatagaca tccttgcagg gtatggcgcg     600
ggcgtggcgg gagctcttgt ggcattcaag atcatgagcg gtgaggtccc ctccacggag     660
gacctggtca atctactgcc cgccatcctc tcgcccggag ccctcgtagt cggcgtggtc     720
tgtgcagcaa tactgcgccg gcacgttggc ccgggcgagg gggcagtgca gtggatgaac     780
cggctgatag ccttcgcctc ccgggggaac catgtttccc ccacgcacta cgtgccggag     840
agcgatgcag ctgcccgcgt cactgccata ctcagcagcc tcactgtaac ccagctcctg     900
aggcgactgc accagtggat aagctcggag tgtaccactc catg                      944
```

<210> SEQ ID NO 48
<211> LENGTH: 3113
<212> TYPE: DNA
<213> ORGANISM: Hepatitis C Virus Isolate 1

<400> SEQUENCE: 48

```
gttcctggct

```
tcctcactga atcaacccta tctactgcct tggccgagct cgccaccaga agctttggca    1140
gctcctcaac ttccggcatt acgggcgaca atacgacaac atcctctgag cccgccccct    1200
ctggctgccc ccccgactcc gacgctgagt cctattcctc catgcccccc ctggagggg     1260 agcctgggga tccggatctt agcgacgggt catggtcaac ggtcagtagt gaggccaacg    1320
cggaggatgt cgtgtgctgc tcaatgtctt actcttggac aggcgcactc gtcaccccgt    1380
gcgccgcgga agaacagaaa ctgcccatca atgcactaag caactcgttg ctacgtcacc    1440
acaatttggt gtattccacc acctcacgca gtgcttgcca aaggcagaag aaagtcacat    1500
ttgacagact gcaagttctg acagccatt accaggacgt actcaaggag gttaaggcag     1560
cggcgtcaaa agtgaaggct aacttgctat ccgtagagga agcttgcagc ctgacgcccc    1620
cacactcagc caaatccaag tttggttatg gggcaaaaga cgtccgttgc catgccagaa    1680
aggccgtaag ccacatcaac tccgtgtgga agaccttct ggaagacaat gtaacaccaa      1740
tagacactac catcatggct aagaacgagg ttttctgcgt tcagcctgag aagggggtc      1800 gtaagccagc tcgtctcatc gtgttccccg atctgggcgt gcgcgtgtgc gaaaagagag    1860 cttttgtacga cgtggttaca aagctcccct tggccgtgat gggaagctcc tacggattcc    1920
aatactcacc aggacagcgg gttgaattcc tcgtgcacgc gtggaagtcc aagaaaaccc    1980
caatggggtt ctcgtatgat acccgctgct ttgactccac agtcactgag agcgacatcc    2040
gtacggagga ggcaatctac caatgttgtg acctcgaccc ccaagcccgc gtggccatca    2100
agtccctcac cgagaggctt tatgttgggg cccctcttac caattcaagg ggggagaact    2160
gcggctatcg caggtgccgc gcgagcggcg tactgacaac tagctgtggt aacaccctca    2220
cttgctacat caaggcccgg gcagcctgtc gagccgcagg gctccaggac tgcaccatgc    2280
tcgtgtgtgg cgacgactta gtcgttatct gtgaaagcgc gggggtccag gaggacgcgg    2340
cgagcctgag agccttcacg gaggctatga ccaggtactc cgcccccct ggggacccc      2400 cacaaccaga atacgacttg agctcataa catcatgctc ctccaacgtg tcagtcgcga    2460
acgacggcgc tggaaagagg gtctactacc tcacccgtga ccctacaacc ccctcgcga    2520 gagctgcgtg ggagacagca agacacactc cagtcaattc ctggctaggc aacataatca    2580
tgtttgcccc cacactgtgg gcgaggatga tactgatgac ccatttctttt agcgtcctta    2640 tagccaggga ccagcttgaa caggccctcg attgcgagat ctacggggcc tgctactcca    2700
tagaaccact tgatctacct ccaatcattc aaagactcca tggcctcagc gcattttcac    2760
tccacagtta ctctccaggt gaaattaata gggtggccgc atgcctcaga aaacttgggg    2820 taccgcccctt gcgagcttgg agacaccggg cccggagcgt ccgcgctagg cttctggcca    2880
gaggaggcag ggctgccata tgtggcaagt acctcttcaa ctgggcagta agaacaaagc    2940
tcaaactcac tccaatagcg gccgctggcc agctggactt gtccggctgg ttcacggctg    3000
gctacagcgg gggagacatt tatcacagcg tgtctcatgc ccggccccgc tggatctggt    3060
tttgcctact cctgcttgca gcagggggtag gcatctacct cctccccaac cga           3113
```

<210> SEQ ID NO 49
<211> LENGTH: 26
<212> TYPE: DNA
<213> ORGANISM: Hepatitis C Virus Isolate 1

<400> SEQUENCE: 49

```
gaaggttggg gtaaacactc cggcct                                            26
```

<210> SEQ ID NO 50
<211> LENGTH: 191
<212> TYPE: PRT
<213> ORGANISM: Hepatitis C Virus Isolate 1

<400> SEQUENCE: 50

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 51
<211> LENGTH: 190
<212> TYPE: PRT
<213> ORGANISM: Hepatitis C Virus Isolate 1

<400> SEQUENCE: 51

```
Val Arg Asn Ser Thr Gly Leu Tyr His Val Thr Asn Asp Cys Pro Asn
1               5                   10                  15

Ser Ser Ile Val Tyr Glu Ala Ala Asp Ala Ile Leu His Thr Pro Gly
            20                  25                  30

Cys Val Pro Cys Val Arg Glu Gly Asn Ala Ser Arg Cys Trp Val Ala
        35                  40                  45

Met Thr Pro Thr Val Ala Thr Arg Asp Gly Lys Leu Pro Ala Thr Gln
    50                  55                  60

Leu Arg Arg His Ile Asp Leu Leu Val Gly Ser Ala Thr Leu Cys Ser
65                  70                  75                  80

Ala Leu Tyr Val Gly Asp Leu Cys Gly Ser Val Phe Leu Val Gly Gln
                85                  90                  95

Leu Phe Thr Phe Ser Pro Arg Arg His Trp Thr Thr Gln Gly Cys Asn
            100                 105                 110

Cys Ser Ile Tyr Pro Gly His Ile Thr Gly His Arg Met Ala Trp Asp
        115                 120                 125

Met Met Met Asn Trp Ser Pro Thr Thr Ala Leu Val Met Ala Gln Leu
    130                 135                 140

Leu Arg Ile Pro Gln Ala Ile Leu Asp Met Ile Ala Gly Ala His Trp
```

```
            145                 150                 155                 160
Gly Val Leu Ala Gly Ile Ala Tyr Phe Ser Met Val Gly Asn Trp Ala
                165                 170                 175
Lys Val Leu Val Val Leu Leu Phe Ala Gly Val Asp Ala
            180                 185                 190

<210> SEQ ID NO 52
<211> LENGTH: 425
<212> TYPE: PRT
<213> ORGANISM: Hepatitis C Virus Isolate 1

<400> SEQUENCE: 52

Thr His Val Thr Gly Gly Ser Ala Gly His Thr Val Ser Gly Phe Val
1               5                   10                  15
Ser Leu Leu Ala Pro Gly Ala Lys Gln Asn Val Gln Leu Ile Asn Thr
                20                  25                  30
Asn Gly Ser Trp His Leu Asn Ser Thr Ala Leu Asn Cys Asn Asp Ser
            35                  40                  45
Leu Asn Thr Gly Trp Leu Ala Gly Leu Phe Tyr His His Lys Phe Asn
50                  55                  60
Ser Ser Gly Cys Pro Glu Arg Leu Ala Ser Cys Arg Pro Leu Thr Asp
65                  70                  75                  80
Phe Asp Gln Gly Trp Gly Pro Ile Ser Tyr Ala Asn Gly Ser Gly Pro
                85                  90                  95
Asp Gln Arg Pro Tyr Cys Trp His Tyr Pro Pro Lys Pro Cys Gly Ile
            100                 105                 110
Val Pro Ala Lys Ser Val Cys Gly Pro Val Tyr Cys Phe Thr Pro Ser
            115                 120                 125
Pro Val Val Val Gly Thr Thr Asp Arg Ser Gly Ala Pro Thr Tyr Ser
            130                 135                 140
Trp Gly Glu Asn Asp Thr Asp Val Phe Val Leu Asn Asn Thr Arg Pro
145                 150                 155                 160
Pro Leu Gly Asn Trp Phe Gly Cys Thr Trp Met Asn Ser Thr Gly Phe
                165                 170                 175
Thr Lys Val Cys Gly Ala Pro Pro Cys Val Ile Gly Gly Ala Gly Asn
            180                 185                 190
Asn Thr Leu His Cys Pro Thr Asp Cys Phe Arg Lys His Pro Asp Ala
            195                 200                 205
Thr Tyr Ser Arg Cys Gly Ser Gly Pro Trp Ile Thr Pro Arg Cys Leu
            210                 215                 220
Val Asp Tyr Pro Tyr Arg Leu Trp His Tyr Pro Cys Thr Ile Asn Tyr
225                 230                 235                 240
Thr Ile Phe Lys Ile Arg Met Tyr Val Gly Gly Val Glu His Arg Leu
                245                 250                 255
Glu Ala Ala Cys Asn Trp Thr Arg Gly Glu Arg Cys Asp Leu Glu Asp
            260                 265                 270
Arg Asp Arg Ser Glu Leu Ser Pro Leu Leu Leu Thr Thr Thr Gln Trp
            275                 280                 285
Gln Val Leu Pro Cys Ser Phe Thr Thr Leu Pro Ala Leu Ser Thr Gly
            290                 295                 300
Leu Ile His Leu His Gln Asn Ile Val Asp Val Gln Tyr Leu Tyr Gly
305                 310                 315                 320
Val Gly Ser Ser Ile Ala Ser Trp Ala Ile Lys Trp Glu Tyr Val Val
                325                 330                 335
```

-continued

```
Leu Leu Phe Leu Leu Leu Ala Asp Ala Arg Val Cys Ser Cys Leu Trp
            340                 345                 350

Met Met Leu Leu Ile Ser Gln Ala Glu Ala Ala Leu Glu Asn Leu Val
        355                 360                 365

Ile Leu Asn Ala Ala Ser Leu Ala Gly Thr His Gly Leu Val Ser Phe
    370                 375                 380

Leu Val Phe Phe Cys Phe Ala Trp Tyr Leu Lys Gly Lys Trp Val Pro
385                 390                 395                 400

Gly Ala Val Tyr Thr Phe Tyr Gly Met Trp Pro Leu Leu Leu Leu Leu
                405                 410                 415

Leu Ala Leu Pro Gln Arg Ala Tyr Ala
            420                 425

<210> SEQ ID NO 53
<211> LENGTH: 197
<212> TYPE: PRT
<213> ORGANISM: Hepatitis C Virus Isolate 1

<400> SEQUENCE: 53

Leu Asp Thr Glu Val Ala Ala Ser Cys Gly Gly Val Val Leu Val Gly
1               5                   10                  15

Leu Met Ala Leu Thr Leu Ser Pro Tyr Tyr Lys Arg Tyr Ile Ser Trp
            20                  25                  30

Cys Leu Trp Trp Leu Gln Tyr Phe Leu Thr Arg Val Glu Ala Gln Leu
        35                  40                  45

His Val Trp Ile Pro Pro Leu Asn Val Arg Gly Gly Arg Asp Ala Val
    50                  55                  60

Ile Leu Leu Met Cys Ala Val His Pro Thr Leu Val Phe Asp Ile Thr
65                  70                  75                  80

Lys Leu Leu Leu Ala Val Phe Gly Pro Leu Trp Ile Leu Gln Ala Ser
                85                  90                  95

Leu Leu Lys Val Pro Tyr Phe Val Arg Val Gln Gly Leu Leu Arg Phe
            100                 105                 110

Cys Ala Leu Ala Arg Lys Met Ile Gly Gly His Tyr Val Gln Met Val
        115                 120                 125

Ile Ile Lys Leu Gly Ala Leu Thr Gly Thr Tyr Val Tyr Asn His Leu
    130                 135                 140

Thr Pro Leu Arg Asp Trp Ala His Asn Gly Leu Arg Asp Leu Ala Val
145                 150                 155                 160

Ala Val Glu Pro Val Val Phe Ser Gln Met Glu Thr Lys Leu Ile Thr
                165                 170                 175

Trp Gly Ala Asp Thr Ala Ala Cys Gly Asp Ile Ile Asn Gly Leu Pro
            180                 185                 190

Val Ser Ala Arg Arg
        195

<210> SEQ ID NO 54
<211> LENGTH: 651
<212> TYPE: PRT
<213> ORGANISM: Hepatitis C Virus Isolate 1

<400> SEQUENCE: 54

Gly Arg Glu Ile Leu Leu Gly Pro Ala Asp Gly Met Val Ser Lys Gly
1               5                   10                  15

Trp Arg Leu Leu Ala Pro Ile Thr Ala Tyr Ala Gln Gln Thr Arg Gly
            20                  25                  30

-continued

```
Leu Leu Gly Cys Ile Ile Thr Ser Leu Thr Gly Arg Asp Lys Asn Gln
             35                  40                  45

Val Glu Gly Glu Val Gln Ile Val Ser Thr Ala Ala Gln Thr Phe Leu
 50                  55                  60

Ala Thr Cys Ile Asn Gly Val Cys Trp Thr Val Tyr His Gly Ala Gly
 65                  70                  75                  80

Thr Arg Thr Ile Ala Ser Pro Lys Gly Pro Val Ile Gln Met Tyr Thr
                 85                  90                  95

Asn Val Asp Gln Asp Leu Val Gly Trp Pro Ala Pro Gln Gly Ser Arg
                100                 105                 110

Ser Leu Thr Pro Cys Thr Cys Gly Ser Ser Asp Leu Tyr Leu Val Thr
            115                 120                 125

Arg His Ala Asp Val Ile Pro Val Arg Arg Gly Asp Ser Arg Gly
        130                 135                 140

Ser Leu Leu Ser Pro Arg Pro Ile Ser Tyr Leu Lys Gly Ser Ser Gly
145                 150                 155                 160

Gly Pro Leu Leu Cys Pro Ala Gly His Ala Val Gly Ile Phe Arg Ala
                165                 170                 175

Ala Val Cys Thr Arg Gly Val Ala Lys Ala Val Asp Phe Ile Pro Val
            180                 185                 190

Glu Asn Leu Glu Thr Thr Met Arg Ser Pro Val Phe Thr Asp Asn Ser
        195                 200                 205

Ser Pro Pro Val Val Pro Gln Ser Phe Gln Val Ala His Leu His Ala
    210                 215                 220

Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255

Gly Phe Gly Ala Tyr Met Ser Lys Ala His Gly Ile Asp Pro Asn Ile
            260                 265                 270

Arg Thr Gly Val Arg Thr Ile Thr Thr Gly Ser Pro Ile Thr Tyr Ser
        275                 280                 285

Thr Tyr Gly Lys Phe Leu Ala Asp Gly Gly Cys Ser Gly Gly Ala Tyr
    290                 295                 300

Asp Ile Ile Ile Cys Asp Glu Cys His Ser Thr Asp Ala Thr Ser Ile
305                 310                 315                 320

Leu Gly Ile Gly Thr Val Leu Asp Gln Ala Glu Thr Ala Gly Ala Arg
                325                 330                 335

Leu Val Val Leu Ala Thr Ala Thr Pro Pro Gly Ser Val Thr Val Pro
            340                 345                 350

His Pro Asn Ile Glu Glu Val Ala Leu Ser Thr Thr Gly Glu Ile Pro
        355                 360                 365

Phe Tyr Gly Lys Ala Ile Pro Leu Glu Val Ile Lys Gly Gly Arg His
    370                 375                 380

Leu Ile Phe Cys His Ser Lys Lys Cys Asp Glu Leu Ala Ala Lys
385                 390                 395                 400

Leu Val Ala Leu Gly Ile Asn Ala Val Ala Tyr Tyr Arg Gly Leu Asp
                405                 410                 415

Val Ser Val Ile Pro Thr Ser Gly Asp Val Val Val Ala Thr Asp
            420                 425                 430

Ala Leu Met Thr Gly Tyr Thr Gly Asp Phe Asp Ser Val Ile Asp Cys
        435                 440                 445

Asn Thr Cys Val Thr Gln Thr Val Asp Phe Ser Leu Asp Pro Thr Phe
```

```
                450                 455                 460
Thr Ile Glu Thr Ile Thr Leu Pro Gln Asp Ala Val Ser Arg Thr Gln
465                 470                 475                 480

Arg Arg Gly Arg Thr Gly Arg Gly Lys Pro Gly Ile Tyr Arg Phe Val
                485                 490                 495

Ala Pro Gly Glu Arg Pro Ser Gly Met Phe Asp Ser Ser Val Leu Cys
            500                 505                 510

Glu Cys Tyr Asp Ala Gly Cys Ala Trp Tyr Glu Leu Thr Pro Ala Glu
        515                 520                 525

Thr Thr Val Arg Leu Arg Ala Tyr Met Asn Thr Pro Gly Leu Pro Val
    530                 535                 540

Cys Gln Asp His Leu Glu Phe Trp Glu Gly Val Phe Thr Gly Leu Thr
545                 550                 555                 560

His Ile Asp Ala His Phe Leu Ser Gln Thr Lys Gln Ser Gly Glu Asn
                565                 570                 575

Leu Pro Tyr Leu Val Ala Tyr Gln Ala Thr Val Cys Ala Arg Ala Gln
            580                 585                 590

Ala Pro Pro Pro Ser Trp Asp Gln Met Trp Lys Cys Leu Ile Arg Leu
        595                 600                 605

Lys Pro Thr Leu His Gly Pro Thr Pro Leu Leu Tyr Arg Leu Gly Ala
    610                 615                 620

Val Gln Asn Glu Ile Thr Leu Thr His Pro Val Thr Lys Tyr Ile Met
625                 630                 635                 640

Thr Cys Met Ser Ala Asp Leu Glu Val Val Thr
                645                 650

<210> SEQ ID NO 55
<211> LENGTH: 315
<212> TYPE: PRT
<213> ORGANISM: Hepatitis C Virus Isolate 1

<400> SEQUENCE: 55

Ser Thr Trp Val Leu Val Gly Gly Val Leu Ala Ala Leu Ala Ala Tyr
1               5                   10                  15

Cys Leu Ser Thr Gly Cys Val Val Ile Val Gly Arg Val Val Leu Ser
                20                  25                  30

Gly Lys Pro Ala Ile Ile Pro Asp Arg Glu Val Leu Tyr Arg Glu Phe
            35                  40                  45

Asp Glu Met Glu Glu Cys Ser Gln His Leu Pro Tyr Ile Glu Gln Gly
        50                  55                  60

Met Met Leu Ala Glu Gln Phe Lys Gln Lys Ala Leu Gly Leu Leu Gln
65                  70                  75                  80

Thr Ala Ser Arg Gln Ala Glu Val Ile Ala Pro Ala Val Gln Thr Asn
                85                  90                  95

Trp Gln Lys Leu Glu Thr Phe Trp Ala Lys His Met Trp Asn Phe Ile
            100                 105                 110

Ser Gly Ile Gln Tyr Leu Ala Gly Leu Ser Thr Leu Pro Gly Asn Pro
        115                 120                 125

Ala Ile Ala Ser Leu Met Ala Phe Thr Ala Ala Val Thr Ser Pro Leu
    130                 135                 140

Thr Thr Ser Gln Thr Leu Leu Phe Asn Ile Leu Gly Gly Trp Val Ala
145                 150                 155                 160

Ala Gln Leu Ala Ala Pro Gly Ala Ala Thr Ala Phe Val Gly Ala Gly
                165                 170                 175
```

-continued

```
Leu Ala Gly Ala Ala Ile Gly Ser Val Gly Leu Gly Lys Val Leu Ile
            180                 185                 190

Asp Ile Leu Ala Gly Tyr Gly Ala Gly Val Ala Gly Ala Leu Val Ala
            195                 200                 205

Phe Lys Ile Met Ser Gly Glu Val Pro Ser Thr Glu Asp Leu Val Asn
            210                 215                 220

Leu Leu Pro Ala Ile Leu Ser Pro Gly Ala Leu Val Val Gly Val Val
225                 230                 235                 240

Cys Ala Ala Ile Leu Arg Arg His Val Gly Pro Gly Glu Gly Ala Val
                    245                 250                 255

Gln Trp Met Asn Arg Leu Ile Ala Phe Ala Ser Arg Gly Asn His Val
                260                 265                 270

Ser Pro Thr His Tyr Val Pro Glu Ser Asp Ala Ala Ala Arg Val Thr
            275                 280                 285

Ala Ile Leu Ser Ser Leu Thr Val Thr Gln Leu Leu Arg Arg Leu His
            290                 295                 300

Gln Trp Ile Ser Ser Glu Cys Thr Thr Pro Cys
305                 310                 315

<210> SEQ ID NO 56
<211> LENGTH: 1039
<212> TYPE: PRT
<213> ORGANISM: Hepatitis C Virus Isolate 1

<400> SEQUENCE: 56

Ser Gly Ser Trp Leu Arg Asp Ile Trp Asp Trp Ile Cys Glu Val Leu
1               5                   10                  15

Ser Asp Phe Lys Thr Trp Leu Lys Ala Lys Leu Met Pro Gln Leu Pro
            20                  25                  30

Gly Ile Pro Phe Val Ser Cys Gln Arg Gly Tyr Lys Gly Val Trp Arg
            35                  40                  45

Val Asp Gly Ile Met His Thr Arg Cys His Cys Gly Ala Glu Ile Thr
        50                  55                  60

Gly His Val Lys Asn Gly Thr Met Arg Ile Val Gly Pro Arg Thr Cys
65                  70                  75                  80

Arg Asn Met Trp Ser Gly Thr Phe Pro Ile Asn Ala Tyr Thr Thr Gly
                85                  90                  95

Pro Cys Thr Pro Leu Pro Ala Pro Asn Tyr Thr Phe Ala Leu Trp Arg
            100                 105                 110

Val Ser Ala Glu Glu Tyr Val Glu Ile Arg Gln Val Gly Asp Phe His
            115                 120                 125

Tyr Val Thr Gly Met Thr Thr Asp Asn Leu Lys Cys Pro Cys Gln Val
        130                 135                 140

Pro Ser Pro Glu Phe Phe Thr Glu Leu Asp Gly Val Arg Leu His Arg
145                 150                 155                 160

Phe Ala Pro Pro Cys Lys Pro Leu Leu Arg Glu Glu Val Ser Phe Arg
                165                 170                 175

Val Gly Leu His Glu Tyr Pro Val Gly Ser Gln Leu Pro Cys Glu Pro
            180                 185                 190

Glu Pro Asp Val Ala Val Leu Thr Ser Met Leu Thr Asp Pro Ser His
            195                 200                 205

Ile Thr Ala Glu Ala Ala Gly Arg Arg Leu Ala Arg Gly Ser Pro Pro
        210                 215                 220

Ser Val Ala Ser Ser Ser Ala Ser Gln Leu Ser Ala Pro Ser Leu Lys
225                 230                 235                 240
```

-continued

```
Ala Thr Cys Thr Ala Asn His Asp Ser Pro Asp Ala Glu Leu Ile Glu
                245                 250                 255

Ala Asn Leu Leu Trp Arg Gln Glu Met Gly Asn Ile Thr Arg Val
        260                 265                 270

Glu Ser Glu Asn Lys Val Val Ile Leu Asp Ser Phe Asp Pro Leu Val
        275                 280                 285

Ala Glu Glu Asp Glu Arg Glu Ile Ser Val Pro Ala Glu Ile Leu Arg
    290                 295                 300

Lys Ser Arg Arg Phe Ala Gln Ala Leu Pro Val Trp Ala Arg Pro Asp
305                 310                 315                 320

Tyr Asn Pro Pro Leu Val Glu Thr Trp Lys Lys Pro Asp Tyr Glu Pro
                325                 330                 335

Pro Val Val His Gly Cys Pro Leu Pro Pro Lys Ser Pro Pro Val
            340                 345                 350

Pro Pro Pro Arg Lys Lys Arg Thr Val Val Leu Thr Glu Ser Thr Leu
            355                 360                 365

Ser Thr Ala Leu Ala Glu Leu Ala Thr Arg Ser Phe Gly Ser Ser Ser
    370                 375                 380

Thr Ser Gly Ile Thr Gly Asp Asn Thr Thr Thr Ser Ser Glu Pro Ala
385                 390                 395                 400

Pro Ser Gly Cys Pro Pro Asp Ser Asp Ala Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Ser Glu Ala Asn Ala Glu Asp Val Val Cys Cys
            435                 440                 445

Ser Met Ser Tyr Ser Trp Thr Gly Ala Leu Val Thr Pro Cys Ala Ala
    450                 455                 460

Glu Glu Gln Lys Leu Pro Ile Asn Ala Leu Ser Asn Ser Leu Leu Arg
465                 470                 475                 480

His His Asn Leu Val Tyr Ser Thr Thr Ser Arg Ser Ala Cys Gln Arg
                485                 490                 495

Gln Lys Lys Val Thr Phe Asp Arg Leu Gln Val Leu Asp Ser His Tyr
            500                 505                 510

Gln Asp Val Leu Lys Glu Val Lys Ala Ala Ala Ser Lys Val Lys Ala
            515                 520                 525

Asn Leu Leu Ser Val Glu Glu Ala Cys Ser Leu Thr Pro Pro His Ser
    530                 535                 540

Ala Lys Ser Lys Phe Gly Tyr Gly Ala Lys Asp Val Arg Cys His Ala
545                 550                 555                 560

Arg Lys Ala Val Thr His Ile Asn Ser Val Trp Lys Asp Leu Leu Glu
                565                 570                 575

Asp Asn Val Thr Pro Ile Asp Thr Thr Ile Met Ala Lys Asn Glu Val
            580                 585                 590

Phe Cys Val Gln Pro Glu Lys Gly Gly Arg Lys Pro Ala Arg Leu Ile
        595                 600                 605

Val Phe Pro Asp Leu Gly Val Arg Val Cys Glu Lys Met Ala Leu Tyr
    610                 615                 620

Asp Val Val Thr Lys Leu Pro Leu Ala Val Met Gly Ser Ser Tyr Gly
625                 630                 635                 640

Phe Gln Tyr Ser Pro Gly Gln Arg Val Glu Phe Leu Val Gln Ala Trp
                645                 650                 655
```

```
Lys Ser Lys Lys Thr Pro Met Gly Phe Ser Tyr Asp Thr Arg Cys Phe
            660             665             670

Asp Ser Thr Val Thr Glu Ser Asp Ile Arg Thr Glu Glu Ala Ile Tyr
            675             680             685

Gln Cys Cys Asp Leu Asp Pro Gln Ala Arg Val Ala Ile Lys Ser Leu
            690             695             700

Thr Glu Arg Leu Tyr Val Gly Gly Pro Leu Thr Asn Ser Arg Gly Glu
705             710             715             720

Asn Cys Gly Tyr Arg Arg Cys Arg Ala Ser Gly Val Leu Thr Thr Ser
            725             730             735

Cys Gly Asn Thr Leu Thr Cys Tyr Ile Lys Ala Arg Ala Ala Cys Arg
            740             745             750

Ala Ala Gly Leu Gln Asp Cys Thr Met Leu Val Cys Gly Asp Asp Leu
            755             760             765

Val Val Ile Cys Glu Ser Ala Gly Val Gln Glu Asp Ala Ala Ser Leu
            770             775             780

Arg Ala Phe Thr Glu Ala Met Thr Arg Tyr Ser Ala Pro Pro Gly Asp
785             790             795             800

Pro Pro Gln Pro Glu Tyr Asp Leu Glu Leu Ile Thr Ser Cys Ser Ser
            805             810             815

Asn Val Ser Val Ala His Asp Gly Ala Gly Lys Arg Val Tyr Tyr Leu
            820             825             830

Thr Arg Asp Pro Thr Thr Pro Leu Ala Arg Ala Ala Trp Glu Thr Ala
            835             840             845

Arg His Thr Pro Val Asn Ser Trp Leu Gly Asn Ile Ile Met Phe Ala
            850             855             860

Pro Thr Leu Trp Ala Arg Met Ile Leu Met Thr His Phe Phe Ser Val
865             870             875             880

Leu Ile Ala Arg Asp Gln Leu Glu Gln Ala Leu Asp Cys Glu Ile Tyr
            885             890             895

Gly Ala Cys Tyr Ser Ile Glu Pro Leu Asp Leu Pro Pro Ile Ile Gln
            900             905             910

Arg Leu His Gly Leu Ser Ala Phe Ser Leu His Ser Tyr Ser Pro Gly
            915             920             925

Glu Ile Asn Arg Val Ala Ala Cys Leu Arg Lys Leu Gly Val Pro Pro
            930             935             940

Leu Arg Ala Trp Arg His Arg Ala Arg Ser Val Arg Ala Arg Leu Leu
945             950             955             960

Ala Arg Gly Gly Arg Ala Ala Ile Cys Gly Lys Tyr Leu Phe Asn Trp
            965             970             975

Ala Val Arg Thr Lys Leu Lys Leu Thr Pro Ile Ala Ala Gly Gln
            980             985             990

Leu Asp Leu Ser Gly Trp Phe Thr Ala Gly Tyr Ser Gly Gly Asp Ile
            995             1000            1005

Tyr His Ser Val Ser His Ala Arg Pro Arg Trp Ile Trp Phe Cys
            1010            1015            1020

Leu Leu Leu Leu Ala Ala Gly Val Gly Ile Tyr Leu Leu Pro Asn
            1025            1030            1035

Arg
```